United States Patent
Nelms et al.

(10) Patent No.: US 11,718,609 B2
(45) Date of Patent: Aug. 8, 2023

(54) HEPARANASE INHIBITORS AND USE THEREOF

(71) Applicant: Beta Therapeutics Pty Ltd, Canberra (AU)

(72) Inventors: Keats Nelms, Canberra (AU); Brett Schwartz, Canberra (AU); Colin Jackson, Canberra (AU); Martin Banwell, Canberra (AU); Edward Hammond, Canberra (AU)

(73) Assignee: BETA THERAPEUTICS PTY LTD, Canberra Act (AU)

( * ) Notice: Subject to any disclaimer, the term of this patent is extended or adjusted under 35 U.S.C. 154(b) by 223 days.

(21) Appl. No.: 16/468,419

(22) PCT Filed: Dec. 13, 2017

(86) PCT No.: PCT/AU2017/000270
§ 371 (c)(1),
(2) Date: Jun. 11, 2019

(87) PCT Pub. No.: WO2018/107200
PCT Pub. Date: Jun. 21, 2018

(65) Prior Publication Data
US 2021/0130338 A1 May 6, 2021

Related U.S. Application Data

(60) Provisional application No. 62/433,652, filed on Dec. 13, 2016.

(30) Foreign Application Priority Data

Jun. 20, 2017 (AU) ................. 2017902346

(51) Int. Cl.
| | | |
|---|---|---|
| C07D 413/12 | (2006.01) |
| C07D 413/14 | (2006.01) |
| C07D 403/14 | (2006.01) |
| C07D 403/04 | (2006.01) |
| C07D 403/06 | (2006.01) |
| C07D 403/12 | (2006.01) |
| C07D 417/12 | (2006.01) |
| C07D 239/94 | (2006.01) |
| C07D 239/95 | (2006.01) |
| C07D 401/04 | (2006.01) |
| C07D 401/12 | (2006.01) |
| C07D 401/14 | (2006.01) |
| C07D 471/04 | (2006.01) |
| A61P 3/10 | (2006.01) |
| A61P 3/00 | (2006.01) |
| A61P 27/02 | (2006.01) |
| A61P 35/00 | (2006.01) |
| A61P 9/00 | (2006.01) |
| A61K 31/517 | (2006.01) |
| C07D 405/14 | (2006.01) |

(52) U.S. Cl.
CPC .............. *C07D 413/12* (2013.01); *A61P 3/10* (2018.01); *A61P 27/02* (2018.01); *C07D 403/14* (2013.01); *C07D 405/14* (2013.01); *C07D 413/14* (2013.01); *C07D 417/12* (2013.01)

(58) Field of Classification Search
CPC .......... A61P 3/10; A61P 27/02; C07D 403/06; C07D 403/04; C07D 403/14; C07D 403/12; C07D 413/12; C07D 413/14; C07D 35/00; C07D 27/02; C07D 401/12; C07D 401/14; C07D 401/04; C07D 471/04; C07D 3/00; C07D 417/12; C07D 405/12; C07D 405/14; C07D 239/94; A61K 31/517
See application file for complete search history.

(56) References Cited

U.S. PATENT DOCUMENTS

| | | |
|---|---|---|
| 4,341,893 A | 7/1982 | Manoury et al. |
| 4,668,787 A | 5/1987 | Bandurco et al. |
| 4,717,373 A | 1/1988 | Catchman et al. |
| 5,288,704 A | 2/1994 | Ungheri |
| 5,439,895 A | 8/1995 | Lee et al. |
| 5,514,667 A | 5/1996 | Cullis-Hill |
| 5,980,865 A | 11/1999 | Ahmed |
| 8,377,948 B2 | 2/2013 | Chen et al. |
| 2005/0074497 A1 | 4/2005 | Schultz |
| 2007/0270354 A1 | 11/2007 | Petitou et al. |
| 2011/0066101 A1 | 3/2011 | Miller et al. |
| 2011/0189174 A1 | 8/2011 | Shafiee |
| 2013/0143840 A1 | 6/2013 | Parish et al. |
| 2014/0005140 A1 | 1/2014 | Piron et al. |

FOREIGN PATENT DOCUMENTS

| | | |
|---|---|---|
| DE | 2720545 A1 | 11/1977 |
| EP | 0594877 A1 | 5/1994 |
| EP | 2484359 A1 | 8/2012 |
| JP | 2011074024 A | 4/2011 |
| JP | 2011074027 A | 4/2011 |

(Continued)

OTHER PUBLICATIONS

RN 1317296-43-7, Oct. 14, 2011, registry database compound.*
RN116784-56-6, registry database compound, 1988.*
RN1319122-09-2, registry database compound, 2011.*
Cancer—Prevention, 2022, https://www.cancerresearchuk.org/about-cancer/causes-of-cancer/can-cancer-be-prevented-0.*

(Continued)

*Primary Examiner* — Sun Jae Yoo

(57) ABSTRACT

The invention relates to functionalized quinazoline compounds, pharmaceutical compositions comprising such compounds, and the use of such compounds as heparanase inhibitors for the treatment of diseases or conditions related to heparanse activity.

19 Claims, 8 Drawing Sheets

(56) References Cited

FOREIGN PATENT DOCUMENTS

| WO | WO 1990/012580 A | 11/1990 |
|---|---|---|
| WO | WO 1995/005182 A1 | 2/1995 |
| WO | WO 1995/009637 A1 | 4/1995 |
| WO | WO 1996/009828 A1 | 4/1996 |
| WO | WO 1996/033726 A1 | 10/1996 |
| WO | WO 1996/035700 A1 | 11/1996 |
| WO | WO 2000/025817 A1 | 5/2000 |
| WO | WO 2000/031082 A1 | 6/2000 |
| WO | WO 2001/055221 A1 | 8/2001 |
| WO | WO 2002/024667 A1 | 3/2002 |
| WO | WO 2002/060373 A2 | 8/2002 |
| WO | WO 2002/060374 A2 | 8/2002 |
| WO | WO 2002/060375 A2 | 8/2002 |
| WO | WO 2002/060867 A2 | 8/2002 |
| WO | WO 2002/076976 A2 | 10/2002 |
| WO | WO 2003/004454 A1 | 1/2003 |
| WO | WO 2003/022291 A1 | 3/2003 |
| WO | WO 2003/030989 A1 | 4/2003 |
| WO | WO 2003/043689 A1 | 5/2003 |
| WO | WO 2003/078427 A1 | 9/2003 |
| WO | WO 2003/097025 A2 | 11/2003 |
| WO | WO 2004/030672 A1 | 4/2004 |
| WO | WO 2004/043989 A1 | 5/2004 |
| WO | WO 2004/046122 A1 | 6/2004 |
| WO | WO 2004/070008 A2 | 8/2004 |
| WO | WO 2004/108065 A2 | 12/2004 |
| WO | WO 2005/085264 A1 | 9/2005 |
| WO | WO 2006/047788 A2 | 5/2006 |
| WO | WO 2007/050645 A2 | 5/2007 |
| WO | WO 2007/081750 A2 | 7/2007 |
| WO | WO 2007/099406 A2 | 9/2007 |
| WO | WO 2008/013913 A2 | 1/2008 |
| WO | WO 2008/046162 A2 | 4/2008 |
| WO | WO 2008/134430 A1 | 11/2008 |
| WO | WO 2009/049370 A1 | 4/2009 |
| WO | WO 2010/006982 A1 | 1/2010 |
| WO | WO 2010/009087 A1 | 1/2010 |
| WO | WO 2010/038060 A1 | 4/2010 |
| WO | WO 2010/078246 A1 | 7/2010 |
| WO | WO 2010/104851 A1 | 9/2010 |
| WO | WO 2011/082337 A1 | 7/2011 |
| WO | WO 2012/101544 A1 | 8/2012 |
| WO | WO 2013/052899 A1 | 4/2013 |
| WO | WO 2014/100501 A1 | 6/2014 |
| WO | WO 2014/114723 A1 | 7/2014 |
| WO | WO 2015/164374 A1 | 10/2015 |
| WO | WO 2016/118933 A1 | 7/2016 |

OTHER PUBLICATIONS

Diabetes—Prevention, 2022, https://www.cdc.gov/diabetes/basics/what-is-type-1-diabetes.html#:~:text=Currently%2C%20no%20one%20knows%20how,Getting%20regular%20health%20checkups.*
Cancer—cure, 2022, https://www.healthline.com/health/is-there-a-cure-for-cancer.*
Diabetes—cure, 2022, https://diabetesresearch.org/type-1-diabetes-cure/.*
Coombe—et-al., Front. Oncol., 2019, 60 pages.*
Giardina—et-al., J. Med. Chem., 1989, 32, 50-55.*
Hamoud—et-al., 2017, https://www.ncbi.nlm.nih.gov/pmc/articles/PMC5684525/.*
Abu El-Asrar et al, "Upregulated expression of heparanase in the vitreous of patients with proliferative diabetic retinopathy originates from activated endothelial cells and leukocytes", Investigative Ophthalmology & Visual Science (2015), vol. 56, No. 13, pp. 8239-8247.
Abu El-Asrar et al, "Coexpression of heparanase activity, cathepsin L, tissue factor, tissue factor pathway inhibitor, and MMP-9 in proliferative diabetic retinopathy", Molecular Vision (2016), vol. 22, pp. 424-435, Published Apr. 30, 2016.
Agelidis, A.M., et al., "Viral Activation of Heparanase Drives Pathogenesis of Herpes Simplex Virus-1", Cell Rep., v. 20, p. 439-450 (2017).
Baburajeev et al. (2017) BMC Cancer, 17: 235.
Bamoharram, F. F. et al: 'Dawson Heteropolyacid: A Green, Eco-Friendly, and Reusable Catalyst for One-Pot Synthesis of 4-Aminoquinazolines', Synthesis and Reactivity in Inorganic, Metal-Organic, and Nano-Metal Chemistry (2013), 43(5), pp. 539-542.
Barthlein et al. (2003) J Pediatric Surgery, 38(9): 1296-1304.
Basappa et al. (2010) Cancer Letters, 297: 231-243.
Benezra et al. (2002) J Cell Physiol, 192(3): 245-358.
Bentolila et al. (2000) J Med Chem, 43(13): 2591-2600.
Berge, S.M., et al., "Pharmaceutical Salts", J. of Pharm. Sci., v. 66, p. 1-19 (1977).
CAS Registry No. 21580-54-1, STN entry date: Nov. 16, 1984; Chemical Name: 4-Quinazolinamine, 6,7-dimethoxy-2-phenyl.
CAS Registry No. 361154-65-6, STN entry date: Oct. 9, 2001; Chemical Name: 4-Quinazolinamine, 6, 7-dimethoxy-2-( 4-methyl-l-piperazinyl)-N-(2-phenylethyl).
CAS Registry No. 422531-79-1, STN entry date: May 29, 2002, Chemical name: 2( IH)-Quinazolinethione, 4-[[2-( IH-indol-3-yl)ethyl]amino ].
CAS Registry No. 439097-17-3, STN entry date: Jul. 17, 2002, Chemical name: 2( 1 H)-Quinazolinethione, 3 ,4-dihydro-4-imino-6, 7-dimethoxy-3-[3-( 4-morpholinyl)propyl].
CAS Registry No. 477848-75-2, STN entry date: Dec. 31, 2002, Chemical name: 2( 1 H)-Quinazolinethione, 3 ,4-dihydro-4-imino-6, 7-dimethoxy-3-(2-phenylethyl).
CAS Registry No. 691858-06-7, STN entry date: Jun. 11, 2004, Chemical name: 4(3H)-Quinazolinimine, 6, 7-dimethoxy-3-(2-phenylethyl)-2-[[[ 4-(trifluoromethyl)phenyl]methyl]thio ].
CAS Registry No. 740066-32-4, STN entry date: Sep. 5, 2004; Chemical Name: 1,4-Benzodioxin-2-carboxamide, N-[2-[( 4-amino-6, 7-dimethoxy-2-quinazolinyl)amino ]ethyl]-2,3-dihydro.
CAS Registry No. 860610-60-2, STN entry date: Aug. 17, 2005, Chemical name: 2( 1 H)-Quinazolinethione, 3-amino-3 ,4-dihydro-4-imino-6, 7-dimethoxy.
CAS Registry No. 860610-62-4, STN entry date: Aug. 17, 2005, Chemical name: 4(3H)-Quinazolinimine, 3-[ (2-chlorophenyl)methyl ]-6, 7-dimethoxy-2-[[[3-(trifluoromethyl)phenyl]methyl]thio ].
CAS Registry No. 896670-06-7, STN entry date: Jul. 28, 2006, Chemical name: 2( 1 H)-Quinazolinethione, 3 ,4-dihydro-4-imino-3-[2-( 1 H-indol-3-yl)ethyl].
CAS Registry No. 1095750-67-6, STN entry date: Jan. 25, 2009; Chemical Name:2,4-Quinazolinediamine, N2,N4-bis[( 4-fluorophenyl)methyl]-6, 7-dimethoxy.
CAS Registry No. 1317296-43-7, STN entry date: Aug. 14, 2011; Chemical Name: Benzenesulfonamide, N-[2-[ ( 4-amino-6, 7-dimethoxy-2-quinazolinyl)amino ]ethyl]-2,5-dimethyl.
CAS Registry No. 1417397-54-6, STN entry date: Jan. 24, 2013; Chemical Name: 4-Quinazolinamine, 6-ethoxy-2-(3-pyridinyl)-N-(2-pyridinylmethyl).
CAS Registry No. 1609893-59-5, STN entry date: Jun. 7, 2014; Chemical Name: 4-Quinazolinamine, 2-(2,3-dihydro-7-benzofuranyl)-6, 7-dimethoxy.
CASPI (2006) Drug Discovery Today: Disease Models, 3(1): 3-9.
Chen et al. (2007) J Agric Food Chem, 55: 6910-6917.
Chen, M., et al., "Parainflammation, chronic inflammation, and age-related macular degeneration", J. Leuk. Biol., v. 98, n. 5, p. 713-725 (2015).
Chinnery, H.R., et al., "Macrophage physiology in the eye", Eur. J. Physiol., v. 469, p. 501-515 (2017).
Cho et al., Discovery of 2-Aryloxy-4-Amino-Qunazoline Derivatives as Novel Protease-Activated Receptor 2 (PAR2) Antagoists.
Cornish et al. (2005) Vis Neurosci, 22: 447-459.
Courtney et al. (2004) Bioorg Med Chem Lett, 14(12): 3269-3273.
Courtney, S.M. et al., "Furanyl-1,3-thiazol-2-yl and benzoxazol-5-yl acetic acid derivatives: novel classes of heparanase inhibitor", Bioorg Med Chem Lett, 15(9):2295-9 (2005).
Curcio et al. (1998) Invest Ophthalmol Vis Sci, 39: 1085-1096.
Dithmer et al, "Fucoidan Reduces Secretion and Expression of Vascular Endothelial Growth Factor in the Retinal Pigment Epithelium and Reduces Angiogenesis In Vitro", PLoS One (2014), vol. 9, No. 2, p. e89150, 10 Pages.
Dolomanov, et al. (2009) J. Appl. Cryst., 42: 339-341.

(56) References Cited

OTHER PUBLICATIONS

Dost, J. et al., "Preparation of 1,3,4,-Oxadiazol-2-carboxylic Acid Derivatives", *J. Prakt. Chem.*, v. 327, n. 1, p. 109-116 (1985).
Dredge, K., et al., "PG545, a dual heparanase and angiogenesis inhibitor, induces potent anti-tumour and anti-metastatic efficacy in preclinical models", British Journal of Cancer v. 104, p. 635-642 (2011).
Elkin, M. et al. "Heparanase as mediator of angiogenesis: mode of action", FASEB J., v. 15, n. 9, p. 1661-3 (2001).
Ferro et al, "Discovery of PG545: A Highly Potent and Simultaneous Inhibitor of Angiogenesis, Tumor Growth, and Metastasis", Journal of Medicinal Chemistry (2012), vol. 55, pp. 3804-3813.
Forest et al. (2015) Disease Models and Mechanisms, 8: 421-427.
Francis, J.E., et al., "Structure-Activity Profile of a Series of Novel Triazoloquinazoline Adenosine Antagonists", J. Med. Chem. v. 31, p. 1014-1020 (1988).
Freeman (1997) *Biochem J*, 325: 229-237.
Freeman et al. (2005) *J Biol Chem*, 280(10): 8842-8849.
Gagliardi et al. (1998) *Cancer Chemother Pharmacol*, 41: 117-124.
Giardinà, D. et al., "Structure-Activity Relationships in Prazosin-Related Compounds. Effect of Replacing a Piperazine Ring with an Alkanediamine Moiety on $\alpha_1$-Adrenoreceptor Blocking Activity", J. Med. Chem., v. 32, n. 1 (1989).
Gonzalez et al., "Demonstration of Inhibiory Effect of Oral Shark Cartilage on Basic Fibroblast Growth Facotr-Induced Angiogenesis in the Rabbit Cornea", Biol Pharm Bull, v. 24, No. 2, p. 151-154 (2001).
Gozalbes et al. (2013) *Bioorg Med Chem*, 21(7): 1944-1951.
Grzyb, J.Z., "Carbamoylimidazolium and thiocarbamoylimidazolium salts: novel reagents for the synthesis of ureas, thioureas, carbamates, thiocarbamates and amides", Tetrahedron, v. 61, n. 30, p. 7153 (2005).
Guo et al. (2017) *Veterinary Microbiology*, 201: 231-239.
Gutter-Kapon, L., et al., "Heparanase is required for activation and function of macrophages", PNAS, v. 113, n. 48, p. E7808-E7817 (Nov. 29, 2016).
Häcker, H-G et al, "Analogs of a 4-Aminothieno[2,3-d] Pyrimidine Lead (QB13) as Modulators of P-Glycoprotein Substrate Specificity" Bioorganic & Med. Chem. Letters, v. 19, p. 6102-6105 (2009).
Hammond, E., et al., "Development of a colorimetric assay for heparanase activity suitable for kinetic analysis and inhibitor screening", *Anal Biochem.*, v. 396, p. 112-116 (2010).
Hammond et al. (2013) FEBS Open Bio, 3: 346-351.
He, et al, "Hypoxia Increases Heparanase-Dependent Tumor Cell Invasion, Which Can be Inhibited by Antiheparanase Antibodies", Cancer Research (2004), vol. 64, pp. 3928-3933.
Ilan, N., et al. "Regulation, function and clinical significance of heparanase in cancer metastasis and angiogenesis", Int. J. Biochem. Cell Biol. 38, 2018-39 (2006).
Ishai-Michaeli, R. et al, "Heparanase activity expressed by platelets, neutrophils, and lymphoma cells releases active fibroblast growth factor from extracellular matrix", Cell Regul. Oct. 1990; 1(11): 833-842.
Ishida et al. (2004) *J Antibiot* (Tokyo), 57: 136-142.
Ishida et al. (2004) Mol Cancer Ther, 3(9): 1069-1077.
Ishida et al. (2004) *Chem Biol*, 11(3): 367-377.
Janik-Papis, K., et al., "Role of oxidative mechanisms in the pathogenesis of age-related macular degeneration", Klinika Oczna, v. 111, n. 4-6, p. 168-173 (2008).
Jiang, et al. (2015) Curr Eye Res, 40(8): 761-771.
Josefsen, K., et al., "Fluorescence-activated cell sorted rat islet cells and studies of the insulin secretory process", J. Endocrinol., v. 149, n. 1, p. 145-154 (1996).
Jyothirmayi, G., et al, "Doxazosin Prevents Proteinuria and Glomerular Loss of Heparan Sulfate in Diabetic Rats", Hypertension, v. 27, n. 5, p. 1108-1114 (1996).
Karamichos, et al. (2012) J Funct Biomater, 3(4): 760-775.
Karoli et al. (2005) *J Med Chem*, 48(26): 8229-8236.
Kawase et al. (1996) *J Antibiot* (Tokyo), 49(1): 61-64.
Kirschfink (2003) Clin Vaccine Immunol, 10(6): 982-989.

Klauser et al. "*Biochemical studies on sulfated lactobionic acid amides*", (1991) *Semin Thromb Hemost*, 17(Suppl 1): 118-125.
Klein, R., et al., "The Wisconsin Epidemiologic Study of Diabetic Retinopathy a Comparison of Retinopathy in Younger and Older Onset Diabetic Persons", Adv. Exp. Med. Biol., v. 189, p. 321-335 (1985).
Klein, R., et al., "Prevalence of age-related macular degeneration in the US population", Arch Ophthalmol., v. 129, n. 1, p. 75-80 (Jan. 2011).
Knickelbein, J.E., et al., "Inflammatory Mechanisms of Age-related Macular Degeneration", Int. Ophthalmol. Clin., v. 55, n. 3, p. 63-78 (2015).
Ko et al. (2000) *J Antibiot* (Tokyo), 53(2): 211-214.
Kumagai, et al, "Sodium pentosan polysulfate resulted in cartilage improvement in knee osteoarthritis—An open clinical trial-", BMC Clinical Pharmacology (2010), vol. 10, No. 1, Article 7, 9 Pages.
Lafond, et al. (2017) Expert Opinion on Drug Delivery, 14(4): 539-550.
Laha, J.K. et al., "Palladium-catalyzed regioselective C-2 arylation of 7-azaindoles, indoles, and pyrroles with arenes" Chem. Commun., v. 52, p. 4329-4332 (2016).
Lapierre et al. (1996) *Glycobiology*, 6(3): 355-366.
Lee, R., et al., "Epidemiology of diabetic retinopathy, diabetic macular edema and related vision loss", Eye and Vis (Lond), 2:17 (2015).
Lee, S.J. et al., "Discovery of Potent Cyclic GMP Phosphodiesterase Inhibitors. 2-Pyridyl- and 2-Imidazolylquinazolines Possessing Cyclic GMP Phosphodiesterase and Thromboxane Synthesis Inhibitory Activities", *J Med Chem*. 1995, 38 (18), pp. 3547-3557.
Levidiotus et al. (2004) *J Am Soc Nephrol*, 15(1): 68-78.
Li, L., et al., "The microglia in healthy and diseased retina", Exp Eye Res., v. 136, p. 116-130, Jul. 2015.
Liu, M. et al., "Evaluation of the Antitumor Efficacy of RNAi-Mediated Inhibition of CDC20 and Heparanase in an Orthotopic Liver Tumor Model", Cancer Biother. Radiopharm. 30, 233 9 (2015).
Ma et al, "Phosphomannopentaose sulfate (PI-88) inhibits retinal leukostasis in diabetic rat", Biochemical and Biophysical Research Communications, (2009), vol. 380, Issue 2, pp. 402-406.
Marchetti et al. (1997) J Biol Chem, 272(25): 15891-15897.
Marchetti et al. (2003) *Int J Cancer*, 104(2): 167-174.
Matera, R., "Design and Synthesis of Novel Non Peptidomimetic Beta-Secretase Inhibitors in the Treatment of Alzheimer's Disease", Doctoral Research, Universita di Bologna (2009).
McKenzie, E.A.., "Heparanase: a target for drug discovery in cancer and inflammation", *Br. J. Pharmacol*. May 2007; 151(1): 1-14.
Mi et al. (2014) Drug Des Devel Ther, 8: 2311-2319.
MINTEL GNPD, "Dry Eye Lubricant Eye Drops", Available from the Internet, <URL http://www.gnpd.com/sinatra/recordpage/1877871/ >, Published Sep. 2012 according to MINTEL GNPD.
Mitragotri (2005) Nat Rev Drug Discov, 4: 255-260.
Moreno, E. et al., "Sulfur and selenium derivatives of quinazoline and pyrido[2,3-d]pyrimidine: Synthesis and study of their potential cytotoxic activity in vitroSulfur and selenium derivatives of quinazoline and pyrido[2,3-d]pyrimidine: Synthesis and study of their potential cytotoxic activity in vitro", Eur. J. of Med Chem., v. 47, p. 283-298, (Jan. 2012).
Myler et al. (2006) J Biochem, 139(3): 339-345.
Naggi et al. (2005) *J Biol Chem*, 280(13): 12103-12113.
Naik N., et al., "Novel Indole-2-Carboxylic Acid Analogues: Synthesis and a New Light in to their Antioxidant Potentials", Eur. J. Chem., 3(2), 214 (2012).
Natoli, et al. (2008) Mol Vis, 14: 1983-1994.
Natoli, et al. (2016) Exp Eye Res, 147: 114-127.
Ni et al. (2016) Molecules, 21(11): 1602.
Nishimura et al. (2000) *J Org Chem*, 65(1): 2-11.
Niu et al. (2015) Carbohydrate Polymers, 125: 76-84.
Nugent, J. et al., "Solvent-Free Synthesis of Cyanoformamides from Carbamoyl Imidazoles", Eur. J. Org. Chem., v. 2017, n. 34, p. 5110-5118 (2017).

(56) References Cited

OTHER PUBLICATIONS

O'Koren, E.G., et al., "Fate mapping reveals that microglia and recruited monocyte-derived macrophages are definitively distinguishable by phenotype in the retina", Sci. Rep., 6. art. No. 20636 (2016).
Pan et al. (2006) *Bioorg Med Chem Lett*, 16(2): 409-412.
Pangborn A., et al., "Safe and Convenient Procedure for Solvent Purification", *Organometallics*, v. 15, n.5 p. 1518 (1996).
Papadopoulos, et al. (2012) Angiogenesis, 15(2): 171-185.
Parish et al. (1999) Cancer Res, 59: 3433-3441.
Parish, C.R., "The role of heparan sulphate in inflammation", Nat. Rev. Immuno., v. 6, p. 633-643 (2006).
Pazdera, P. et al. "Preparation and cyclization of 3-substituted 1-(2-cyanophenyl)-thioureas" Chemical Papers (1989) vol. 43( 6) p. 77 1-781.
Pennisi, et al. (2012) Mol Aspects Med, 33(4): 487-509.
Perez-Balbuena et al, "Efficacy of a fixed combination of 0.09 % xanthan gum/0.1 % chondroitin sulfate preservative free vs polyethylene glycol/propylene glycol in subjects with dry eye disease: a multicenter randomized controlled trial", BMC Ophthalmology (2016), vol. 16, p. 164, 6 Pages, Published Sep. 20, 2016.
Pfeiffer, W-D, et al., "Synthesis and Reactivity of 1,2,4-Triazolo{1,5-c] Quinazolines", J. Heterocyclic Chem., v. 36, p. 1327 (1999).
Rangasamy, S., et al., "Chemokine mediated monocyte trafficking into the retina: role of inflammation in alteration of the blood-retinal barrier in diabetic retinopathy", PLoS One, v. 9, n. 10, e108508 (Oct. 20, 2014).
Rezzola et al. (2014) Angiogenesis, 17(3): 429-442.
Rivara, S., et al., "Heparanase: a rainbow pharmacological target associated to multiple pathologies including rare diseases", Future Med Chem., v. 8, n. 6, p. 647-680 (2016).
Robaa, Dina, et al. "Identification and Structure-Activity Relationship Studies of Small-Molecule Inhibitors of the Methyllysine Reader Protein Spindlin1." ChemMedChem, (2016) vol. 11(20) pp. 2327-2338 X compound le, p. 2336.
Robertson, W.M., et al, "Synthesis and evaluation of a series of C5'-substituted duocarmycin SA analogs", Bioorg. Med. Chem. Lett., v. 20, p. 2722 (2010).
Roy et al. (2014) *J Med Chem*, 57(11): 4511-4520.
Rutar, M., et al., "Brief Exposure to Damaging Light Causes Focal Recruitment of Macrophages, and Long-Term Destabilization of Photoreceptors in the Albino Rat Retina", Curr. Eye Res., v. 35, n. 7, p. 631-643 (2010).
Rutar, M., et al. (2011) Invest Ophthalmol Vis Sci, 52: 5347-5358.
Rutar, M., et al., "Small interfering RNA-mediated suppression of Ccl2 in Müller cells attenuates microglial recruitment and photoreceptor death following retinal degeneration", *J. Neuroinflammation*, v. 9, n 1, p. 221 (2012).
Rutar, M., et al. (2014) PLoS One, v. 9, n. 4: e93343.
Saiki et al. (1990) *Cancer Res*, 50: 3631-3637.
Schröder, S., et al., "Activated monocytes and granulocytes, capillary nonperfusion, and neovascularization in diabetic retinopathy", Am. J. Pathol., v. 139, n. 1, p. 81-100 (1991).
Seijas, J. A., et al., "Microwave enhanced synthesis of 4-aminoquinazolines", Tetrahedron Letters, v. 41, iss. 13, p. 2215-2217 (2000Seijas J. A et al. (Tetrahedron Lett. 2000, 41, 2215-2217).

Sheldrick, (2015) Acta Cryst., A71: 3-8.
Shelley et al. (2009) Arch Ophthalmol, 127: 483-492.
Shiozawa et al. (1995) J Antibiot (Tokyo), 48(5): 357-362.
Smits, R.A., et al., "Discovery of Quinazolines ad Histamine $H_4$ Receptor Inverse Agonists Using a Scaffold Hopping Approach", J. Med. Chem. v. 51, p. 7855-7865 (2008).
Song et al, "Effect of sulodexide in patients with non-proliferative diabetic retinopathy: diabetic retinopathy sulodexide study (DRESS)", Graefe's Archive for Clinical and Experimental Ophthalmology (2015), vol. 253, pp. 829-837.
Still, W.C., et al., "Rapid chromatographic technique for preparative separations with moderate resolution", J. Org. Chem., v. 43, n. 14, p. 2923 (1978).
Suhara et al. (1996) *Tetrahedron Letters*, 37(10): 1575-1578.
Suhara et al. (1996) *Tetrahedron Letters*, 37(15): 2549-2552.
Suhara et al. (2002) *Bioorg Med Chem*, 10(6): 1999-2013.
Takahashi et al. (2001) *Tetrahedron*, 57(32): 6915-6926.
Temkin et al. (2004) *J Allergy Clin Immunol*, 113(4): 703-709.
Tressler et al. (1996) In Molecular, Cellular, and Clinical Aspects of Angiogenesis, Plenum Press New York, p. 199.
Trost, B.M. et al., "A Stereodivergent Strategy to Both Product Enantiomers from the Same Enantiomer of a Stereoinducing Catalyst: Agelastatin A", Chem. Euro. J., v. 15, n, 28, p. 6910 (2009).
Van Lookeren Campagne, M., et al., "Mechanisms of age-related macular degeneration and therapeutic opportunities", J. Pathol., v. 232, n. 2, p. 151-164 (2014).
Watterson, S.H., et al., "Potent and Selective Agonists of Sphingosine 1-Phosphate 1 (S1P1): Discovery and SAR of a Novel Isoxazole Based Series", J. of Med. Chem., v. 59, n. 6, p. 2820-2840 (2016).
Weissman et al. (2016) *PNAS*, 113(3): 704-709.
Xu et al. (2006) *Bioorg Med Chem Lett*, 16(2): 404-408.
Yang et al. (2009) *Cancer Immunol Immunother*, 58(9): 1387-1396.
Zammit et al. (2007) *Org Biomol Chem*, 5: 2826-2834.
Zderic, et al. (2004) J Ultrasound Med, 23: 1349-1359.
Zetser et al. (2004) *Journal of Cell Science*, 117: 2249-2258.
Zhenhua, L., et al., "Facile and Efficient Cyclization of Anthranilonitrile to 2,4-Dichloroquinazoline by Bis(trichloromethyl) Carbonate and Catalytic Amount Triphenylphosphine Oxide", Heterocycles,, v. 85, n. 6, p. 1417-1426 (2012).
Zhong, et al. (2012) Heterocycles, 85: 1417-1426.
Ziolkowski et al. (2012) *J Clin Invest*, 122(1): 132-141.
U.S. Appl. No. 16/475,671, filed Jul. 2, 2019.
U.S. Appl. No. 16/475,669, filed Jul. 2, 2019.
CAS Registry No. 1347928-14-6; STN Entry Date Dec. 4, 2011; 2-Furancarboxamide, N-[3-[[6,7-dimethoxy-4-(methylamino)-2-quinazolinyl]amino]propyl]tetrahydro.
CAS Registry No. 1319000-50-4; STN Entry Date Aug. 17, 2011; Benzamide, N-[2-[(4-amino-6,7-dimethoxy-2-quinazolinyl)amino]ethyl]-3-fluoro-4-methyl.
CAS Registry No. 1317535-37-7; STN Entry Date Aug. 14, 2011; Benzamide, N-[2-[(4-amino-6,7-dimethoxy-2-quinazolinyl)amino]ethyl]-4-(trifluoromethyl).
Australian Application No. 2017376817, Examination Report dated Mar. 10, 2022.

\* cited by examiner

HEPARANASE INHIBITORS AND USE THEREOF

RELATED APPLICATIONS

This application is a U.S. National Phase of International Application No. PCT/AU2017/000270 filed Dec. 13, 2017 titled "Heparanase inhibitors and use thereof" which claims priority from U.S. Provisional Patent Application Ser. No. 62/433,652 filed 13 Dec. 2016 titled "Heparanase inhibitors and use thereof", and Australian Provisional Patent Application No 2017902346 filed 20 Jun. 2017, titled "Methods of treating ocular disorders", the entire contents of which are hereby incorporated by cross reference.

FIELD OF THE INVENTION

The present invention broadly relates to functionalised quinazoline compounds, pharmaceutical compositions comprising such compounds, and the use of such compounds as heparanase inhibitors for the treatment of a disease or condition related to heparanase activity. The invention further relates to processes for preparing the compounds.

BACKGROUND OF THE INVENTION

Heparanase is an endo-β-glucuronidase enzyme that is implicated in a wide variety of inflammatory and proliferative diseases, including Type 1 diabetes, Type 2 diabetes, diabetic nephropathy, nephritis, glomerulonephritis, and other cell-mediated autoimmune inflammation indications, cancer, allergy, dermatitis/psoriasis, macular degeneration, retinitis pigmentosa, pancreatitis, among others. Therefore, a drug that inhibits heparanse may be useful in the treatment of those diseases.

One example of a heparanase mediated disease is Type 1 diabetes. Type 1 diabetes is an autoimmune disease in which the insulin-producing beta cells of the Islets of Langerhans in the pancreas are destroyed by the body's immune cells, particularly T-cells. A major effect of this is lack of production of the hormone insulin, leading to abnormally high sugar levels in the blood (hyperglycaemia). While insulin therapy protects Type 1 diabetes patients from dying from diabetic coma, precise and sustained control of blood sugar levels is rarely, if ever, achieved. Over time, the resulting fluctuations in blood sugar levels lead to severe secondary blood vessel complications and disorders, which can result in kidney disease, heart disease, blindness, nerve damage (neuropathy), gangrene and stroke.

Type 1 diabetes affects 10-15% of people with diabetes and the incidence of Type 1 diabetes is also on the rise. In the period 1999-2005 the rate of new cases in those aged 0-14 increased by 25% (18.1 up to 22.6 per 100,000). The overall level of diabetes has a substantial impact on healthcare costs with the direct healthcare expenditures. There is currently no treatment available that can prevent or modify the progression of Type 1 diabetes. Given the seriousness of the disease, there is an urgent need for therapeutic drugs that mitigate the disease processes that lead to Type 1 diabetes.

Recent studies have demonstrated that insulin-producing islet beta cells unconditionally require the glycosaminoglycan polysaccharide heparan sulfate (HS) for their survival. HS is found in the extracellular matrix. HS chains matured by modifications such as deacetylation and sulfation can interact with a variety of secreted and transmembrane proteins, allowing signalling between cells.

The inventors have found that the normal HS content of islet beta cells is severely compromised and ultimately ablated during Type 1 diabetes onset/progression and during the isolation of islets for transplantation, which is a known treatment for Type 1 diabetes. The HS-degrading enzyme, heparanase (HPSE), a glycoside hydrolase that breaks down HS, plays a previously unrecognised role in the autoimmune destruction of islet cells in the development of Type 1 diabetes in mice. HPSE is produced predominantly by inflammatory cells present or infiltrating the islets.

The degradation of HS by HPSE also activates signal cascades that increase cell growth, mobility and angiogenesis. (Ishai-Michaeli, et al. Heparanase activity expressed by platelets, neutrophils, and lymphoma cells releases active fibroblast growth factor from extracellular matrix. *Cell Regul.* 1, 833-42 (1990). Elkin, M. et al. Heparanase as mediator of angiogenesis: mode of action. *FASEB J.* 15, 1661-3 (2001). HPSE is also required for inflammatory and immune cells to cross basement membrane of blood vessel cell wall (Parish C R, The role of heparan sulfate in inflammation. *Nat. Rev. Immunol.* 6, 633-43 (2006)). Hence HPSE is upregulated in tumour and cancer cells, where its overexpression has been strongly correlated with metastasis and increased mortality. (Ilan, N., et al. Regulation, function and clinical significance of heparanase in cancer metastasis and angiogenesis. *Int. J. Biochem. Cell Biol.* 38, 2018-39 (2006)). A clear link has now been established between heparanase expression and the process of tumourigenesis in a wide range of cancers, including bladder, brain, breast, colon, gastric, oral, oesophageal, pancreatic, prostate, thyroid and acute myeloid leukemia. (McKenzie, E. A. *Br J Pharmacol.* 2007 May; 151(1): 1-14). Inhibition of HPSE has also been shown to have a significant anti-tumor and anti-metastatic effect and HPSE is a well-characterised drug target in oncology. (Dredge, K. et al. PG545, a dual heparanase and angiogenesis inhibitor, induces potent anti-tumour and anti-metastatic efficacy in preclinical models. *Br. J. Cancer* 104, 635-42 (2011). Liu, M. et al. Evaluation of the Antitumor Efficacy of RNAi-Mediated Inhibition of $CDCl_2O$ and Heparanase in an Orthotopic Liver Tumor Model. *Cancer Biother. Radiopharm.* 30, 233-9 (2015)).

Three HPSE-inhibiting drugs have been assessed in clinical trials. Two of these, namely PI-88 and ST0001, have been shown to have significant efficacy in preclinical models of Type 1 diabetes, diabetic nephropathy and nephritis. However, all three HPSE inhibitors currently in development have potential safety issues that have adversely impacted their ability to be used as effective therapeutic agents. For example, PI-88 (Muparfostat, Progen Pharmaceuticals) which is a non-cleavable competitive inhibitor of heparanase, has poor efficacy as a therapeutic agent due to a number of factors, including an anti-coagulant activity that can result in uncontrolled bleeding. In addition, PI-88 also has a short half-life of approximately 30 minutes and also binds other proteins including Platelet Factor 4, which can give rise to heparin-induced thrombocytopenia.

Another inflammatory condition with increasing prevalence and incidence is age-related macular degeneration (AMD). Anti-VEGF agents are currently used in the management of many retinal disorders, especially those in which neovascularization is the primary pathology, including wet or exudative AMD. Several investigational anti-VEGF drugs have received FDA approval for use in treating AMD and related ocular conditions in humans, including pegaptanib sodium (Macugen, Pfizer Inc., New York, N.Y., USA), ranibizumab (Lucentis, Genentech, San Francisco, Calif., USA), aflibercept (Eylea, Regeneron Pharmaceuticals, Tarrytown, N.Y., USA) and bevacizumab (Avastin, Roche). Anti-VEGF intravitreal injections have dramatically altered the prognosis of AMD and improved chances of preserving useful vision in afflicted patients. However, whilst VEGF inhibitors are efficacious in advanced and late stages of AMD, currently there is no known treatment for early stage AMD.

There remains a need for alternative therapies, preferably small molecule drugs, for treating inflammatory diseases and disorders.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps. The term "consisting of" means "consisting only of", that is, including and limited to the stated element(s), integer(s) or step(s), and excluding any other element(s), integer(s) or step(s). The term "consisting essentially of" means the inclusion of the stated element(s), integer(s) or step(s), but other element(s), integer(s) or step(s) that do not materially alter or contribute to the working of the invention may also be included.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this specification.

SUMMARY OF THE INVENTION

The present inventors have identified small molecule heparanase inhibitors suitable for use in the treatment of a variety of conditions related to heparanase activity.

A first aspect of the invention relates to a compound of general formula (I)

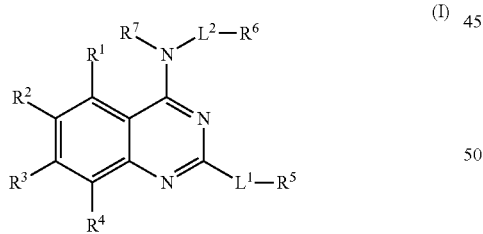

(I)

or a salt, hydrate, solvate, tautomer or stereoisomer thereof,
wherein:
$R^1$ is selected from H, hydroxyl, halo, $C_{1-6}$ alkyl, $C_{1-4}$ alkoxy, O—$CH_2$phenyl, O-phenyl;
$R^2$ is selected from H, hydroxyl, halo, $C_{1-6}$ alkyl, $C_{1-4}$ alkoxy, O—$CH_2$phenyl, O-phenyl;
$R^3$ is selected from H, hydroxyl, halo, $C_{1-6}$ alkyl, $C_{1-4}$ alkoxy, O—$CH_2$phenyl, O-phenyl;
$R^4$ is selected from H, hydroxyl, halo, $C_{1-6}$ alkyl, $C_{1-4}$ alkoxy, O—$CH_2$phenyl, O-phenyl;
or $R^1$ and $R^2$, or $R^2$ and $R^3$, or $R^3$ and $R^4$ together form $C_{1-3}$alkylenedioxy;

$L^1$ is selected from $C_{6-10}$ aryl, NH, NH$C_{1-4}$alkyl, NH$C_{1-4}$alkyl-NHC(O)—, NH$C_{1-4}$alkyl-NHSO$_2$—, azetidinyl-NHC(O)—, azetidinyl-NHSO$_2$—, N($C_{1-4}$alkyl)$_2$ wherein each alkyl is the same or different and is optionally substituted with a halo or hydroxyl group, or $L^1$ is absent;
$R^5$ is selected from H, halo, hydroxyl, $C_{1-6}$ alkyl, $C_{1-6}$ alkenyl, $C_{1-6}$ alkynyl, $C_{3-6}$ cycloalkyl, $C_{6-10}$ aryl optionally substituted with 1 or 2 $R^X$ groups, $C_{2-9}$ heteroaryl optionally substituted with 1 or 2 $R^X$ groups, heterocycloalkyl optionally substituted with 1 or 2 $R^X$ groups, alkylheterocycloalkyl optionally substituted with 1 or 2 $R^X$ groups, C(O)-heterocycloalkyl optionally substituted with 1 or 2 $R^X$ groups, NHC(NH)NR'R" (wherein R' and R" are independently selected from H and $C_{1-3}$alkyl), NHC(O)NR'R" (wherein R' and R" are independently selected from H and $C_{1-3}$alkyl), or $R^5$ is absent;
$L^2$ is selected from $C_{1-4}$ alkyl, azetidinyl-C(O)—, $C_{1-4}$alkyl-NHSO$_2$—, —C(O)—, —SO$_2$—; or $L^2$ is absent;
$R^6$ is selected from H, $C_{1-6}$ alkyl, guanidinyl, NHC(NH)NH($C_{1-3}$alkyl), ureido, NHC(O)NH($C_{1-3}$alkyl), $C_{6-10}$ aryl optionally substituted with 1 or 2 $R^X$ groups, $C_{1-9}$ heteroaryl optionally substituted with 1 or 2 $R^X$ groups, $C_{2-5}$ heterocycloalkyl optionally substituted with 1 or 2 $R^X$ groups, $C_{3-6}$cycloalkyl optionally substituted with 1 or 2 $R^X$ groups;
$R^7$ is H or $C_{1-6}$ alkyl;
or when $L^2$ is absent $R^6$ and $R^7$ together with the nitrogen to which they are attached form a heterocycloalkyl ring optionally substituted with 1 or 2 $R^X$ groups;
each $R^X$ is independently selected from hydroxyl, halo, nitro, NR'R" (wherein R' and R" are independently selected from H and $C_{1-3}$alkyl), $C_{1-4}$ alkyl, $C_{3-6}$cycloalkyl, C(O)$C_{1-3}$alkyl, C(O)O$C_{1-4}$alkyl, C(O)NHR$^Y$, $C_{6-10}$aryl optionally substituted with 1 or 2 $R^Y$ groups, $C_{2-9}$heteroaryl optionally substituted with 1 or 2 $R^Y$ groups, $C_{1-4}$alkyl-($C_{2-9}$heteroaryl), $C_{2-5}$heterocycloalkyl optionally substituted with 1 or 2 $C_{1-4}$ alkyl groups, $C_{1-4}$alkyl-($C_{2-5}$heterocycloalkyl) optionally substituted with 1 or 2 $C_{1-4}$ alkyl groups, C(O)—$C_{2-9}$heteroaryl optionally substituted with 1 or 2 $C_{1-4}$ alkyl groups; SO$_2$—$C_{2-9}$heteroaryl optionally substituted with 1 or 2 $C_{1-4}$ alkyl groups, or halo$C_{1-4}$ alkyl groups; or two adjacent $R^X$ groups together form $C_{1-3}$alkylenedioxy;
$R^Y$ is selected from H, hydroxyl, halo, $C_{1-4}$ alkyl, halo$C_{1-4}$ alkyl, $C_{1-4}$ alkoxy.

In preferred embodiments each heteroaryl and each heterocycloalkyl group has at least one nitrogen heteroatom.

In a second aspect the invention relates to a pharmaceutical composition comprising a compound of formula (I), or a salt, hydrate, solvate, tautomer or stereoisomer thereof, together with one or more pharmaceutically acceptable carriers, diluents or excipients.

Compounds of general formula (I) according to the present invention are heparanase inhibitors and the invention also relates to the treatment of diseases or conditions involving heparanase activity. Accordingly, another aspect of the present invention relates to a method of treatment of a disease or condition associated with heparanase activity in a subject, the method comprising administering to the subject an effective amount of a compound of formula (I) or a salt, hydrate, solvate, tautomer or stereoisomer thereof according to the first aspect of the invention, or a pharmaceutical composition according to the second aspect of the invention.

In a further aspect the present invention relates to the use of a compound of formula (I) or a salt, hydrate, solvate, tautomer or stereoisomer thereof according to the first aspect of the invention or a pharmaceutical composition according to the second aspect of the invention in the manufacture of a medicament for treating a disease or condition associated with heparanase activity.

In another aspect the present invention relates to the use of a compound of formula (I) or a salt, hydrate, solvate, tautomer or stereoisomer thereof according to the first aspect of the invention or a pharmaceutical composition according to the second aspect of the invention for the treatment of a disease or condition associated with heparanase activity in a subject.

In a preferred embodiment, the treatment of disease by compounds of formula (I) involves at least heparanase inhibition.

In preferred embodiments the disease or condition associated with heparanase activity is selected from Type 1 diabetes, Type 2 diabetes, nephritis, glomerulonephritis, cell-mediated autoimmune inflammation, diabetic nephropathy, gestational diabetes, diabetic ketoacidosis, hyperglycemia, hyperosmolar state, hypoglycemia, diabetic coma, diabetic cardiomyopathy, diabetic neuropathy, diabetic foot, diabetic retinopathy, diabetic myonecrosis, diabetic encephalopathy, and an ocular inflammatory disorder. In other preferred embodiments the disease or condition is selected from Type 1 diabetes, Type 2 diabetes, diabetic nephropathy, nephritis, glomerulonephritis, and cell-mediated autoimmune inflammation indications involving heparanase. In particularly preferred embodiments the disease or condition is selected from Type 1 diabetes and Type 2 diabetes. In other preferred embodiments the disease or condition is selected from Type 1 diabetes, Type 2 diabetes, diabetic nephropathy, nephritis, glomerulonephritis, and cell-mediated autoimmune inflammation indications involving heparanase. In other preferred embodiments the disease or condition is an ocular inflammatory disorder. In particularly preferred embodiments the disease or condition is selected from Type 1 diabetes and Type 2 diabetes.

In other embodiments the disease or condition related to heparanase activity is selected from cancer, allergies, dermatitis, psoriasis, macular degeneration, retinitis pigmentosa, and pancreatitis.

Other aspects and embodiments of the present invention relate to processes for preparing compounds of the invention as disclosed herein.

Definitions

The following are some definitions of terms used in the art that may be helpful in understanding the description of the present invention. These are intended as general definitions and should in no way limit the scope of the present invention to those terms alone, but are put forth for a better understanding of the following description.

Unless the context requires otherwise or specifically stated to the contrary, integers, steps, or elements of the invention recited herein as singular integers, steps or elements clearly encompass both singular and plural forms of the recited integers, steps or elements.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps, features, compositions and compounds.

In the context of this specification the term "alkyl" includes within its meaning monovalent ("alkyl") and divalent ("alkylene") straight chain or branched chain saturated aliphatic groups having from 1 to 6 carbon atoms, denoted $C_{1-6}$alkyl. The alkyl group may be $C_{1-4}$alkyl. The alkyl group may be $C_{1-3}$alkyl. The alkyl group may be $C_{1-2}$alkyl. Thus, for example, the term alkyl includes, but is not limited to, methyl, ethyl, 1-propyl, isopropyl, 1-butyl, 2-butyl, isobutyl, tert-butyl, amyl, 1,2-dimethylpropyl, 1,1-dimethylpropyl, pentyl, isopentyl, hexyl, 4-methylpentyl, 1-methylpentyl, 2-methylpentyl, 3-methylpentyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, and the like.

In the context of this specification the term "alkenyl" includes within its meaning monovalent ("alkenyl") and divalent ("alkenylene") straight or branched chain unsaturated aliphatic hydrocarbon groups having from 2 to 6 carbon atoms and at least one double bond anywhere in the chain, denoted $C_{2-6}$alkenyl. The alkenyl group may be $C_{2-4}$ alkenyl. The alkenyl group may be $C_{2-3}$ alkenyl. Unless indicated otherwise, the stereochemistry about each double bond may be independently cis or trans, or E or Z as appropriate. Examples of alkenyl groups include but are not limited to ethenyl, vinyl, allyl, 1-methylvinyl, 1-propenyl, 2-propenyl, 2-methyl-1-propenyl, 2-methyl-1-propenyl, 1-butenyl, 2-butenyl, 3-butenyl, 1,3-butadienyl, 1-pentenyl, 2-pentenyl, 3-pentenyl, 4-pentenyl, 1,3-pentadienyl, 2,4-pentadienyl, 1,4-pentadienyl, 3-methyl-2-butenyl, 1-hexenyl, 2-hexenyl, 3-hexenyl, 1,3-hexadienyl, 1,4-hexadienyl, 2-methylpentenyl, and the like.

In the context of this specification the term "alkynyl" includes within its meaning monovalent ("alkynyl") and divalent ("alkynylene") straight or branched chain unsaturated aliphatic hydrocarbon groups having from 2 to 6 carbon atoms and having at least one triple bond, denoted $C_{2-6}$alkynyl. The alkynyl group may be $C_{2-4}$alkynyl. The alkyl group may be $C_{2-3}$alkynyl. Examples of alkynyl groups include but are not limited to ethynyl, 1-propynyl, 1-butynyl, 2-butynyl, 1-methyl-2-butynyl, 3-methyl-1-butynyl, 1-pentynyl, 1-hexynyl, methylpentynyl, and the like.

In the context of this specification the term "alkoxy" refers to straight chain or branched alkoxy (O-alkyl) groups, wherein alkyl is as defined above. Examples include methoxy, ethoxy, n-propoxy, isopropoxy, sec-butoxy, tert-butoxy, and the like.

In the context of this specification the term "aryl" as a group or part of a group denotes (i) an optionally substituted monocyclic, or fused polycyclic, aromatic carbocycle (ring structure having ring atoms that are all carbon) that may have from 6-10 atoms per ring, denoted $C_{6-10}$aryl. Examples of aryl groups include phenyl, naphthyl, phenanthryl and the like; (ii) an optionally substituted partially saturated bicyclic aromatic carbocyclic moiety in which a phenyl and a $C_{5-7}$cycloalkyl or $C_{5-7}$cycloalkenyl group are fused together to form a cyclic structure, such as tetrahydronaphthyl, indenyl or indanyl. The group may be a terminal group or a bridging group.

In the context of this specification the term "cycloalkyl" refers to a saturated or partially saturated, monocyclic, fused or spiro polycyclic, carbocycle that may contain from 3 to 9 carbon atoms per ring, such as cyclopropyl, cyclobutyl, cyclopentyl, cyclohexyl, spiro[3.3]heptane, and the like, unless otherwise specified. It includes monocyclic systems such as cyclopropyl and cyclohexyl, bicyclic systems such as decalin, and polycyclic systems such as adamantane. The group may be a terminal group or a bridging group.

In the context of this specification the term "cycloalkenyl" means a non-aromatic monocyclic or multicyclic ring system containing at least one carbon-carbon double bond and may have from 5-10 carbon atoms per ring, denoted $C_{5-10}$ cycloalkenyl. Exemplary monocyclic cycloalkenyl rings include cyclopentenyl, cyclohexenyl or cycloheptenyl. The cycloalkenyl group may be substituted by one or more substituent groups. The group may be a terminal group or a bridging group.

The term "$C_{1-3}$alkylenedioxy" as used herein refers to an —$O(CH_2)_{1-3}O$— group wherein the oxygen atoms of the alkylenedioxy group are attached to two adjacent carbon atoms of the parent molecular moiety forming a 5-, 6- or 7-membered ring. Exemplary alkylenedioxy groups are methylenedioxy and 1,2-ethylenedioxy.

In the context of this specification the terms "halogen" or "halo" are synonymous and refer to fluorine, chlorine, bromine or iodine.

In the context of this specification the term "heterocycloalkyl" includes within its meaning monovalent ("heterocycloalkyl") and divalent ("heterocycloalkylene"), saturated, monocyclic, bicyclic, fused or spiro polycyclic, hydrocarbon radicals having from 3 to 8 ring atoms, wherein from 1 to 5, or from 1 to 3, typically 1 or 2 ring atoms are heteroatoms independently selected from O, N, NH, or S. The heterocycloalkyl group may be $C_{3-6}$ heterocycloalkyl. The heterocycloalkyl group may be $C_{3-5}$heterocycloalkyl. Representative examples of heterocycloalkyl groups include aziridinyl, azetidinyl, pyrrolidinyl, piperidinyl, piperazinyl, quinuclidinyl, morpholinyl, diazaspiro[3.3]heptane (e.g., 2,6-diazaspiro[3.3]heptane), tetrahydrothiophenyl, tetrahydrofuranyl, tetrahydropyranyl, and the like. In one or more embodiments the heterocycloalkyl group is an N-heterocycloalkyl having one or more nitrogen heteroatoms, e.g., 1, 2, 3 or 4 nitrogen heteroatoms depending on the particular structure. N-heterocycloalkyl groups may also have heteroatoms other than nitrogen, but are characterized by having at least one nitrogen heteroatom. Exemplary N-heterocycloalkyl groups include aziridinyl, azetidinyl, pyrrolidinyl, piperidinyl, piperazinyl, morpholinyl, 2,6-diazaspiro[3.3]heptane among others. The heterocycloalkyl group may be a terminal group or a bridging group and may be attached through a heteroatom or any carbon ring atom.

In the context of this specification the term "heteroaryl" either alone or as part of a group means a monocyclic heteroaryl group having a 5- or 6-membered aromatic ring having one or more heteroatoms as ring atoms in the aromatic ring with the remainder of the ring atoms being carbon atoms, or a 8-10 membered bicyclic heteroaryl consisting of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The monocyclic heteroaryl and the bicyclic heteroaryl may be connected to the parent molecular moiety through any carbon atom or any nitrogen atom contained within the monocyclic heteroaryl or the bicyclic heteroaryl. Representative examples of monocyclic heteroaryl include, but are not limited to, furyl, imidazolyl, isoxazolyl, isothiazolyl, oxadiazolyl, oxazolyl (e.g., 1,3-oxazolyl, 1,2-oxazolyl), pyridinyl (e.g., 2-, 3-, 4-pyridinyl), pyridazinyl, pyrimidinyl, pyrazinyl, pyrazolyl, pyrrolyl, tetrazolyl, thiadiazolyl, thiazolyl, thienyl, triazolyl (e.g., 1,2,3-triazolyl, 1,2,4-triazolyl), and triazinyl. Representative examples of bicyclic heteroaryl include, but are not limited to, benzimidazolyl, benzofuranyl, benzothienyl, benzoxadiazolyl (e.g., 2,1,3-benzoxadiazolyl), cinnolinyl, dihydroquinolinyl, dihydroisoquinolinyl, furopyridinyl, indazolyl, indolyl (e.g, 2- or 3-indolyl), isoquinolinyl (e.g., 1-, 3-, 4-, or 5-isoquinolinyl), naphthyridinyl (e.g., 1,5-naphthyridinyl, 1,7-naphthyridinyl, 1,8-naphthyridinyl, etc), pyrrolopyridinyl (e.g., pyrrolo[2,3-b]pyridinyl), quinolinyl (e.g., 2-, 3-, 4-, 5-, or 8-quinolinyl), quinoxalinyl, tetrahydroquinolinyl, and thienopyridinyl. In one or more embodiments the heteroaryl group is an N-heteroaryl group having one or more nitrogen heteroatoms, e.g., 1, 2, 3 or 4 nitrogen heteroatoms depending on the particular structure. N-heteroaryl groups may also have heteroatoms other than nitrogen, but N-heteroaryl groups are characterized by having at least one nitrogen heteroatom. Exemplary N-heteroaryl groups include imidazolyl, indolyl, (e.g., 2- or 3-indolyl), naphthyridinyl, pyrazinyl, pyridyl (e.g., 2-, 3- or 4-pyridyl), pyrrolyl, pyrimidinyl, quinolinyl (e.g., 2-, 3-, 4-, 5-, or 8-quinolinyl), isoquinolinyl, quinazolinyl, quinoxalinyl, triazinyl, among others. The heteroaryl group may be a terminal group or a bridging group and may be attached through a heteroatom or any carbon ring atom.

The term "heteroatom" or variants such as "hetero-" as used herein refers to O, N, NH and S.

The term "inhibitor" as used herein refers to an agent that decreases, inhibits or impairs at least one function or biological activity of a target molecule. As used herein, the term "heparanase inhibitor" refers to an agent that decreases, inhibits or impairs at least one function or biological activity of heparanase. Heparanase inhibitors may decrease, inhibit or impair heparanase catalytic activity, heparanase protein binding, heparanase-mediated modulation of gene transcription, heparanase-mediated initiation of cell signaling and/or angiogenesis. In particular embodiments, the heparanase inhibitor decreases, inhibits or impairs one or more biological activities of heparanase, including heparanase catalytic activity. In particular embodiments, the heparanase inhibitor is an inhibitor of the type 1 heparanase isoform. The heparanase inhibitor may also inhibit complement fixation, macrophage activation, oxidative damage and/or growth factor activity. In preferred embodiments, the heparanase inhibitor inhibits one or both of macrophage, preferably microglial, activation and complement fixation. Heparanase inhibitors according of the present invention may be selective or non-selective inhibitors. In various embodiments, heparanase inhibitors according to the present invention are selective heparanase inhibitors.

The term "optionally substituted" as used throughout the specification denotes that the group may or may not be further substituted or fused (so as to form a polycyclic system), with one or more non-hydrogen substituent groups. Suitable chemically viable optional substituents for a particular functional group will be apparent to those skilled in the art. Typical optional substituents include $C_{1-4}$ alkyl, $C_{2-4}$ alkenyl, OH, halogen, O($C_{1-4}$ alkyl), CN, $NO_2$, NR'R" (wherein R' and R" are independently selected from H and $C_1$-$C_3$ alkyl); CONR'R" (wherein R' and R" are independently selected from H and $C_1$-$C_3$ alkyl), SH, S($C_{1-3}$ alkyl), $SO_2$($C_{1-3}$alkyl), $CH_2$—($C_{1-3}$alkoxy), $C_{1-3}$alkylenedioxy, $C_{6-10}$ aryl, —$CH_2$-phenyl, O—$CH_2$-phenyl, hydroxy($C_{1-3}$ alkyl), halo($C_{1-3}$alkyl), $CO_2H$, $CO_2$($C_{1-4}$ alkyl), among others. Presently preferred optional substituents include halogen, OH, $NH_2$, $C_{1-3}$ alkyl, $C_{1-3}$ alkoxy, —$CH_2$—($C_{1-3}$alkoxy), $CH_2OH$, halo-($C_{1-3}$)alkyl, e.g., $CF_3$, halo-($C_{1-3}$)alkoxy, e.g, $OCF_3$, phenyl, and —$CH_2$— phenyl.

Certain compounds of the disclosed embodiments may exist as single stereoisomers, racemates, and/or mixtures of enantiomers and/or diastereomers. All such single stereoisomers, racemates, enantiomers, diastereomers and mixtures thereof, are intended to be within the scope of the subject matter of the invention.

Additionally, general formula (I) is intended to cover, where applicable, solvated as well as unsolvated forms of the compounds. Thus, each formula includes compounds having the indicated structure, including the hydrated or solvated form, as well as the non-hydrated and non-solvated forms. The term "solvate" is used herein to describe a molecular complex comprising the compound of the invention and one or more pharmaceutically acceptable solvent molecules, for example, ethanol. The term "hydrate" is employed when the solvent is water.

The term "pharmaceutically acceptable salt" refers to those salts which, within the scope of sound medical judgement, are suitable for use in contact with the tissues of humans and animals without undue toxicity, irritation, allergic response and the like, and are commensurate with a reasonable benefit/risk ratio. Pharmaceutically acceptable salts are well known in the art. S. M. Berge et al. describe pharmaceutically acceptable salts in detail in J. Pharmaceutical Sciences, 1977, 66:1-19. For a review on suitable salts, see Handbook of Pharmaceutical Salts: Properties, Selection, and Use by Stahl and Wermuth (Wiley-VCH, 2002). Methods for making pharmaceutically acceptable salts of compounds of the invention are known to one of skill in the art. The salts can be prepared in situ during the final isolation and purification of the compounds of the invention, or separately by reacting the free base function with a suitable organic acid. Suitable pharmaceutically acceptable acid addition salts of the compounds of the present invention may be prepared from an inorganic acid or from an organic acid. Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, ascorbic, glucoronic, fumaric, maleic, pyruvic, alkyl sulfonic, arylsulfonic, aspartic, glutamic, benzoic, anthranilic, mesylic, methanesulfonic, salicylic, p-hydroxybenzoic, phenylacetic, mandelic, ambonic, pamoic, pantothenic, sulfanilic, cyclohexylaminosulfonic, stearic, algenic, β-hydroxybutyric, galactaric, and galacturonic acids. Suitable pharmaceutically acceptable base addition salts of the compounds of the present invention include metallic salts made from lithium, sodium, potassium, magnesium, calcium, aluminium, and zinc, and organic salts made from organic bases such as choline, diethanolamine, morpholine. Alternatively, suitable pharmaceutically acceptable base addition salts of the compounds of the present invention include organic salts made from N,N'-dibenzylethylenediamine, chloroprocaine, choline, diethanolamine, ethylenediamine, meglumine (N-methylglucamine), procaine, ammonium salts, quaternary salts such as tetramethylammonium salt, amino acid addition salts such as salts with glycine and arginine. In the case of compounds that are solids, it will be understood by those skilled in the art that the inventive compounds, agents and salts may exist in different crystalline or polymorphic forms, all of which are intended to be within the scope of the present invention and specified formulae.

The term "stereoisomer" as used herein refers to any two or more isomers that have the same molecular constitution and differ only in the three dimensional arrangement of their atomic groupings in space. Stereoisomers may be diastereoisomers or enantiomers. It will be recognized that the compounds described herein may possess asymmetric centers and are therefore capable of existing in more than one stereoisomeric form. The invention thus also relates to compounds in substantially pure isomeric form at one or more asymmetric centers e.g., greater than about 90% ee, such as about 95% or 97% ee or greater than 99% ee, as well as mixtures, including racemic mixtures, thereof. Such isomers may be naturally occurring or may be prepared by asymmetric synthesis, for example using chiral intermediates, or by chiral resolution.

The terms "treating", "treatment" and "therapy" are used herein to refer to curative therapy, prophylactic therapy, palliative therapy and preventative therapy. Thus, in the context of the present disclosure the term "treating" encompasses curing, ameliorating or tempering the severity of a medical condition or one or more of its associated symptoms.

The terms "therapeutically effective amount" or "pharmacologically effective amount" or "effective amount" refer to an amount of an agent sufficient to produce a desired therapeutic or pharmacological effect in the subject being treated. The terms are synonymous and are intended to qualify the amount of each agent that will achieve the goal of improvement in disease severity and/or the frequency of incidence over treatment of each agent by itself while preferably avoiding or minimising adverse side effects, including side effects typically associated with other therapies. Those skilled in the art can determine an effective dose using information and routine methods known in the art.

A "pharmaceutical carrier, diluent or excipient" includes, but is not limited to, any physiological buffered (i.e., about pH 7.0 to 7.4) medium comprising a suitable water soluble organic carrier, conventional solvents, dispersion media, fillers, solid carriers, coatings, antibacterial and antifungal agents, isotonic and absorption delaying agents. Suitable water soluble organic carriers include, but are not limited to, saline, dextrose, corn oil, dimethylsulfoxide, and gelatin capsules. Other conventional additives include lactose, mannitol, corn starch, potato starch, binders such as microcrystalline cellulose, cellulose derivatives such as hydroxypropylmethylcellulose, acacia, gelatins, disintegrators such as sodium carboxymethylcellulose, and lubricants such as talc or magnesium stearate.

"Subject" includes any human or non-human mammal. Thus, in addition to being useful for human treatment, the compounds of the present invention may also be useful for veterinary treatment of mammals, including companion animals and farm animals, such as, but not limited to dogs, cats, horses, cows, sheep, and pigs. In preferred embodiments the subject is a human.

In the context of this specification the term "administering" and variations of that term including "administer" and "administration", includes contacting, applying, delivering or providing a compound or composition of the invention to a subject by any appropriate means.

BRIEF DESCRIPTION OF THE DRAWINGS

FIG. 8 presents the efficacy of heparanase inhibitors in an in vivo mouse model of age-related macular degeneration induced by photo-oxidative damage.

DETAILED DESCRIPTION OF EMBODIMENTS OF THE INVENTION

Figure 1:
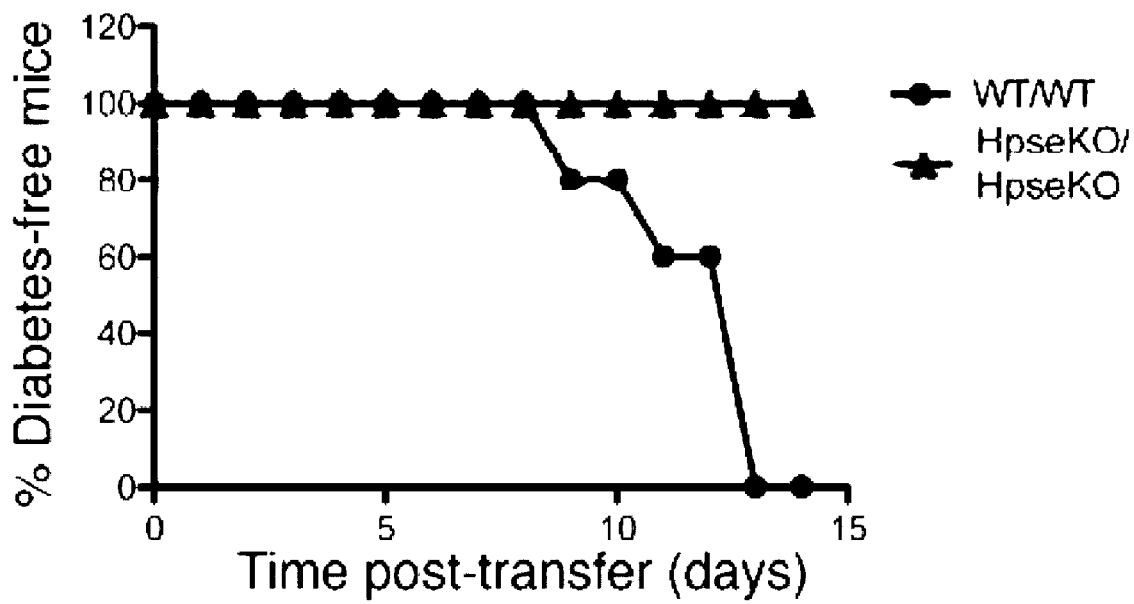
FIG. 1. Wild-type (WT) RIP-OVAhi mice become diabetic within 2 weeks after transfer of (WT) activated OT-II and naïve OT-I tg T cells. In contrast, transfer of heparanase-deficient (Hpse KO) OT-II and OT-1 tg T cells into heparanase-deficient RIP-OVAhi mice confirmed that Type 1 diabetes induction is heparanase-dependent.

The present invention relates to functionalized quinazolinyl compounds of general formula (I) as defined herein, and to the use of such compounds in the treatment of diseases or conditions associated with heparanase activity. In preferred embodiments, the compounds of general formula (I) are heparanase inhibitors.

In one aspect the invention relates to compounds of general formula (I):

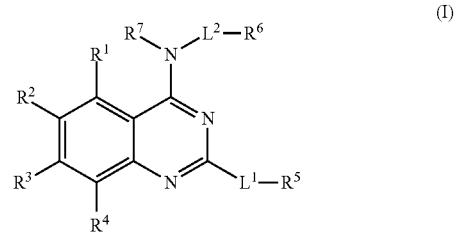

or a salt, hydrate, solvate, tautomer or stereoisomer thereof,
wherein:
$R^1$ is selected from H, hydroxyl, halo, $C_{1-6}$ alkyl, $C_{1-4}$ alkoxy, O—$CH_2$phenyl, O-phenyl;
$R^2$ is selected from H, hydroxyl, halo, $C_{1-6}$ alkyl, $C_{1-4}$ alkoxy, O—$CH_2$phenyl, O-phenyl;
$R^3$ is selected from H, hydroxyl, halo, $C_{1-6}$ alkyl, $C_{1-4}$ alkoxy, O—$CH_2$phenyl, O-phenyl;
$R^4$ is selected from H, hydroxyl, halo, $C_{1-6}$ alkyl, $C_{1-4}$ alkoxy, O—$CH_2$phenyl, O-phenyl;
or $R^1$ and $R^2$, or $R^2$ and $R^3$, or $R^3$ and $R^4$ together form $C_{1-3}$alkylenedioxy;
$L^1$ is selected from $C_{6-10}$ aryl, NH, NH$C_{1-4}$alkyl, NH$C_{1-4}$alkyl-NHC(O)—, NHC$_{1-4}$alkyl-NHSO$_2$—, azetidinyl-NHC(O)—, azetidinyl-NHSO$_2$—, N(C$_{1-4}$alkyl)$_2$ wherein each alkyl is the same or different and is optionally substituted with a halo or hydroxyl group, or $L^1$ is absent;

$R^5$ is selected from H, halo, hydroxyl, $C_{1-6}$ alkyl, $C_{1-6}$ alkenyl, $C_{1-6}$ alkynyl, $C_{3-6}$ cycloalkyl, $C_{6-10}$ aryl optionally substituted with 1 or 2 $R^X$ groups, $C_{2-9}$ heteroaryl optionally substituted with 1 or 2 $R^X$ groups, heterocycloalkyl optionally substituted with 1 or 2 $R^X$ groups, alkylheterocycloalkyl optionally substituted with 1 or 2 $R^X$ groups, C(O)-heterocycloalkyl optionally substituted with 1 or 2 $R^X$ groups, NHC(NH)NR'R" (wherein R' and R" are independently selected from H and $C_{1-3}$alkyl), NHC(O)NR'R" (wherein R' and R" are independently selected from H and $C_{1-3}$alkyl), or $R^5$ is absent;

$L^2$ is selected from $C_{1-4}$ alkyl, azetidinyl-C(O)—, $C_{1-4}$alkyl-NHSO$_2$—, —C(O)—, —SO$_2$—; or $L^2$ is absent;

$R^6$ is selected from H, $C_{1-6}$ alkyl, guanidinyl, NHC(NH)NH($C_{1-3}$alkyl), ureido, NHC(O)NH($C_{1-3}$alkyl), $C_{6-10}$ aryl optionally substituted with 1 or 2 $R^X$ groups, $C_{1-9}$ heteroaryl optionally substituted with 1 or 2 $R^X$ groups, $C_{2-5}$ heterocycloalkyl optionally substituted with 1 or 2 $R^X$ groups, $C_{3-6}$cycloalkyl optionally substituted with 1 or 2 $R^X$ groups;

$R^7$ is H or $C_{1-6}$ alkyl;

or when $L^2$ is absent $R^6$ and $R^7$ together with the nitrogen to which they are attached form a heterocycloalkyl ring optionally substituted with 1 or 2 $R^X$ groups;

each $R^X$ is independently selected from hydroxyl, halo, nitro, NR'R" (wherein R' and R" are independently selected from H and $C_{1-3}$alkyl), $C_{1-4}$ alkyl, $C_{3-6}$cycloalkyl, $C_{1-4}$alkoxy, C(O)$C_{1-3}$alkyl, C(O)O$C_{1-4}$alkyl, C(O)NHR$^Y$, $C_{6-10}$aryl optionally substituted with 1 or 2 $R^Y$ groups, $C_{2-9}$heteroaryl optionally substituted with 1 or 2 $R^Y$ groups, $C_{1-4}$alkyl-($C_{2-9}$heteroaryl), $C_{2-5}$heterocycloalkyl optionally substituted with 1 or 2 $C_{1-4}$alkyl groups, $C_{1-4}$alkyl-($C_{2-5}$heterocycloalkyl) optionally substituted with 1 or 2 $C_{1-4}$alkyl groups, C(O)—$C_{2-9}$heteroaryl optionally substituted with 1 or 2 $C_{1-4}$ alkyl groups; SO$_2$—$C_{2-9}$heteroaryl optionally substituted with 1 or 2 $C_{1-4}$ alkyl groups, or halo$C_{1-4}$ alkyl groups; or two adjacent $R^X$ groups together form $C_{1-3}$alkylenedioxy;

$R^Y$ is selected from H, hydroxyl, halo, $C_{1-4}$alkyl, halo$C_{1-4}$alkyl, $C_{1-4}$alkoxy.

In preferred embodiments each heteroaryl and each heterocycloalkyl group has at least one nitrogen heteroatom.

In preferred embodiments the salt is a pharmaceutically acceptable salt.

In one or more embodiments, each heteroaryl is independently selected from indolyl (e.g., N-indolyl, 2-indolyl, 3-indolyl, 5-indolyl), pyridyl (e.g., 2-pyridyl, 3-pyridyl, 4-pyridyl), triazolyl, oxazolyl (e.g., 1,3-oxazolyl, 1,2-oxazolyl), oxadiazolyl, quinolinyl, isoquinolinyl, pyrrolyl, or pyrazolyl, each of which may be optionally substituted with 1 or 2 $R^X$ groups.

In one or more embodiments, each heterocycloalkyl is independently selected from aziridinyl, morpholinyl, piperidinyl, piperazinyl, each of which may be optionally substituted with 1 or 2 $R^X$ groups.

In one or more embodiments $R^1$ and $R^4$ are H. In one or more embodiments $R^2$ and $R^3$ are independently H, halo, $C_{1-3}$alkoxy. In one or more embodiments $R^2$ and $R^3$ are not both H. In one or more embodiments $R^2$ and $R^3$ are both $C_{1-3}$alkoxy e.g., methoxy, ethoxy. In one or more embodiments $R^2$ and $R^3$ together are methylenedioxy. In one or more embodiments, $R^1$ and $R^4$ are H and $R^2$ and $R^3$ are $C_{1-3}$alkoxy, preferably methoxy. In other embodiments $R^2$ is $C_{1-3}$alkoxy and $R^1$, $R^3$ and $R^4$ are H.

In one or more embodiments $L^1$ is NH, or NHC$_{1-2}$alkyl. In one or more embodiments $L^1$ is phenyl. In one or more embodiments $L^1$ is NHC$_{1-2}$alkyl-NHC(O)—, azetidinyl-NHC(O)—, NHC$_{1-4}$alkyl-NHSO$_2$—, or azetidinyl-NHSO$_2$—. In one or more embodiments $L^1$ is absent.

In or more embodiments $R^5$ is halo, guanidinyl, ureido, or a group selected from $C_{3-6}$cycloalkyl, phenyl, naphthyl, indolyl (e.g., 2-indolyl or 3-indolyl), pyridyl (e.g., 2-pyridyl, 3-pyridyl or 4-pyridyl), quinolinyl, isoquinolinyl, morpholinyl, piperidinyl, piperazinyl, triazolyl (e.g., 4-triazolyl), pyrazolyl (e.g., N(1)-pyrazolyl, 3-pyrazolyl); oxazolyl (e.g., 1,3-oxazolyl, 1,2-oxazolyl), oxadiazolyl, benzodiazolyl, pyrrolopyridinyl (e.g., pyrrolo[2,3-b]pyridinyl), wherein each group is optionally substituted with 1 or 2 $R^X$ groups.

In one or more embodiments, $L^1$ is absent and $R^5$ is selected from $C_{1-6}$ alkyl, $C_{1-6}$ alkenyl and $C_{1-6}$ alkynyl. In one or more embodiments, $L^1$ is absent and $R^5$ is $C_{6-10}$aryl (e.g., phenyl, naphthyl) optionally substituted with 1 or 2 $R^X$ groups (e.g, CF$_3$, methoxy, methylenedioxy, 1,2-ethylenedioxy, morpholinyl, CH$_2$-morpholinyl). In one or more embodiments $L^1$ is absent and $R^5$ is C(O)piperazinyl (e.g., C(O)(N(1)-piperazinyl) optionally substituted with 1 or 2 $C_{1-3}$alkyl groups. In one or more embodiments, $L^1$ is absent and $R^5$ is $C_{2-9}$heteroaryl (e.g., indolyl, quinolinyl) optionally substituted with 1 or 2 $R^X$ groups.

In one or more embodiments $L^1$ is phenyl and $R^5$ is C(O)piperazinyl (e.g., C(O)(N(1)-piperazinyl) optionally substituted with 1 or 2 $C_{1-3}$alkyl groups.

In one or more embodiments, $L^1$ is NHC$_{1-2}$alkyl and $R^5$ is guanidinyl, ureido, or $C_{2-9}$heteroaryl (e.g., indolyl, quinolinyl) optionally substituted with 1 or 2 $R^X$ groups.

In one or more embodiments, $L^1$ is NHC$_{1-2}$alkyl-NHC(O)—, azetidinyl-NHC(O)— or azetidinyl-NHSO$_2$—, and $R^5$ is $C_{2-9}$heteroaryl (e.g., 1,3-oxazolyl, 1,2-oxazolyl, oxadiazolyl) optionally substituted with 1 or 2 groups selected from $C_{6-10}$aryl (e.g., phenyl), or $C_{2-9}$heteroaryl (e.g., indolyl).

In one or more embodiments, $L^1$ is absent and $R^5$ is $C_{6-10}$aryl (e.g., phenyl, naphthyl) optionally substituted with 1 or 2 groups selected from $C_{1-3}$ alkyl, $C_{1-4}$ alkoxy, or two adjacent groups which together form methylenedioxy or 1,2-ethylenedioxy. In one or more embodiments, $L^1$ is absent and $R^5$ is $C_{2-9}$heteroaryl (e.g., indolyl, quinolinyl, pyridinyl) optionally substituted with 1 or 2 groups selected from $C_{1-3}$alkyl, or $C_{1-3}$alkoxy.

In one or more embodiments $R^5$ is piperazinyl (e.g., N(1)-piperazinyl) optionally substituted with 1 or 2 groups selected from $C_{1-3}$alkyl, $C_{2-9}$heteroaryl (e.g., indolyl, pyridyl) optionally substituted with 1 or 2 $C_{1-4}$alkyl or halo$C_{1-4}$ alkyl groups, or SO$_2$—$C_{2-9}$heteroaryl (e.g., indolyl, pyridyl) optionally substituted with 1 or 2 $C_{1-4}$ alkyl or halo$C_{1-4}$ alkyl groups.

In one or more embodiments, $L^1$ is absent; $L_2$ is absent; $R^5$ is N-piperazinyl optionally substituted with 1 or 2 groups selected from $C_{1-3}$alkyl, $C_{2-9}$heteroaryl (e.g., indolyl, pyridyl) optionally substituted with 1 or 2 $C_{1-4}$alkyl or halo$C_{1-4}$ alkyl groups, or SO$_2$—$C_{2-9}$heteroaryl (e.g., indolyl, pyridyl) optionally substituted with 1 or 2 $C_{1-4}$ alkyl or halo$C_{1-4}$ alkyl groups; $R^6$ is H and $R^7$ is H.

In one or more embodiments $L^2$ is $C_{1-2}$alkyl, $C_{1-2}$alkyl-NHC(O)—, $C_{1-2}$alkyl-NHSO$_2$, or azetidinyl-NHC(O)—.

In one or more embodiments $R^7$ is H, methyl or ethyl.

In one or more embodiments $L^2$ is $C_{1-2}$alkyl and $R^6$ is indolyl (e.g., 2-indolyl or 3-indolyl) optionally substituted with 1 or 2 $R^X$ groups.

In one or more embodiments $R^7$ is H, $L^2$ is C(O), and $R^6$ is $C_{1-4}$ alkyl or $C_{3-6}$cycloalkyl.

In one or more embodiments, $L^2$ is azetidinyl-C(O)— and $R^6$ is indolyl (e.g., 2-indolyl or 3-indolyl) optionally substituted with 1 or 2 $R^X$ groups.

In one or more embodiments $L^2$ is absent; and $R^6$ and $R^7$ together with the nitrogen to which they are attached form a piperazinyl ring optionally substituted with 1 or 2 $R^X$ groups.

In one or more embodiments $L^2$ is absent, $R^6$ is H and $R^7$ is H.

In one or more embodiments $L^1$ is absent, $R^6$ is $C_{6-10}$ aryl (e.g., phenyl) optionally substituted with 1 or 2 $R^X$ groups, $L^2$ is absent, $R^6$ is H and $R^7$ is H.

In one or more embodiments $L^1$ is absent, $R^5$ is quinolinyl optionally substituted with 1 or 2 $R^X$ groups, $L^2$ is $C_{1-2}$alkyl, $R^6$ is $C_{2-9}$ heteroaryl (e.g., pyridinyl, indolyl) or $C_{6-10}$ aryl (e.g., phenyl) and $R^7$ is H.

In one or more embodiments each $R^X$ is independently selected from hydroxyl, halo, haloC$_{1-3}$alkyl, $C_{1-3}$alkoxy, C(O)C$_{1-3}$alkyl, C(O)OC$_{1-3}$alkyl, NR'R" (wherein R' and R" are independently selected from H and $C_{1-3}$alkyl), phenyl optionally substituted with 1 or 2 $R^Y$ groups, morpholinyl optionally substituted with 1 or 2 $R^Y$ groups, piperazinyl optionally substituted with 1 or 2 $R^Y$ groups, C(O)piperazinyl optionally substituted with 1 or 2 $R^Y$ groups, C(O) morpholinyl optionally substituted with 1 or 2 $R^Y$ groups, pyridyl (e.g., 2-, 3- or 4-pyridyl) optionally substituted with 1 or 2 $R^Y$ groups, indolyl (e.g., 2-, 3- or 5-indolyl) optionally substituted with 1 or 2 $R^Y$ groups, or SO$_2$-indolyl (e.g., 2-, 3- or 5-indolyl) optionally substituted with 1 or 2 $R^Y$ groups, or two adjacent $R^X$ groups together form methylenedioxy.

In one or more embodiments $R^Y$ is selected from hydroxyl, halo, $C_{1-3}$alkyl, $C_{1-3}$alkoxy.

In one or more embodiments the invention relates to a compound corresponding to a general formula independently selected from formula (IA), formula (IB), formula (IC), or formula (ID) or a salt, hydrate, solvate, tautomer or stereoisomer thereof:

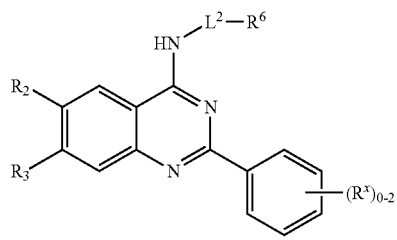

(IA)

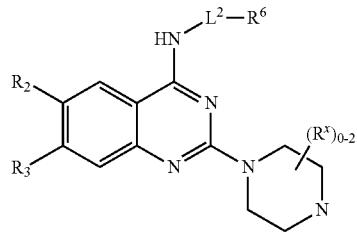

(IB)

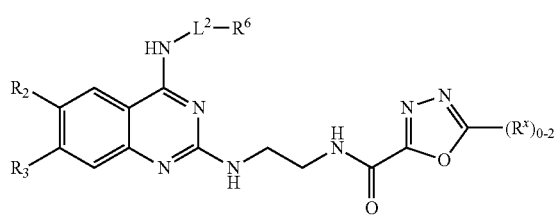

(IC)

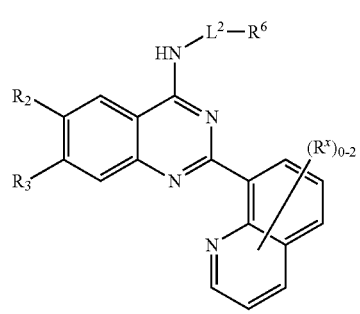

(ID)

wherein $R^2$, $R^3$, $R^6$, $R^X$ and $L^2$, are independently defined as for formula (I), including each of the preferred embodiments.

In another embodiment the invention relates to a compound of general formula (IE) or a salt, hydrate, solvate, tautomer or stereoisomer thereof:

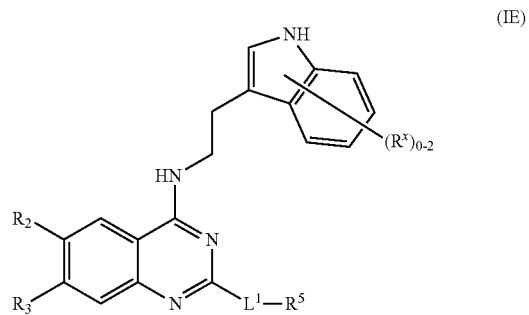

(IE)

wherein $R^2$, $R^3$, $R^5$, $L^1$ and $R^X$ are independently defined as for formula (I), including each of the preferred embodiments.

In one or more embodiments $R^2$ is H or $C_{1-3}$alkoxy; $R^3$ is H or $C_{1-3}$alkoxy; or $R^2$ and $R^3$ together form methylenedioxy.

It will be apparent to those skilled in the art that compounds of general formulae (IA)-(IE) are subsets of general formula (I). For the avoidance of doubt, throughout this specification a general reference to 'a compound of the invention' refers to compounds of general formulae (I), (IA), (IB), (IC), (ID) and (IE), and salts, hydrates, solvates, tautomers or stereoisomers thereof unless expressly stated otherwise. Similarly, a reference to 'a compound of formula (I)' or 'a compound of general formula (I)' includes compounds of general formulae (IA), (IB), (IC), (ID) and (IE) and salts, hydrates, solvates, tautomers or stereoisomers thereof unless expressly stated otherwise.

Compounds of general formula (I), or salts, hydrates, solvates, tautomers or stereoisomers thereof may be prepared using methods known to those skilled in the art, the illustrative reaction schemes and General Procedures disclosed herein, the specific methods described in the Examples section, or by routine modifications thereof. The present invention also encompasses any one or more of these processes for preparing the compounds of formula (I), in addition to any novel intermediates used therein.

Suitable reagents and reaction conditions for performing the described reactions are known to the skilled person and are described in the literature and text books, including for example March, *J. Advanced Organic Chemistry*, 4$^{th}$ Ed (John Wiley & Sons, New York, 1992) and *Vogel's Textbook of Practical Organic Chemistry*, 5th Ed (John Wiley & Sons, New York, 1989).

The reaction schemes presented below are illustrative of general methods that may be employed to prepare the compounds of the invention. Alternative methods, including routine modifications of the methods disclosed herein, will be apparent to those skilled in the art.

A general synthesis for the preparation of compounds of formula (I) is illustrated in Scheme 1.

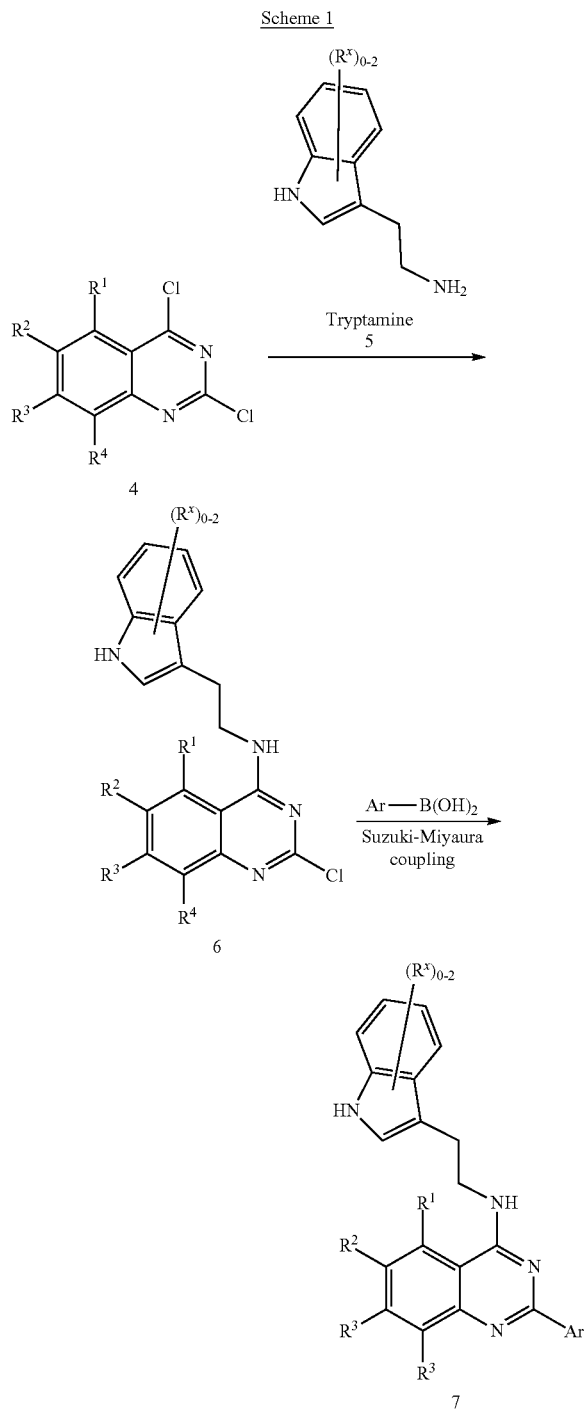

The synthesis shown in Scheme 1 commences with the condensation of a 2,4-dichloroquinazoline compound (4) with an amine compound represented by an optionally substituted tryptamine compound (5) to afford the amine-substituted quinazoline compound (6). This is followed by a Suzuki-Miyaura cross-coupling reaction with an optionally substituted aryl boronate to provide compounds of general formula (I) represented by structure 7. The reactions illustrated in Scheme 1 are described in more detail in General Procedure B and General Procedure C, below.

Typically, in the first reaction depicted in Scheme 1, an optionally substituted amine (5) (represented by tryptamine) is dissolved or suspended in a suitable solvent, such as THF, then treated with the 2,4-dichloroquinazoline compound (4), followed by addition (typically dropwise addition) of a base (e.g., triethylamine), after which the reaction is stirred for a period of time sufficient for the reaction to proceed substantially to completion. The precise period of time will depend, for example, on the scale of the reaction and the particular reaction conditions, however those skilled in the art will readily be able to determine suitable time and temperature conditions, and will be able to monitor the progress of the reaction using standard techniques, such as Thin Layer Chromatography (TLC), $^1$H NMR, etc to determine when the reaction is sufficiently or substantially complete. In a typical reaction, the reagents are stirred at a temperature between 15° C.-40° C., typically room temperature, for a period of about 4-24 hours, e.g., about 12 hours, or about 18 hours. The product may be isolated and purified using standard techniques known to those skilled in the art, e.g., solvent extraction (e.g., using an organic solvent such as ethyl acetate, chloroform, or the like, and washing with water and/or aqueous solution (e.g., sodium carbonate, sodium hydrogen carbonate, brine), followed by column chromatography and/or recrystallisation.

The second step is a Suzuki-Miyaura cross-coupling reaction, which involves reacting compound (6) with an aryl boronate compound to produce compound (7). In a typical reaction, a mixture of phenylboronic acid, compound (6) and a base (e.g., potassium carbonate), is treated with a de-gassed solvent mixture (e.g., a mixture of dimethoxyethane, water, ethanol). Bis(triphenylphosphine)palladium(II) dichloride catalyst is then added and the resultant mixture is sealed then irradiated with microwave radiation under nitrogen at a temperature and period of time until the reaction is judged to be substantially complete (typically 120° C./0.33 h, ramp time 1 minute, maximum power 200 W). Those skilled in the art know how to monitor the progress of a reaction using standard techniques, such as TLC, $^1$H NMR, etc. The product may be isolated and purified using standard techniques known to those skilled in the art, such as solvent extraction, e.g., using an organic solvent such as ethyl acetate, chloroform, or the like, and washing with water and/or aqueous solution (e.g., sodium carbonate, sodium hydrogen carbonate, brine), as well as other well-known conventional techniques such as column chromatography and/or recrystallisation.

An alternative synthetic sequence is illustrated in Scheme 2 in which the indole-substituted quinazoline compound (6) is condensed with an amine compound (8) to afford compounds of general formula (I), represented by structure (9).

Scheme 2

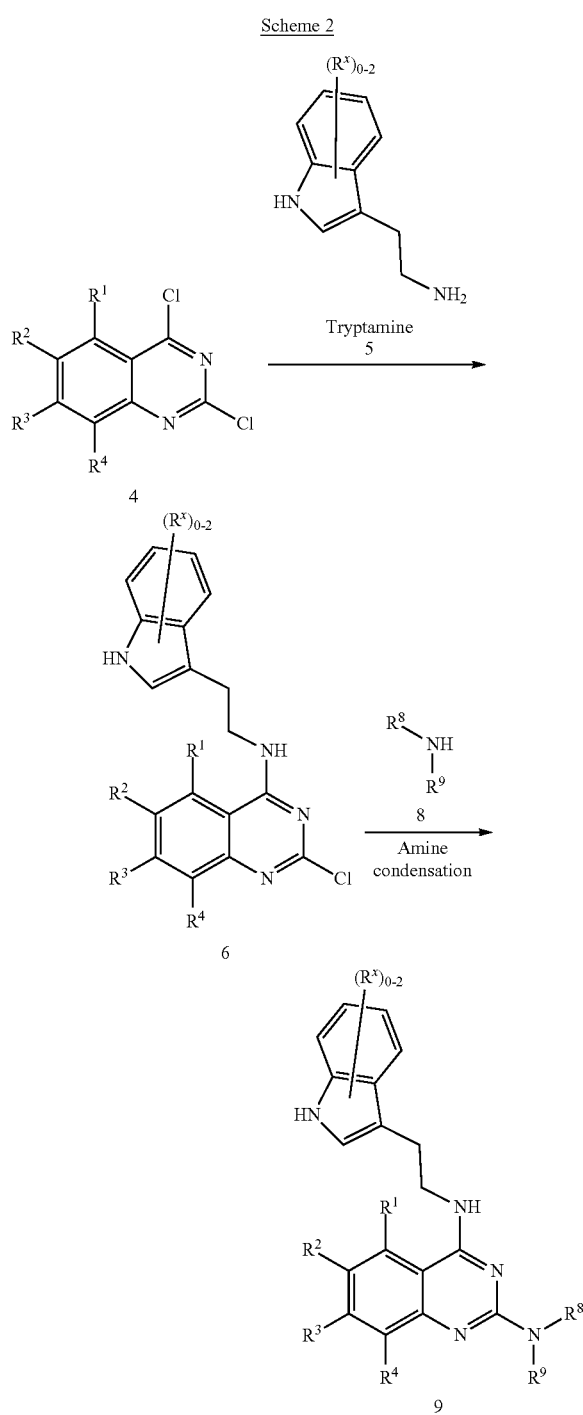

The reactions illustrated in Scheme 2 are described in detail in General Procedure B and General Procedure D, below.

The amine condensation reaction depicted in Scheme 2 is typically conducted under an inert gaseous atmosphere (e.g., nitrogen, argon) and involves reacting an amine (8) with compound (6) in the presence of a non-nucleophilic base (e.g., N,N-diisopropylethylamine, 2,6-dimethylpyridine, DABCO, N-methylmorpholine, triethylamine, etc), in a suitable protic solvent (e.g., an alcohol such as propanol, butanol, e.g., n-butanol) in a sealed vessel, which is then subjected to microwave irradiation sufficient for the reaction to be substantially complete. Those skilled in the art know how to monitor the progress of a reaction using standard techniques, such as TLC, $^1$H NMR, etc. (Exemplary microwave irradiation is 160° C./0.5 h, ramp time 2 minutes, maximum power 200 W). The product may be isolated and purified using standard techniques known to those skilled in the art, including e.g., solvent extraction, column chromatography, recrystallization, etc.

An alternative approach to preparing compounds of general formula (I) is illustrated in Scheme 3, which is based on a reaction sequence described by Seijas J. A et al. (*Tetrahedron Lett.* 2000, 41, 2215-2217).

Scheme 3

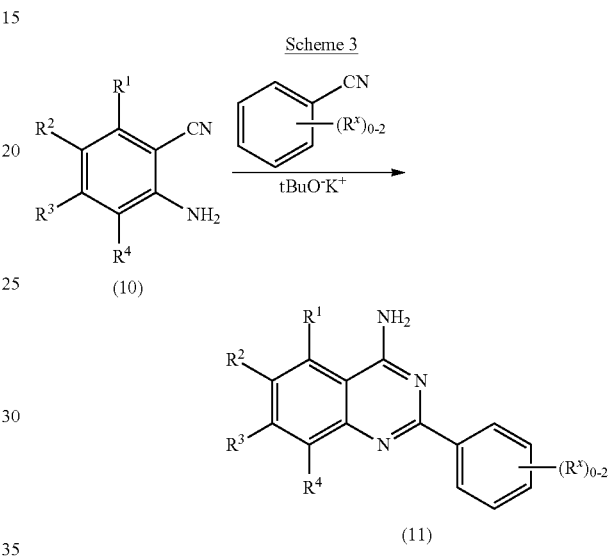

The reaction depicted in Scheme 3 involves reacting a 2-aminobenzonitrile compound (10) with an optionally substituted arylnitrile (such as benzonitrile) in the presence of a strong base (e.g., potassium t-butoxide) under an inert (e.g., nitrogen or argon) atmosphere. The reaction mixture is subjected to microwave irradiation to produce a compound of general formula (I) represented by structure (11). (Exemplary microwave irradiation conditions are 180° C./1 min., ramp time 1 min., maximum power 200 W). The product may be isolated and purified using standard techniques known to those skilled in the art, e.g., solvent extraction, column chromatography, recrystallization, and the like.

Where appropriate or necessary, protecting groups may be employed at any stage in the synthesis of compounds of formula (I). Similarly, those skilled in the art will also appreciate that compounds of the invention can also be prepared with certain protecting groups that are useful for purification or storage that can be removed before administration to a patient. Thus, this invention also encompasses compounds of the invention containing protective groups. Suitable protecting groups and their use are well known to those skilled in the art and include, for example, protecting groups described in Peter G. M. Wuts, Theodora W. Greene, "Greene's Protective Groups in Organic Synthesis", 4$^{th}$ Edition. (John Wiley & Sons, Inc., 2007). The protection and deprotection of functional groups is also described in "Protective Groups in Organic Chemistry", edited by J. W. F. McOmie, Plenum Press (1973).

Those skilled in the art will recognise the versatility of the reactions illustrated in the above Schemes, which can provide access to a wide range of substituted quinazoline compounds of general formula (I). The methods described above are merely representative and routine modifications and variations that would be apparent to persons skilled in the art fall within the broad scope and ambit of the invention disclosed herein.

Compounds of the invention may be isolated or purified using standard techniques known to those skilled in the art. Such techniques include precipitation, crystallisation, recrystallization, column chromatography (including flash column chromatography), HPLC, formation of salts, lyophilisation, among others. Suitable solvents for use in these techniques will be known or can be readily ascertained by those skilled in the art using routine practices.

Salts, including pharmaceutically acceptable salts, of compounds of formula (I) may be prepared by methods known to those skilled in the art, including for example:
  (i) by reacting the compound of formula (I) with the desired acid or base;
  (ii) by removing an acid- or base-labile protecting group from a suitable precursor of the compound of formula I or by ring-opening a suitable cyclic precursor, for example, a lactone or lactam, using the desired acid or base; or
  (iii) by converting one salt of the compound of formula (I) into another salt by reaction with an appropriate acid or base, or by means of a suitable ion exchange column.

The above reactions are typically carried out in solution. Suitable solvent systems (including mixed solvent systems) are well known to those skilled in the art and those skilled in the art can readily select or determine a suitable solvent system using routine methods taking into consideration the nature of the compound of formula (I), the particular salt being formed, and the amount of the compound of formula (I). Exemplary solvent systems include methanol, ethanol, water, acetone, tetrahydrofuran, dichloromethane, pentane, hexane, diethyl ether, ethyl acetate, and any mixture of two or more such solvents. The resulting salt may precipitate out and be collected by filtration or may be recovered by evaporation of the solvent. The degree of ionisation in the resulting salt may vary from completely ionised to almost non-ionised.

In Vitro Screening Assays

The present disclosure also includes in vitro screening assays for assessing the heparanase inhibitor activity of test compounds.

Suitable assays for determining heparanase inhibitory activity are known in the art, see, for example, the in vitro assays described in Rivara et al. (2016) *Future Med Chem*, 8(6): 647-680. For example, the method may include contacting a preparation comprising heparanase and a heparanase substrate (e.g. heparan sulfate or fondaparinux) with a test compound and detecting the amount of the intact substrate in comparison to a reference level of intact substrate in the absence of the test compound, or detecting the modulation of the activity of a downstream target of the intact heparanase substrate. Detecting the amount of intact substrate or modulation may be achieved using techniques including, but not limited to, ELISA, cell-based ELISA, inhibition ELISA, western blots, RIA, immunoprecipitation, immunostaining, a solid-phase labeled substrate assay such as a solid phase radio- or fluorescently-labeled or biotinylated substrate, an ultrafiltration assay, proximity assays such as HTRF and scintillation proximity assays, fluorescent assays using e.g. fluorescent substrate-heparanase substrate conjugates such as fluorescein or rhodamine, colorimetric assays and fluorescent immunoassays, all of which are well known to those skilled in the art.

In some embodiments, test compounds may be screened using commercially available assays, illustrative examples of which include Cisbio heparanase assay toolbox (Biotin-Heparan sulfate-Eu cryptate; Catalogue No. 61 BHSKAA; Cisbio Bioassays, Codolet France), Amsbio heparanase assay kit (Catalogue No. Ra001-BE-K; AMS Biotechnology Ltd, Abington UK) and InSight heparanase activity kit (Catalogue No. INS-26-4-0000-10; InSight Biopharmaceuticals, Rehovot, Israel).

Heparanase inhibitor compounds according to the present invention may elicit their heparanase inhibitory activity through one or more modes of action. For example, heparanase inhibitor compounds may decrease, inhibit or impair any one or more of heparanase catalytic activity, heparanase protein binding, heparanase-mediated modulation of gene transcription, heparanase-mediated initiation of cell signaling and/or angiogenesis.

Pharmaceutical Use

Compounds of general formula (I) according to the present invention are heparanase inhibitors and the invention also relates to a method of treating a condition or disease related to heparanase activity. Thus, an embodiment of the present invention relates to a method of treatment of a disease or condition associated with heparanase activity in a subject, the method comprising administering to the subject an effective amount of a compound of formula (I) or a pharmaceutical composition thereof.

A further embodiment of the invention relates to the use of a compound of formula (I) or a salt, hydrate, solvate, tautomer or stereoisomer thereof or a pharmaceutical composition thereof in the manufacture of a medicament for treating a disease or condition associated with heparanase activity.

In another aspect the present invention relates to the use of a compound of formula (I) or a salt, hydrate, solvate, tautomer or stereoisomer thereof or a pharmaceutical composition thereof for the treatment of a disease or condition associated with heparanase activity in a subject.

The expression "a disease or condition associated with heparanase activity" means that the heparanase enzyme plays a role in the disease or condition. However, other enzymes, pathways and mechanisms may also be implicated in the disease of condition. The compounds of the present invention may be an inhibitor of one or more activities of heparanase, including, but not limited to, heparanase catalytic activity. Furthermore, compounds of the present invention may partially or substantially inhibit any one or more heparanase activities.

In preferred embodiments the subject is a human.

In various embodiments the disease or condition is selected from Type 1 diabetes, Type 2 diabetes, nephritis, glomerulonephritis, cell-mediated autoimmune inflammation, diabetic nephropathy, gestational diabetes, diabetic ketoacidosis, hyperglycemia, hyperosmolar state, hypoglycemia, diabetic coma, diabetic cardiomyopathy, diabetic neuropathy, diabetic foot, diabetic retinopathy, diabetic myonecrosis, and diabetic encephalopathy. In other embodiments the disease or condition related to heparanase activity is selected from cancer, allergies, dermatitis, psoriasis, an ocular inflammatory disorder, such as, macular degeneration, retinitis pigmentosa and pancreatitis.

In preferred embodiments the disease or condition is selected from Type 1 diabetes, Type 2 diabetes, diabetic nephropathy, nephritis, glomerulonephritis, and cell-mediated autoimmune inflammation indications involving heparanase. In particularly preferred embodiments the disease is Type 1 diabetes or Type 2 diabetes.

The known drug doxazosin is a substituted quinazolinyl compound currently used to treat high blood pressure and urinary retention. The inventors surprisingly found that doxazosin also inhibits heparanase. Accordingly, another embodiment of the invention relates to a method of treatment of a disease or condition associated with heparanase activity in a subject, the method comprising administering to the subject an effective amount doxazosin to the subject, wherein the disease or condition is selected from Type 1 diabetes, Type 2 diabetes, nephritis, glomerulonephritis, cell-mediated autoimmune inflammation, diabetic nephropathy, gestational diabetes, diabetic ketoacidosis, hyperglycemia, hyperosmolar state, hypoglycemia, diabetic coma, diabetic cardiomyopathy, diabetic neuropathy, diabetic foot, diabetic retinopathy, diabetic myonecrosis, and diabetic encephalopathy.

In another aspect the invention relates to a method of controlling blood glucose levels in a subject, the method comprising administering to the subject an effective amount of a compound of general formula (I), or doxazosin, or a pharmaceutical composition thereof.

In a further aspect the invention relates to a method of treating or preventing rejection of a pancreatic islet transplant in a subject, the method comprising administering to the subject an effective amount of a compound of general formula (I), or doxazosin, or a pharmaceutical composition thereof.

In another aspect the invention relates to a method of preserving beta-cell function in a subject, the method comprising administering to the subject an effective amount of a compound of general formula (I) or doxazosin, or a pharmaceutical composition thereof.

Ocular inflammatory disorders such as diabetic retinopathy, age-related macular degeneration (AMD), retinitis pigmentosa, uveitis and viral corneal inflammation, occur wholly or in part from progressive inflammation in the eye. In a diseased eye, excessive macrophage activation and accumulation in particular tissues, such as the activation and accumulation of microglia in the sub-retinal space in degenerative disorders, can disrupt the immune privilege of the eye (Li et al. (2015) *Experimental Eye Research*, 136: 116-130). Heparanase has been shown to be important for ocular inflammation associated with viral infection of the cornea (Agelidis et al (2017) *Cell*, 20:439-450) as well as for the activation of macrophages (Gutter-Kapon et al. (2016) *PNAS*, 113(48): E7808-E781). Activated macrophages, including retinal microglia, produce different kinds of products including complement proteins, pro-inflammatory cytokines, reactive oxygen species, growth factors and other products, which can result in a chronic local inflammation and can typically lead to further damage (Li et al. (2015) *Experimental Eye Research*, 136: 116-130). For example, in the pathogenesis of AMD, microglia activated by cell death migrate to the damaged area to phagocytose cellular debris but also secrete molecules that kill neighboring photoreceptors around the area of primary degeneration (Li et al. (2015) *Experimental Eye Research*, 136: 116-130). Ocular macrophage, including microglial, activation is therefore an important target for the treatment and prevention of ocular inflammatory disorders. Accordingly, agents that target heparanase, including agents that inhibit at least one function or biological activity of heparanase, may prevent or reduce macrophage activation and may be useful for treating ocular inflammatory disorders, such as diabetic retinopathy and AMD, among others.

Thus, in another aspect the invention relates to a method for treating, or inhibiting the progression or development of, an ocular inflammatory disorder in a subject, the method comprising administering to the subject a compound of general formula (I) or a pharmaceutical composition thereof. The ocular inflammatory disorder may be any disorder of the eye which has an inflammatory component. Exemplary ocular inflammatory disorders include, but are not limited to, age-related macular degeneration (AMD) including the exudative or 'wet' AMD, dry AMD, diabetic retinopathy, retinitis pigmentosa, retinal vein occlusion, retinoblastoma, uveitis, macular edema, dry eye, viral infection and/or keratoconus; especially AMD, diabetic retinopathy and retinitis pigmentosa. In preferred embodiments, the ocular inflammatory disorder is AMD or diabetic retinopathy, preferably AMD. In preferred embodiments, the ocular inflammatory disorder is dry AMD. In other preferred embodiments the ocular inflammatory disorder is wet AMD. Although acute ocular inflammatory disorders are contemplated by the invention, in particularly preferred embodiments, the ocular inflammatory disorder is a chronic disorder.

Pharmaceutical Formulations

The compounds of the invention described herein may be administered as a formulation comprising a pharmaceutically effective amount of the compound, in association with one or more pharmaceutically acceptable excipients including carriers, vehicles and diluents. The term "excipient" herein means any substance, not itself a therapeutic agent, used as a diluent, adjuvant, or vehicle for delivery of a therapeutic agent to a subject or added to a pharmaceutical composition to improve its handling or storage properties or to permit or facilitate formation of a solid dosage form such as a tablet, capsule, or a solution or suspension suitable for oral, parenteral, intradermal, subcutaneous, or topical application. Excipients can include, by way of illustration and not limitation, diluents, disintegrants, binding agents, adhesives, wetting agents, polymers, lubricants, glidants, stabilizers, and substances added to mask or counteract a disagreeable taste or odor, flavors, dyes, fragrances, and substances added to improve appearance of the composition. Acceptable excipients include (but are not limited to) stearic acid, magnesium stearate, magnesium oxide, sodium and calcium salts of phosphoric and sulfuric acids, magnesium carbonate, talc, gelatin, acacia gum, sodium alginate, pectin, dextrin, mannitol, sorbitol, lactose, sucrose, starches, gelatin, cellulosic materials, such as cellulose esters of alkanoic acids and cellulose alkyl esters, low melting wax, cocoa butter or powder, polymers such as polyvinyl-pyrrolidone, polyvinyl alcohol, and polyethylene glycols, and other pharmaceutically acceptable materials. Examples of excipients and their use is described in *Remington's Pharmaceutical Sciences*, 20th Edition (Lippincott Williams & Wilkins, 2000). The choice of excipient will to a large extent depend on factors such as the particular mode of administration, the effect of the excipient on solubility and stability, and the nature of the dosage form.

The compounds and pharmaceutical compositions of the invention may be formulated for oral, injectable, rectal, parenteral, subcutaneous, intravenous, topical, intravitreal or intramuscular delivery. Non-limiting examples of particular formulation types include tablets, capsules, caplets, powders, granules, injectables, ampoules, vials, ready-to-use solutions or suspensions, lyophilized materials, creams, lotions, ointments, drops, suppositories and implants. Solid formulations such as the tablets or capsules may contain any number of suitable pharmaceutically acceptable excipients or carriers described above. The compounds of the invention may also be formulated for sustained delivery.

Tablets and capsules for oral administration may be in unit dose presentation form, and may contain conventional excipients such as binding agents, for example, acacia, gelatin, sorbitol, tragacanth, or polyvinylpyrollidone; fillers, for example lactose, sugar, maize-starch, calcium phosphate, sorbitol or glycine; tabletting lubricants, for example, magnesium stearate, talc, polyethylene glycol or silica; disintegrants, for example, potato starch; or acceptable wetting agents such as sodium lauryl sulphate. The tablets may be coated according to methods well known in normal pharmaceutical practice.

Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example, sorbitol, methyl cellulose, glucose syrup, gelatin, hydroxyethyl cellulose, carboxymethyl cellulose, aluminium stearate gel or hydrogenated edible fats, emulsifying agents, for example, lecithin, sorbitan monooleate, or acacia; non-aqueous vehicles (which may include edible oils), for example, almond oil, oily esters such as glycerin, propylene glycol, or ethyl alcohol; preservatives, for example, methyl or propyl p-hydroxybenzoate or sorbic acid; and, if desired, conventional flavouring or colouring agents.

For parenteral administration, including intravenous, intramuscular, subcutaneous, intravitreal, or intraperitoneal administration, fluid unit dosage forms may be prepared by combining the compound and a sterile vehicle, typically a sterile aqueous solution which is preferably isotonic with the blood of the recipient. Depending on the vehicle and concentration used, the compound may be either suspended or dissolved in the vehicle or other suitable solvent. In preparing solutions, the compound may be dissolved in water for injection and filter sterilized before filling into a suitable vial or ampoule and sealing. Advantageously, agents such as a local anaesthetic, preservative and buffering agents can be dissolved in the vehicle. To enhance the stability, the composition may be frozen after filling into the vial and the water removed under vacuum. The dry lyophilized powder may then be sealed in the vial and an accompanying vial of water for injection or other suitable liquid may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. A surfactant or wetting agent may be included in the composition to facilitate uniform distribution of the compound.

In one or more preferred embodiments the compounds of the invention are formulated as an injectable solution, suspension or emulsion. In preferred embodiments, the compounds of the invention are formulated for intravitreal injection into the eye of a subject. Such formulations may be particularly preferred for treatment of ocular inflammatory disorders, such as age-related macular degeneration (AMD) including the exudative or 'wet' and 'dry' form of AMD, diabetic retinopathy, retinitis pigmentosa, retinal vein occlusion, retinoblastoma, uveitis, macular edema, dry eye, viral infection and/or keratoconus; especially AMD, diabetic retinopathy and retinitis pigmentosa.

In preferred embodiments, ophthalmic formulations, including intravitreal formulations and other ophthalmic formulations, such as eye drops, typically may comprise one or more co-solvent(s), such as one or more organic co-solvents; one or more tonicity agent(s); a buffering system comprising one or more buffering agents; a stabilizing agent; pH between about 3-8. In preferred embodiments, the organic co-solvent may be polysorbate, for example, polysorbate 20 or polysorbate 80, polyethylene glycol (PEG), for example, PEG 3350, or propylene glycol, or a combination thereof; the tonicity agent may be, for example, sodium chloride or potassium chloride; the stabilizing agent may be sucrose, sorbitol, glycerol, trehalose, or mannitol; and the buffering agent may be, for example, phosphate buffer, such as a sodium phosphate buffer.

Intravitreal formulations are preferably sterile, isotonic and preferably have a pH within the range pH 3-8, preferably pH 5-7 or pH 3-5. Such formulations may contain one or more buffers as part of a buffer system, however, the concentration of buffers is preferably kept as low as possible. Buffer stressing studies may be carried out to select the minimal buffer amount needed to safely maintain the desired pH range. Exemplary intravitreal formulations are described in Shikari H, Samant P M. Intravitreal injections: A review of pharmacological agents and techniques. *J Clin Ophthalmol Res* 2016; 4:51-9.

In preferred embodiments, ophthalmically acceptable formulations may be lyophilizable. Lyophilizable formulations can be reconstituted into solutions, suspensions, emulsions, or any other suitable form for administration or use. Lyophilizable formulations are typically first prepared as liquids, then frozen and lyophilized. The total liquid volume before lyophilization can be less, equal to, or more than, the final reconstituted volume of the lyophilized formulation. The lyophilization process is well known to those of ordinary skill In the art, and typically Includes sublimation of water from a frozen formulation under controlled conditions. Lyophilized formulations typically can be stored at a wide range of temperatures. For example, lyophilized formulations may be stored below 25° C., for example, refrigerated at 2-8° C., or at room temperature (e.g., approximately 25° C.). Preferably, lyophilized formulations are stored below about 25° C., more preferably, at about 4-20° C.; below about 4° C.; or below about 0° C.

Lyophilized formulations are preferably reconstituted with a solution consisting primarily of water (e.g., USP WFI, or water for injection) or bacteriostatic water (e.g., USP WFI with 0.9% benzyl alcohol). Alternatively, solutions comprising buffers and/or excipients and/or one or more pharmaceutically acceptable carriers may be used. The liquid that is to undergo freeze-drying or lyophilization preferably comprises all components desired in a final reconstituted liquid formulation.

The pharmaceutical compositions of the invention may be administered locally to an eye using a variety of routes including, but not limited to, topical, through an ocular implant or direct injection into the eye. In particular embodiments, the pharmaceutical composition of the invention is administered locally to the eye using intravitreal injection, subconjunctival injection, sub-tenon injection, retrobulbar injection, suprachoroidal injection, intrascleral injection, intracorneal injection, subretinal injection or intracameral injection; especially intravitreal injection. In some embodiments, the composition is administered using a microneedle, for example, through intrascleral or intracorneal injection.

In some embodiments, the composition is administered using an ocular implant, for example, a biodegradable implant such as those made from, for example, polylactic acid (PLA), polyglycolic acid, poly(lactide-co-glycolide) (PLGA), cross-linked gelatin derivatives, hypromellose, polyesters and/or polycaprolactones; or a non-biodegradable implant such as those made from, for example, polyvinyl alcohol, ethylene vinyl acetate, silicon and/or polysulfone capillary fiber.

In some embodiments, the composition of the invention is formulated in a sustained release formulation or depot. Exemplary sustained release formulations or depots include a microsphere; matrix; emulsion; lipid-based; polymer-based; nanomicelle; micelle; nanovesicle such as a liposome, noisome, transfersome, discome, pharmacosome, emulsome or spanlastic, especially a liposome; microparticle; nanoparticle such as a nanocapsule or nanosphere composed of e.g. lipids, proteins, natural or synthetic polymers such as albumin, sodium alginate, chitosan, PLGA, PLA and/or polycaprolactone; or in situ gel such as an in situ hydrogel drug delivery system.

In some embodiments, the composition of the invention is formulated for topical administration to the eye. Thus, the composition may be in the form of an eye drop, gel or ointment; especially an eye drop. The composition may be in a single unit dose or multiple unit dose form.

The amount of therapeutically effective compound that is administered and the dosage regimen for treating a disease condition with the compounds and/or pharmaceutical compositions of the present invention depends on a variety of factors, including the age, weight, sex, and medical condition of the subject, the severity of the disease, the route and frequency of administration, the particular compound employed, as well as the pharmacokinetic properties (e.g., adsorption, distribution, metabolism, excretion) of the individual treated, and thus may vary widely. Such treatments may be administered as often as necessary and for the period of time judged necessary by the treating physician. One of skill in the art will appreciate that the dosage regime or therapeutically effective amount of the compound to be administrated may need to be optimized for each individual. The pharmaceutical compositions may contain active ingredient in the range of about 0.1 mg to 2000 mg, typically in the range of about 0.5 mg to 500 mg and more typically between about 1 mg and 200 mg. A daily dose of about 0.01 mg/kg to 100 mg/kg body weight, typically between about 0.1 mg/kg and about 50 mg/kg body weight, may be appropriate, depending on the route and frequency of administration. The daily dose will typically be administered in one or multiple, e.g., two, three or four, doses per day.

The compounds of the present invention may be administered along with a pharmaceutical carrier, diluent or excipient as described above. Alternatively, or in addition, the compounds may be administered in combination with other agents, for example, other antidiabetic therapeutic agents, or VEGF inhibitor drugs.

The terms "combination therapy" or "adjunct therapy" in defining use of a compound of the present invention and one or more other pharmaceutical agents, are intended to embrace administration of each agent in a sequential manner in a regimen that will provide beneficial effects of the drug combination, and is intended as well to embrace co-administration of these agents in a substantially simultaneous manner, such as in a single formulation having a fixed ratio of these active agents, or in multiple, separate formulations of each agent.

In accordance with various embodiments of the present invention one or more compounds of formula (I) may be formulated or administered in combination with one or more other therapeutic agents. Thus, in accordance with various embodiments of the present invention, one or more compounds of formula (I) may be included in combination treatment regimens with surgery and/or other known treatments or therapeutic agents, and/or adjuvant or prophylactic agents.

A number of agents are available in commercial use, in clinical evaluation and in pre-clinical development, which could be selected for treatment of Type 1 diabetes, Type 2 diabetes, diabetic nephropathy, nephritis, glomerulonephritis, and other cell-mediated autoimmune inflammation indications, cancer, psoriasis, dermatitis, allergy, macular degeneration, retinitis pigmentosa and pancreatitis as part of combination drug therapy. Suitable agents which may be used in combination therapy will be recognized by those of skill in the art. Suitable agents are listed, for example, in the Merck Index, *An Encyclopedia of Chemicals, Drugs and Biologicals*, 12$^{th}$ Ed., 1996, and subsequent editions, the entire contents of which are incorporated herein by reference.

For example, when used in the treatment of Type 1 diabetes or Type 2 diabetes, compounds of the present invention may be administered with an additional anti-diabetic agent, or combinations thereof, such as: biguanides (e.g., metformin), insulin secretagogues (e.g., sulfonylureas and glinides), glitazones, non-glitazone PPARγ agonists, PPARp agonists, inhibitors of DPPIV, inhibitors of PDE5, inhibitors of GSK-3, glucagon antagonists, inhibitors of f-1,615 BPase(Metabasis/Sankyo), GLP-1/analogs (AC 2993, also known as exendin-4), insulin and insulin mimetics (Merck natural products). Other examples include PKC-p inhibitors, AGE breakers, SGLT2 inhibitors, T cell inhibitors (including anti-CD3 monoclonal antibodies), B cell inhibitors (including anti-CD20 monoclonal antibodies such as Rituximab), CTLA-4Ig (Abatacept/Bristol-Myers Squibb) and inflammatory cytokine inhibitors including blocking monoclonal antibodies, among others.

In other embodiments, when used for the treatment of ocular inflammatory disorders, such as, for example, age-related macular degeneration (AMD), the compound of formula (I) may be administered in combination with a growth factor inhibitor. Suitable growth factor inhibitors include, but are not limited to, a vascular endothelial growth factor (VEGF) inhibitor, such as ranibizumab, aflibercept, bevacizumab, pegaptanib, conbercept, abicipar pegol (MP0112) and MP0250; a platelet derived growth factor (PDGF) inhibitor, such as E10030 (anti-PDGF PEGylated aptamer), trapidil and pegpleranib; and pharmaceutically acceptable salts and combinations thereof. In some embodiments, the one or more pharmaceutically active agent is a VEGF inhibitor selected from the group consisting of ranibizumab, aflibercept, bevacizumab, pegaptanib, conbercept and pharmaceutically acceptable salts and combinations thereof.

Combination regimens may involve the active agents being administered together, sequentially, or spaced apart as appropriate in each case. Combinations of active agents including compounds of the invention may be synergistic.

The co-administration of compounds of formula (I) may be effected by the compounds of formula (I) being in the same unit dose as another active agent, or the compounds of formula (I) and one or more other active agent(s) may be present in individual and discrete unit doses administered at the same, or at a similar time, or at different times according to a dosing regimen or schedule. Sequential administration may be in any order as required, and may require an ongoing physiological effect of the first or initial compound to be current when the second or later compound is administered, especially where a cumulative or synergistic effect is desired.

Embodiments of the invention will now be discussed in more detail with reference to specific examples which are provided for exemplification only and which should not be considered as limiting the scope of the invention in any way.

EXAMPLES

Abbreviations

BOC refers to a t-butoxycarbonyl group.
DCM refers to dichloromethane.
THF refers to tetrahydrofuran.
DMF refers to N,N-dimethylformamide.
DMSO refers to dimethyl sulfoxide.
EtOAc refers to ethyl acetate.
rt refers to room temperature.
General Procedures Unless otherwise specified, proton ($^1$H) and carbon ($^{13}$C) NMR spectra were recorded at room temperature in base-filtered CDCl$_3$ with a Bruker spectrometer operating at 400 MHz for proton and 100 MHz for carbon nuclei. For $^1$H NMR spectra, signals arising from the residual protio forms of the solvent were used as the internal standards. $^1$H NMR spectroscopic data are recorded as follows: chemical shift (δ) [multiplicity, coupling constant(s) J (Hz), relative integral] where multiplicity is defined as: s=singlet; d=doublet; t=triplet; q=quartet; m=multiplet; br=broad or combinations of thereof. The signal due to residual CHCl$_3$ appearing at δH=7.26 ppm and the central resonance of the CDCl$_3$ "triplet" appearing at δC=77.0 or 77.16 ppm were used to reference $^1$H and $^{13}$C NMR spectra, respectively. The quintet due to residual DMSO-d$_5$ appearing at δH=2.50 ppm and the central resonance of the DMSO-d$_6$ "multiplet" appearing at δC=39.52 ppm were used to reference $^1$H and $^{13}$C NMR spectra, respectively. Infrared spectra (IR: max) were recorded with a PerkinElmer 1800 series FTIR spectrometer or a PerkinElmer UATR Spectrum Two FTIR spectrometer. Samples were analyzed as thin films on KBr plates or compressed and flattened on a diamond window. Low-resolution ESI mass spectra were recorded on a single quadrupole liquid chromatograph-mass spectrometer, while high-resolution measurements were conducted on a time-of-flight instrument. Low- and high-resolution EI mass spectra were recorded with a magnetic-sector machine. Melting points were measured with an Optimelt automated melting point system and are uncorrected. Analytical thin layer chromatography (TLC) was performed on aluminium-backed 0.2 mm thick silica gel 60 F254 plates. Eluted plates were visualized with a 254 nm UV lamp and/or by treatment with a suitable dip followed by heating. These dips included phosphomolybdic acid/ceric sulfate/sulfuric acid (concd.)/water (37.5 g: 7.5 g: 37.5 g: 720 mL) or potassium permanganate/potassium carbonate/5% sodium hydroxide aqueous solution/water (3 g: 20 g: 5 mL: 300 mL). Flash chromatographic separations were carried out according to protocols defined by Still et al. *J. Org. Chem.* 1978, 43, 2923 with silica gel 60 (40-63 μm) as the stationary phase and with the AR- or HPLC-grade solvents indicated.

Microwave reactions were conducted with a CEM Explorer microwave reactor. Microwave vessels were sealed with a snap-cap and irradiated for the time and at the temperatures specified, typically with a ramp time of 1 minute to the specified temperature at a maximum power of 200 W.

Starting materials and reagents were generally available from the Sigma-Aldrich, Merck, TCI, Strem, AK Scientific or Lancaster chemical companies and were used as supplied. Drying agents and other inorganic salts were purchased from the AJAX, BDH or Unilab chemical companies. Tetrahydrofuran (THF), diethyl ether, methanol and dichloromethane (DCM) were dried by using a Glass Contour solvent purification system that is based upon a technology originally described by Grubbs et al. Organometallics 1996, 15, 1518. Where necessary or desirable, reactions were performed under nitrogen.

I. Synthesis Examples

General Experimental Procedures

The following General Experimental Procedures are illustrative synthetic methods that may be used in equivalent reactions involving alternative starting materials or reagents in order to produce the corresponding alternative reaction products.

General Procedure A

Preparation of 2,4-dichloroquinazolines

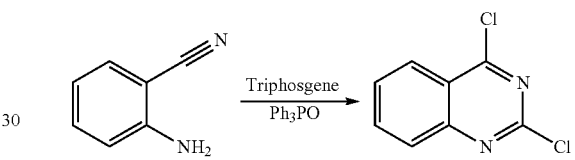

Using a procedure analogous to that reported by Zhong et al. (*Heterocycles* 2012, 85, 1417-1426), a magnetically stirred solution of triphenylphosphine oxide (170 mg, 0.6 mmol) in chlorobenzene (5 mL) at 0° C. was treated with triethylamine (400 μL). The solution was then treated dropwise with a solution of triphosgene (630 mg, 2.1 mmol) in chlorobenzene (6 mL) and stirring was continued at rt for 0.5 h. The mixture was then treated with 2-aminobenzonitrile (354 mg, 3 mmol) in one portion and heated at 120° C. for 5 hr. The mixture was cooled and stirred for 18 h at rt then water was added and the mixture extracted with EtOAc (3×15 mL). The combined organic layers were dried (Na$_2$SO$_4$) and concentrated in vacuo to afford a yellow solid which was subjected to flash column chromatography [silica, 1:10 v/v EtOAc/Pet spirit elution] to give, after concentration of the appropriate fractions the title compound (268 mg, 45%) as a white solid. Spectral data were consistent with those reported by Zhong et al (2012). $^1$H NMR (CDCl$_3$, 400 MHz) δ 8.27 (d, J=8.4 Hz, 1H), 8.04-7.97 (m, 2H), 7.79-7.71 (m, 1H); v$_{max}$ 1670, 1668, 1616, 1434, 1404, 1290, 1140, 753, 683 cm$^{-1}$.

General Procedure B

Addition of Amines to 2,4-dichloroquinazolines

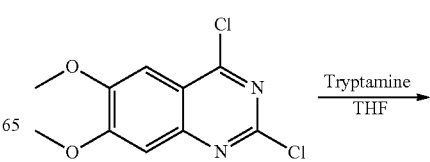

-continued

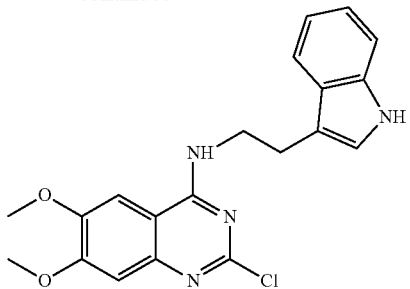

A magnetically stirred suspension of tryptamine (2.47 g, 15.4 mmol) in THF (100 mL) was treated with 2,4-dichloro-6,7-dimethoxyquinazoline (2.00 g, 7.72 mmol) followed by dropwise addition of triethylamine (1.08 mL, 7.72 mmol). The mixture was stirred for 18 h at 18° C., concentrated in vacuo and the residue diluted with DCM (80 mL) and washed with a saturated solution of sodium hydrogen carbonate (20 mL) and brine (20 mL) then dried ($Na_2SO_4$) and concentrated in vacuo to afford N-(2-(1H-indol-3-yl)ethyl)-2-chloro-6,7-dimethoxyquinazolin-4-amine (1.65 g; 56%). $^1$H NMR (DMSO-$d_6$, 400 MHz) δ 10.84 (s, 1H), 8.53 (t, J=5.6 Hz, 1H), 7.71 (d, J=7.8 Hz, 1H), 7.61 (s, 1H), 7.35 (d, J=8.1 Hz, 1H), 7.20 (d, J=2.1 Hz, 1H), 7.10-7.05 (m, 1H), 7.09 (s, 1H), 6.99 (t, J=7.8 Hz, 1H), 3.89 (s, 3H), 3.87 (s, 3H) 3.80-3.71 (m, 2H), 3.09-3.04 (m, 2H); $^{13}$C NMR (DMSO-$d_6$, 100 MHz) δ 160.0, 155.3, 154.4, 148.4, 147.2, 136.3, 127.3, 122.7, 121.0, 118.5, 118.3, 111.7, 111.4, 107.0, 106.5, 102.3, 56.1, 55.8, 41.8, 24.6; (+)-LRESIMS m/z (rel. int.) 383 (100); (+)-HRESIMS calcd. for $C_{20}H_{20}ClN_4O_2$ [M+H]$^+$ 383.1269. found 383.1271. $v_{max}$ 3408, 1587, 1499, 1425, 1336, 1249, 1220, 1148, 850, 743, 499 cm$^{-1}$.

General Procedure C

Suzuki-Miyaura Cross-Coupling Procedure

The general procedure is illustrated with respect to the synthesis of the compound BT1060:

A 10 mL snap-cap microwave vessel fitted with a magnetic stirring bar was charged with a mixture of phenylboronic acid (9.4 mg, 77.2 μmol), N-(2-(1H-indol-3-yl)ethyl)-2-chloro-6,7-dimethoxyquinazolin-4-amine (20.0 mg, 52.3 μmol) and potassium carbonate (38.0 mg, 274 μmol) then treated with a degassed mixture of dimethoxyethane, water and ethanol (7:3:2, 1 mL). Bis(triphenylphosphine)palladium(II) dichloride (1.8 mg, 5 mol %) was added and the mixture was sparged with nitrogen for 0.05 hr, sealed then subjected to microwave irradiation (120° C./0.33 h, ramp time 1 minute, maximum power 200 W). The mixture was treated with water (1 mL) and extracted with EtOAc (3×2 mL) and the combined organic layers washed with brine and concentrated under a gentle stream of nitrogen. The resulting residue was subjected to flash column chromatography [silica, 1:1 v/v EtOAc/Pet spirit elution] to give, after concentration of the appropriate fractions the compound BT1060 as a white solid (14.4 mg, 65%). $^1$H NMR (CDCl$_3$, 400 MHz) δ 8.58-8.54 (m, 2H), 8.15 (s, 1H), 7.73 (d, J=7.9 Hz, 1H), 7.52-7.43 (m, 3H), 7.41 (d, J=7.9 Hz, 1H), 7.30 (s, 1H), 7.23 (app. t, J=7.5 Hz, 1H), 7.14 (app. t, J=7.5 Hz, 1H), 7.10 (d, J=2.0 Hz, 1H), 6.60 (s, 1H), 5.54 (s, 1H), 4.15-4.09 (m, 2H, EtOAc obscured), 4.00 (s, 3H), 3.81 (s, 3H), 3.27 (app. t, J=6.6 Hz, 2H); $^{13}$C NMR (CDCl$_3$, 100 MHz) δ 159.5, 158.4, 154.2, 148.5, 147.3, 139.1, 136.4, 129.7, 128.2 (2C), 128.1 (2C), 127.7, 122.2, 119.7, 118.8, 115.3, 113.5, 111.4, 108.0, 107.3, 99.5, 56.2, 56.1, 42.2, 24.9; (+)-LRESIMS m/z (rel. int.) 425 (100) [M+H]$^+$, 447 (8) [M+Na]$^+$; (+)-HRESIMS calcd. for $C_{26}H_{25}N_4O_2$ [M+H]$^+$ 425.1972. found 425.1978; vmax 3347, 1624, 1594, 1524, 1501, 1458, 1422, 1368, 1254, 1214, 1128, 1027, 854 cm$^{-1}$.

General Procedure D

Addition of Amines to 2-chloroquinazolines

The general procedure is illustrated with respect to the synthesis of the compound BT2029:

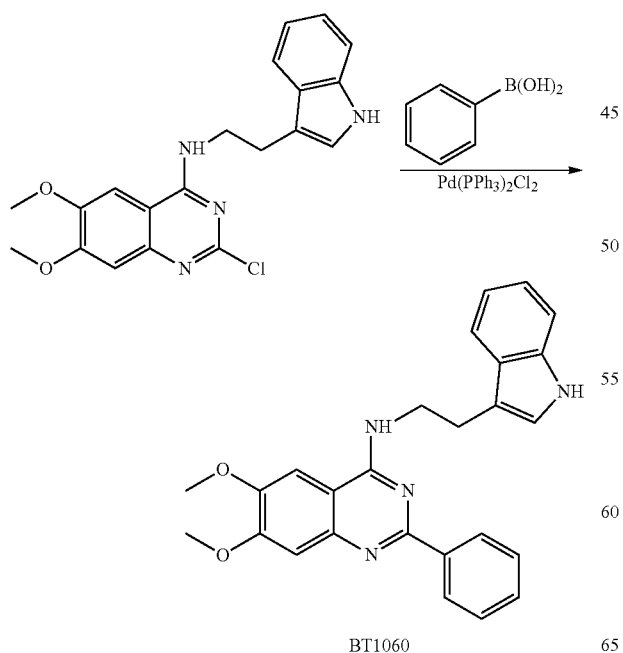

BT1060

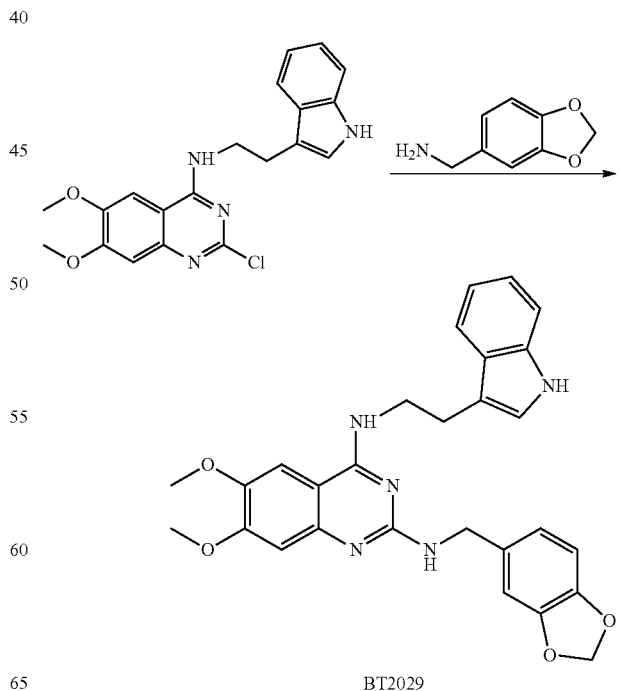

BT2029

A 10 mL snap-cap microwave vessel was charged with a mixture of piperonyl amine (103 mg, 0.68 mmol), N-(2-(1H-indol-3-yl)ethyl)-2-chloro-6,7-dimethoxyquinazolin-4-amine (65 mg, 0.17 mmol), N,N-diisopropylethylamine (89 μL, 0.51 mmol) and n-butanol (1.5 mL) sealed then subjected to microwave irradiation (160° C./0.5 h, ramp time 2 minutes, maximum power 200 W).

The mixture was cooled and concentrated in vacuo and the resulting residue was subjected to flash column chromatography [silica, 1:10 v/v ammoniacal methanol/DCM elution] to give, after concentration of the appropriate fractions the compound BT2029 as a white solid (67 mg, 79%). $^1$H NMR (DMSO-$d_6$, 400 MHz) δ 10.81 (s, 1H), 7.76-7.69 (m, 1H), 7.57 (d, J=7.9 Hz, 1H), 7.40 (s, 1H), 7.34 (d, J=8.1 Hz, 1H), 7.16 (d, J=2.3 Hz, 1H), 7.06 (t, J=7.5 Hz, 1H), 6.96 (t, J=7.4 Hz, 1H), 6.92 (s, 1H), 6.81 (dd, J=8.0, 0.9 Hz, 1H), 6.78 (d, J=8.0 Hz, 1H), 6.68 (s, 1H), 6.68-6.65 (m, 1H), 5.93 (s, 2H), 4.46 (d, J=6.3 Hz, 2H), 3.81 (s, 3H), 3.79 (s, 3H), 3.76-3.69 (m, 2H), 3.03 (app. t, J=7.6 Hz, 2H); (+)-LRESIMS m/z (rel. int.) 498 (100) [M+H]$^+$; (+)-HRESIMS calcd. for $C_{28}H_{28}N_5O_4$ [M+H]$^+$ 498.2136. found 498.2143; vmax 1626, 1498, 1488, 1456, 1435, 1359, 1231, 1209, 1035, 740 cm$^{-1}$.

General Procedure E

Amide Preparation

The general procedure is illustrated with respect to the synthesis of the compound BT2161:

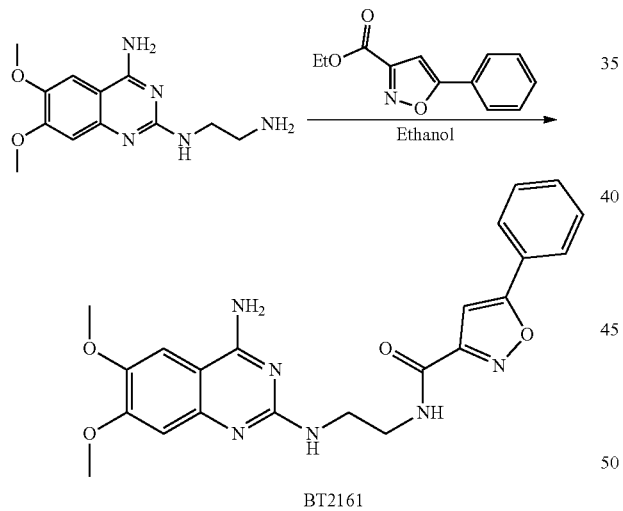

BT2161

A 10 mL snap-cap microwave vessel was charged with $N^2$-(2-aminoethyl)-6,7-dimethoxyquinazoline-2,4-diamine (121.2 mg, 0.46 mmol), ethyl 5-phenylisoxazole-3-carboxylate (50.0 mg, 0.23 mmol) prepared according to the procedure of Watterson et al. (J. Med. Chem. 2016, 59, 2820) and ethanol (1 mL). The tube was sealed and irradiated at 80° C. for 1 h before being stirred at 18° C. for 48 h. Solvent was evaporated and the resultant residue subjected to column chromatography [silica, 10:90 v/v methanol/dichloromethane elution] to afford, after concentration of the appropriate fractions ($R_f$=0.24) the compound BT2161 (75.0 mg, 75%) as white solid. $^1$H NMR (400 MHz, DMSO-$d_6$) δ 9.46 (brs, 1H), 7.88 (m, 2H), 7.53 (m, 3H), 7.45 (s, 1H), 7.34 (s, 1H), 7.15 (brs, 2H), 6.91 (s, 1H), 6.50 (brs, 1H), 3.88 (s, 3H), 3.79 (s, 3H), 3.51 (brs, 4H); $^{13}$C NMR (100 MHz, DMSO-$d_6$) δ 170.3, 161.2, 159.7, 159.2, 158.5, 154.1, 148.0, 144.8, 130.8, 129.3 (2C), 126.3, 125.7 (2C), 105.0, 104.0, 103.3, 99.9, 55.9, 55.4, 41.1, 40.2; (+)-LRESIMS m/z (rel. int.) 435 (100) [M+H]$^+$; HRMS (ESI, +ve) Found: (M+H)$^+$435.1766, $C_{22}H_{23}N_6O_4$ requires 435.1781; $v_{max}$ 3345, 3226, 2938, 1653, 1610, 1575, 1504, 1475, 1444, 1386, 1334, 1212, 1180, 1109, 1003, 853, 765 cm$^{-1}$.

General Procedure F

Boc Deprotection with Trifluoroacetic Acid in Dichloromethane

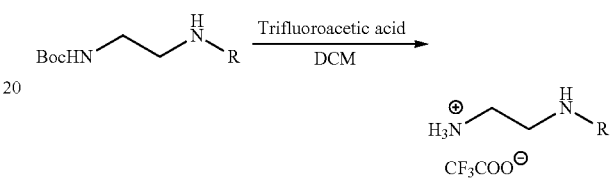

A magnetically stirred suspension of Boc-protected compound (1.80 mmol) in DCM (4 mL) maintained at 0° C. was treated with trifluoroacetic acid (1 mL) and magnetically stirred for 2 h. The cold bath was removed and the mixture was then stirred for a further 1 h at rt. The reaction was checked for completion by TLC analysis and then the solvent was removed with a gentle stream of nitrogen and the remaining gum was triturated with diethyl ether (3×10 mL) then placed under high vacuum for 1 h to afford the amine trifluoroacetate salt as a powder and used directly without further purification.

Experimental Procedures and Product Characterization

Preparation (i). 2,4-dichloro-6-methoxyquinazoline

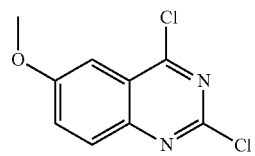

Prepared according to General Procedure A, from reaction of 2-amino-5-methoxybenzonitrile (444 mg, 3.00 mmol) and triphosgene (630 mg, 2.10 mmol) which afforded 2,4-dichloro-6-methoxyquinazoline (406 mg, 59%) as a white powder and used without further purification. $^1$H NMR (CDCl$_3$, 400 MHz) δ 7.91 (d, J=9.2 Hz, 1H), 7.62 (dd, J=9.2, 2.7 Hz, 1H), 7.42 (d, J=2.8 Hz, 1H), 4.00 (s, 3H); $^{13}$C NMR (CDCl$_3$, 100 MHz) δ 161.7, 159.6, 152.7, 148.5, 129.4, 129.1, 123.4, 102.8, 56.0; vmax 1619, 1541, 1489, 1418, 1390, 1291, 1221, 1109, 1019, 854, 837 cm$^{-1}$.

Preparation (ii). 2,4-dichloro-7-bromoquinazoline

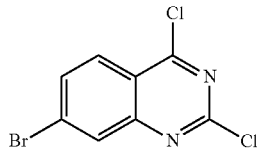 [SMILES: Clc1nc(Cl)c2ccc(Br)cc2n1]

Prepared according to General Procedure A, from reaction of 2-amino-4-bromobenzonitrile (591 mg, 3.00 mmol) and triphosgene (630 mg, 2.1 mmol) which afforded 2,4-dichloro-7-bromoquinazoline (527 mg, 64%) as a beige powder and used without further purification. $^1$H NMR (CDCl$_3$, 400 MHz) δ 8.19 (d, J=1.3 Hz, 2H), 8.12 (d, J=8.8 Hz, 2H), 7.83 (dd, J=8.8, 1.3 Hz, 1H); LRMS (EI, 70 eV) m/z (rel. int.) 278 (100, M+), 276 (63, M+), 243 (75), 241 (58), 178 (50); HREIMS calcd. for C$_8$H$_3$$^{79}$BrCl$_2$N$_2$ [M+] 275.8851. found 275.8860; vmax 3291, 3033, 2839, 1730, 1676, 1609, 1592, 1424, 1282, 1015, 858 cm$^{-1}$.

Preparation (iii). N-(2-(1H-indol-3-yl)ethyl)-2-chloroquinazolin-4-amine

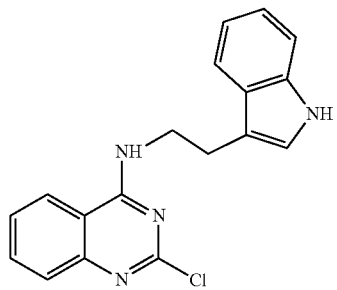 [SMILES: Clc1nc(NCCc2c[nH]c3ccccc23)c2ccccc2n1]

Prepared according to General Procedure B, from reaction of 2,4-dichloroquinazoline (153 mg, 0.77 mmol), tryptamine (308 mg, 1.54 mmol) and triethylamine (200 μL, 1.44 mmol) to afford a residue that was subjected to flash column chromatography [silica, 1:20 v/v MeOH/DCM elution] to give, after concentration of the appropriate fractions N-(2-(1H-indol-3-yl)ethyl)-2-chloroquinazolin-4-amine as a white solid (217 mg, 88%). $^1$H NMR (CDCl$_3$, 400 MHz) δ 7.74 (d, J=8.0 Hz, 1H), 7.73-7.63 (m, 2H), 7.44-7.36 (m, 2H), 7.39-7.30 (m, 2H), 7.23 (d, J=8.0 Hz, 1H), 7.15 (t, J=7.5 Hz, 1H), 7.13-7.07 (m, 1H), 6.10-6.01 (m, 1H), 4.01 (app. q, J=6.2 Hz, 2H), 3.19 (t, J=6.6 Hz, 2H); $^{13}$C NMR (CDCl$_3$, 100 MHz) δ 160.8, 157.8, 150.7, 136.5, 133.3, 127.7, 127.3, 126.0, 122.5, 122.2, 120.7, 119.7, 118.7, 113.3, 112.6, 111.4, 41.8, 24.7; (+)-LRESIMS m/z (rel. int.) 323 (100) [M+H]$^+$; (+)-HRESIMS calcd. for C$_{18}$H$_{16}$ClN$_4$ [M+H]$^+$ 323.1058. found 323.1065; v$_{max}$ 3407, 1606, 1574, 1532, 1426, 1334, 1275, 1191, 945, 738 cm$^{-1}$.

Preparation (iv). N-(2-(1H-indol-3-yl)ethyl)-7-bromo-2-chloroquinazolin-4-amine

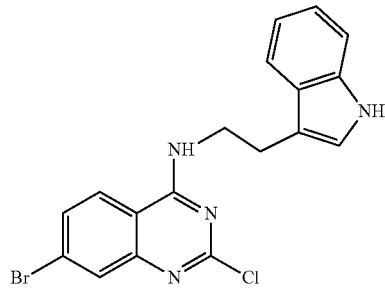 [SMILES: Clc1nc(NCCc2c[nH]c3ccccc23)c2ccc(Br)cc2n1]

Prepared according to General Procedure B, from reaction of 7-bromo-2,4-dichloroquinazoline (100 mg, 0.36 mmol), tryptamine (115 mg, 0.72 mmol) and triethylamine (200 μL, 1.44 mmol) to afford a residue that was subjected to flash column chromatography [silica, 1:20 v/v EtOAc/DCM elution] to give, after concentration of the appropriate fractions N-(2-(1H-indol-3-yl)ethyl)-7-bromo-2-chloroquinazolin-4-amine as a cream powder (115 mg, 80%). $^1$H NMR (CDCl$_3$, 400 MHz) δ 8.12 (s, 1H), 7.91 (d, J=2.0 Hz, 1H), 7.67 (d, J=7.9 Hz, 1H), 7.46-7.36 (m, 2H), 7.26-7.09 (m, 4H), 5.96 (s, 1H), 4.00 (app. q, J=6.2 Hz, 2H), 3.20 (t, J=6.2 Hz, 2H); (+)-LRESIMS m/z (rel. int.) 401 (100), 403 (100) [M+H]$^+$; (+)-HRESIMS calcd. for C$_{18}$H$_{15}$$^{79}$BrClN$_4$ [M+H]$^+$ 401.0163, found 401.0179; v$_m$3407, 1606, 1574, 1532, 1426, 1334, 1275, 1191, 945, 738 cm$^{-1}$.

Preparation (v). N-(2-(1H-indol-3-yl)ethyl)-2-chloro-6-methoxyquinazolin-4-amine

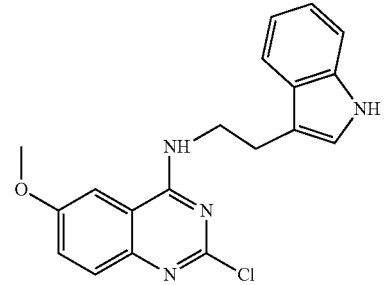 [SMILES: COc1ccc2nc(Cl)nc(NCCc3c[nH]c4ccccc34)c2c1]

Prepared according to General Procedure B, from reaction of 2,4-dichloro-6-methoxyquinazoline (200 mg, 0.87 mmol), tryptamine (280 mg, 1.75 mmol) and triethylamine (200 μL) to afford a residue that was subjected to flash column chromatography [silica, 1:20 v/v MeOH/DCM elution] to give, after concentration of the appropriate fractions N-(2-(1H-indol-3-yl)ethyl)-2-chloro-6-methoxyquinazolin-4-amine (211 mg, 69%) as a white powder. $^1$H NMR (CDCl$_3$, 400 MHz) δ 8.13 (s, 1H), 7.71 (d, J=8.1 Hz, 1H), 7.68 (d, J=9.2 Hz, 1H), 7.42 (d, J=8.1 Hz, 1H), 7.33 (dd, J=9.2, 2.7 Hz, 1H), 7.23 (dd, J=8.0, 0.8 Hz, 1H), 7.21-7.12 (m, 1H), 7.12 (d, J=2.3 Hz, 1H), 6.52 (d, J=2.7 Hz, 1H), 5.82-5.72 (m, 1H), 4.00 (app. q, J=6.2 Hz, 2H), 3.72 (s, 3H), 3.21 (app. t, J=6.2 Hz, 2H); $^1$H NMR (DMSO-d$_5$, 400 MHz) δ 10.85 (s, 1H), 8.74 (t, J=5.5 Hz, 1H), 7.73 (d, J=7.8 Hz, 1H), 7.67 (d, J=2.8 Hz, 1H), 7.57 (d, J=9.0 Hz, 1H), 7.41

(dd, J=9.0, 2.8 Hz, 1H), 7.37 (d, J=7.8 Hz, 1H), 7.22 (d, J=2.0 Hz, 1H), 7.09 (t, J=7.2 Hz, 1H), 7.00 (t, J=7.2 Hz, 1H), 3.87 (s, 3H), 3.85-3.75 (m, 2H), 3.15-3.04 (m, 2H); $^{13}$C NMR (DMSO-$d_6$, 100 MHz) δ 160.4, 157.1, 155.0, 145.4, 136.3, 128.1, 127.3, 124.2, 122.8, 121.0, 118.5, 118.3, 114.2, 111.6, 111.4, 102.8, 55.9, 41.9, 24.4; (+)-LRESIMS m/z (rel. int.) 353 (100) [M+H]$^+$, [M+H]$^+$; (+)-HRESIMS calcd. for $C_{19}H_{18}ClN_4O$ [M+H]$^+$ 353.1164. found 353.1171. $v_{max}$ 3476, 1629, 1587, 1568, 1535, 1514, 1450, 1331, 1254, 1240, 1169, 1041, 940, 904, 824, 745, 578 cm$^{-1}$.

Preparation (vi). N$^2$-(2-Aminoethyl)-6,7-dimethoxy-quinazoline-2,4-diamine

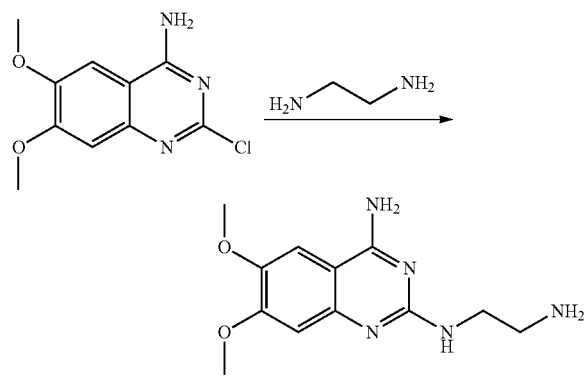

A solution of 2-chloro-6,7-dimethoxyquinazolin-4-amine (2.00 g, 8.34 mmol) and ethylenediamine (5.57 mL, 83.45 mmol) in water (25 mL) was heated under reflux for 16 h. The reaction mixture was then cooled down and solvent was evaporated under high vacuum to remove as much as possible the excess of ethylenediamine. The resulting residue was subjected to flash column chromatography [silica, 5:15:80 v/v 35% aqueous ammonia/methanol/chloroform elution] to give, after concentration of the appropriate fractions ($R_f$=0.19), N$^2$-(2-aminoethyl)-6,7-dimethoxyquinazoline-2,4-diamine (1.80 g, 82%) as a light yellow solid. $^1$H NMR (400 MHz, methanol-$d_4$) δ 7.27 (s, 1H), 6.79 (s, 1H), 3.88 (s, 3H), 3.84 (s, 3H), 3.45 (t, J=6.2 Hz, 2H), 2.83 (t, J=6.2 Hz, 2H); $^{13}$C NMR (100 MHz, methanol-$d_4$) δ 163.3, 160.8, 156.3, 149.8, 146.8, 105.1, 104.6, 104.4, 56.6, 56.2, 44.6, 42.5; (+)-LRESIMS m/z (rel. int.) 264 (100) [M+H]$^+$; $v_{max}$ 3168, 2934, 1671, 1603, 1576, 1503, 1480, 1454, 1435, 1380, 1312, 1232, 1209, 1111, 1031, 1004, 841, 829, 784 cm$^{-1}$.

Preparation (vii). 2-(3-Aminoazetidin-1-yl)-6,7-dimethoxyquinazolin-4-amine

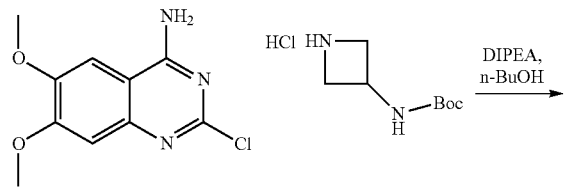

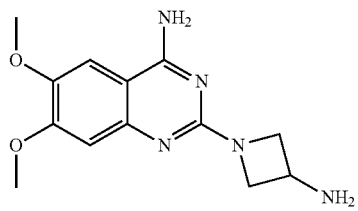

A 10 mL snap-cap microwave vessel was charged with a mixture of 2-chloro-6,7-dimethoxyquinazolin-4-amine (100.0 mg, 0.42 mmol), tert-butyl azetidin-3-ylcarbamate hydrochloride (130.6 mg, 0.63 mmol), N,N-diisopropylethylamine (0.18 mL, 1.04 mmol) and n-butanol (2 mL). The tube was sealed then subjected to microwave irradiation (120° C./1 h, ramp time 5 minutes, maximum power 250 W). The mixture was cooled and concentrated in vacuo and the resulting residue was subjected to flash column chromatography [silica, 5:95 to 20:80 v/v methanol/ethyl acetate elution] to give, after concentration of the appropriate fractions tert-butyl (1-(4-amino-6,7-dimethoxyquinazolin-2-yl)azetidin-3-yl)carbamate ($R_f$=0.40, 20:80 v/v methanol/ethyl acetate elution). $^1$H NMR (400 MHz, methanol-$d_4$) δ 7.26 (s, 1H), 6.79 (s, 1H), 4.45 (brs, 1H), 4.33 (t, J=7.9 Hz, 2H), 3.92 (dd, J=8.5 and 5.6 Hz, 2H), 3.89 (s, 3H), 3.86 (s, 3H), 1.45 (s, 9H); (+)-LRESIMS m/z (rel. int.) 376 (100) [M+H]$^+$; $v_{max}$ 3329, 3215, 2974, 1685, 1640, 1574, 1497, 1465, 1454, 1441, 1383, 1345, 1241, 1210, 1158, 1103, 1000, 842, 783 cm$^{-1}$. A solution of tert-butyl (1-(4-amino-6,7-dimethoxyquinazolin-2-yl)azetidin-3-yl)carbamate obtained above in DCM (2 mL) was treated dropwise with trifluoroacetic acid (0.5 mL) at 0° C. The resulting mixture was stirred at 20° C. until the completion conversion (observed by TLC). Solvent was then evaporated to obtain the TFA salt of 2-(3-aminoazetidin-1-yl)-6,7-dimethoxyquinazolin-4-amine. The product was then dissolved in pyridine (2 mL) and the solution was stirred for 15 min before evaporated and subjected to a short pad silica gel to afford the title compound ($R_f$=0.24, 10:90 v/v methanol saturated ammonia/dichloromethane elution) (100.0 mg, 87%). $^1$H NMR (400 MHz, acetone-$d_6$) δ 9.11 (brs, 1H), 7.39 (s, 1H), 6.87 (s, 1H), 6.72 (s, 2H), 4.80 (m, 1H), 4.37 (t, J=8.3 Hz, 2H), 4.05 (dd, J=9.0 and 5.4 Hz, 2H), 3.89 (s, 3H); (+)-LRESIMS m/z (rel. int.) 276 (100) [M+H]$^+$; $v_{max}$ 3343, 3195, 2957, 1640, 1606, 1558, 1492, 1438, 1411, 1376, 1345, 1277, 1237, 1210, 1128, 1097, 1031, 997, 839, 785 cm$^{-1}$.

Preparation (viii). 2-Chloro-6,7-dimethoxy-N-(2-(pyridin-2-yl)ethyl)quinazolin-4-amine

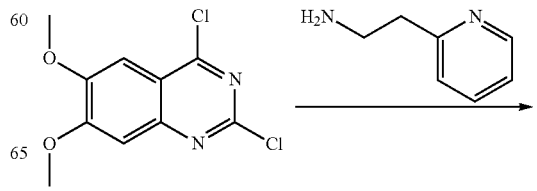

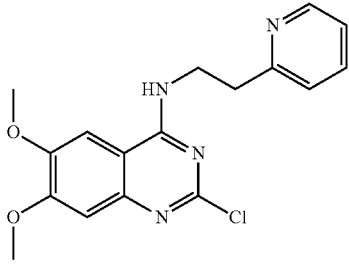

According to General Procedure B, a solution of 2,4-dichloro-6,7-dimethoxyquinazoline (400.0 mg, 1.54 mmol), 2-pyridylethylamine (370 μL, 3.08 mmol), triethylamine (215 μL, 1.54 mmol) in tetrahydrofuran (20 mL) was stirred at 18° C. for 18 h. 2-Chloro-6,7-dimethoxy-N-(2-(pyridin-2-yl)ethyl)quinazolin-4-amine (510.0 mg, 96%) ($R_f$=0.14, 97.5:2.5 v/v methanol/dichloromethane) was obtained as a white solid. $^1$H NMR (400 MHz, chloroform-d) δ 8.52 (d, J=4.7 Hz, 1H), 8.03 (brs, NH), 7.65 (t, J=7.6 Hz, 1H), 7.24 (d, J=7.8 Hz, 1H), 7.22-7.14 (m, 1H), 7.07 (s, 1H), 7.00 (s, 1H), 4.00 (s, 3H), 3.97 (m, overlapped, 2H), 3.93 (s, 3H), 3.15 (t, J=6.0 Hz, 2H); $^{13}$C NMR (101 MHz, chloroform-d) δ 160.3, 159.9, 156.4, 154.8, 148.9, 148.8, 147.7, 137.3, 124.0, 122.1, 107.2, 107.2, 100.3, 56.3, 56.1, 40.8, 35.7; MS (ESI, +ve) m/z 367 and 369 [(M+Na), 33 and 100%]; $v_{max}$ 3266, 2935, 1619, 1587, 1522, 1499, 1474, 1432, 1405, 1355, 1253, 1219, 1174, 1144, 1042, 1000, 854, 801, 788, 772, 757, 638 cm$^{-1}$.

Synthesis Example 1 BT2001 mg, 79 μmol) and N-(2-(1H-indol-3-yl)ethyl)-2-chloro-6,7-dimethoxyquinazolin-4-amine (20 mg, 52.3 μmol) to afford the compound BT2001 as a white powder (20 mg, 78%). $^1$H NMR (CDCl$_3$, 400 MHz) δ 8.66 (d, J=8.1 Hz, 2H), 8.14 (s, 1H), 7.73 (d, J=8.1 Hz, 2H), 7.72 (d, J=6.9 Hz, 1H), 7.41 (d, J=8.1 Hz, 1H), 7.30 (s, 1H), 7.26-7.22 (m, 1H), 7.15 (ddd, J=7.9, 7.1, 0.8 Hz, 1H), 7.11 (d, J=2.4 Hz, 1H), 6.59 (s, 1H), 5.58 (s, 1H), 4.14-4.09 (m, 2H), 4.02 (s, 3H), 3.81 (s, 3H), 3.27 (t, J=6.6 Hz, 2H); $^{13}$C NMR (CDCl$_3$, 100 MHz) δ 158.5, 158.1, 154.3, 148.9, 147.2, 136.4, 131.2 (q, JC-F=32.2 Hz), 128.3, 127.7, 125.10 (q, JC-F=3.6 Hz), 124.4 (q, JC-F=272.2 Hz), 122.3, 122.2, 119.7, 118.7, 113.4, 111.4, 108.1, 107.6, 99.5, 56.2, 56.1, 42.3, 24.9; (+)-LRESIMS m/z (rel. int.) 493 (100) [M+H]$^+$, 515 (15) [M+Na]$^+$; (+)-HRESIMS calcd. for C$_{27}$H$_{24}$N$_4$O$_2$ [M+H]$^+$ 493.1846. found 493.1851; $v_{max}$ 3434, 1618, 1592, 1575, 1524, 1499, 1428, 1321, 1255, 1212, 1111, 1065, 1001, 858 cm$^{-1}$.

Synthesis Example 2 BT2002

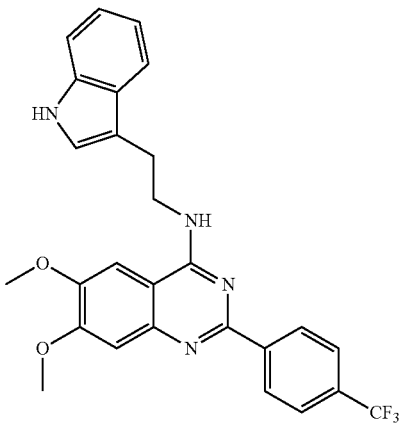 [SMILES: COc1cc2nc(-c3ccc(C(F)(F)F)cc3)nc(NCCc3c[nH]c4ccccc34)c2cc1OC]

Prepared according to General Procedure C from reaction of [4-(4-methylpiperazine-1-carbonyl)phenyl]boronic acid pinacol ester (26 mg, 79 μmol) and N-(2-(1H-indol-3-yl)ethyl)-2-chloro-6,7-dimethoxyquinazolin-4-amine (20 mg, 52.3 μmol) to afford a residue that was subjected to flash column chromatography [silica, 1:10 v/v MeOH/DCM elution] to give, after concentration of the appropriate fractions the compound BT2002 as a white powder (18 mg, 63%). $^1$H NMR (CDCl$_3$, 400 MHz) δ 8.57 (d, J=7.7 Hz, 2H), 8.36 (s, 1H), 7.69 (d, J=7.8 Hz, 1H), 7.50 (d, J=7.7 Hz, 2H), 7.39 (d, J=8.0 Hz, 1H), 7.29 (s, 1H), 7.21 (t, J=7.5 Hz, 1H), 7.11 (t, J=7.5 Hz, 1H), 7.05 (s, 1H), 6.65 (s, 1H), 5.77 (s, 1H), 4.10-4.04 (m, 2H), 4.00 (s, 3H), 3.91-3.76 (m, 2H), 3.81 (s, 3H), 3.49 (s br, 2H), 3.23 (t, J=6.2 Hz, 2H), 2.52 (s br, 2H), 2.41-2.31 (s br, 2H), 2.34 (s, 3H); (+)-LRESIMS m/z (rel. int.) 573 (100) [M+Na], 551 (80) [M+H]$^+$; (+)-HRESIMS calcd. for C$_{32}$H$_{35}$N$_6$O$_3$ [M+H]$^+$ 551.2765. found 551.2771; $v_{max}$ 2925, 1619, 1584, 1526, 1501, 1425, 1362, 1213, 1000, 854, 734 cm$^{-1}$.

Prepared and purified according to General Procedure C from reaction of (4-(trifluoromethyl)phenyl)boronic acid (15

Synthesis Example 3 BT2005

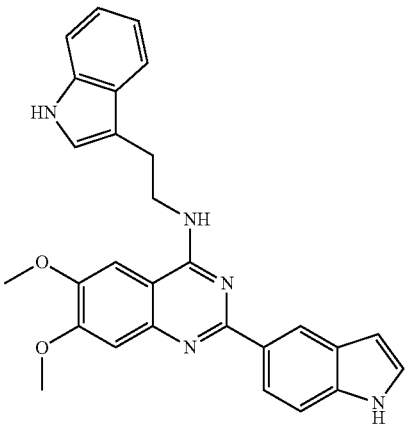 [SMILES: COc1cc2nc(-c3ccc4[nH]ccc4c3)nc(NCCc3c[nH]c4ccccc34)c2cc1OC]

Prepared according to General Procedure C from reaction of indole-5-boronic acid pinacol ester (19 mg, 79 μmol) and N-(2-(1H-indol-3-yl)ethyl)-2-chloro-6,7-dimethoxyquinazolin-4-amine (20 mg, 52.3 μmol) to afford a residue that was subjected to flash column chromatography [silica, 1:10 v/v MeOH/DCM elution] to give, after concentration of the appropriate fractions the compound BT2005 as a white powder (6 mg, 26%). $^1$H NMR N—Hs not observed (CD$_3$OD, 400 MHz) δ 8.51 (s, 1H), 8.01 (d, J=8.6 Hz, 1H), 7.63 (d, J=7.7 Hz, 1H), 7.44 (d, J=8.6 Hz, 1H), 7.35-7.30 (m, 3H), 7.13 (s, 1H), 7.10-7.05 (m, 2H), 6.96 (app. t, J=7.7 Hz, 1H), 6.57-6.56 (m, 1H), 4.00 (app. t, J=7.7 Hz, 2H), 3.92 (s, 3H), 3.87 (s, 3H), 3.18 (t, J=7.5 Hz, 2H); (+)-LRESIMS m/z (rel. int.) 464 (100) [M+H]$^+$; (+)-HRESIMS calcd. for C$_{28}$H$_{26}$N$_5$O$_2$ [M+H]$^+$ 464.2081. found 464.2087; ν$_{max}$ 1628, 1564, 1515, 1506, 1456, 1425, 1370, 1345, 1277, 1235, 1213, 1129, 854 cm$^{-1}$.

Synthesis Example 4 BT2007

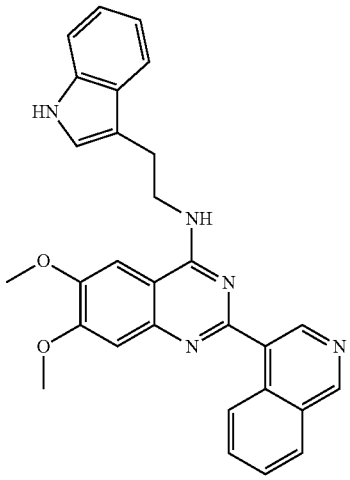 [SMILES: COc1cc2nc(-c3cncc4ccccc34)nc(NCCc3c[nH]c4ccccc34)c2cc1OC]

Prepared according to General Procedure C from reaction of isoquinoline-4-boronic acid pinacol ester (20 mg, 79 μmol) and N-(2-(1H-indol-3-yl)ethyl)-2-chloro-6,7-dimethoxyquinazolin-4-amine (20 mg, 52.3 μmol) to afford a residue that was subjected to flash column chromatography [silica, 1:10 v/v MeOH/DCM elution] to give, after concentration of the appropriate fractions the compound BT2007 as a white powder (16 mg, 64%). $^1$H NMR (CDCl$_3$, 400 MHz) δ 9.27 (s, 1H), 9.20 (s, 1H), 8.94 (d, J=8.6 Hz, 1H), 8.47 (s, 1H), 8.01 (d, J=8.2 Hz, 1H), 7.75-7.71 (m, 1H), 7.64-7.60 (m, 2H), 7.35 (d, J=8.2 Hz, 1H), 7.34 (s, 1H), 7.21-7.12 (m, 1H), 7.05 (s, 1H), 7.03 (t, J=7.3 Hz, 1H) 6.75 (s, 1H), 6.03 (s, NH), 4.06-4.02 (m, 2H), 4.00 (s, 3H), 3.82 (s, 3H), 3.21 (app. t, J=6.6 Hz, 2H); $^{13}$C NMR (CDCl$_3$, 100 MHz) δ 159.3, 158.5, 154.4, 153.2, 149.1, 146.5, 144.7, 136.4, 134.1, 130.9, 130.5, 128.7, 127.9, 127.6, 127.1, 125.8, 122.3, 122.1, 119.5, 118.6, 113.1, 111.4, 107.6, 107.1, 99.7, 56.2, 56.2, 42.4, 24.9; (+)-LRESIMS m/z (rel. int.) 476 (100) [M+H]$^+$; (+)-HRESIMS calcd. for C$_{29}$H$_{26}$N$_5$O$_2$ [M+H]$^+$ 476.2081. found 476.2087; ν$_{max}$ 1622, 1584, 1525, 1500, 1424, 1359, 797, 742 cm$^{-1}$.

Synthesis Example 5 BT2009

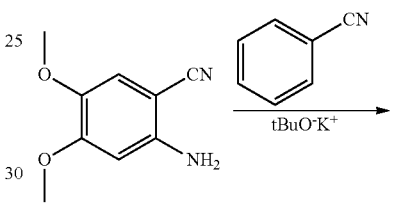

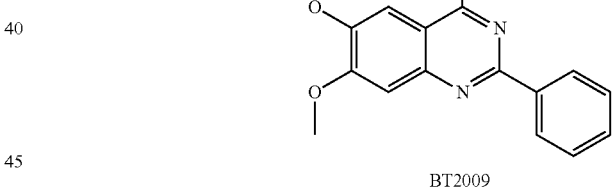

BT2009

Using a procedure analogous to that reported by Seijas J. A et al. (*Tetrahedron Lett.* 2000, 41, 2215-2217), a 10 mL snap-cap microwave vessel was charged with a mixture of 2-amino-4,5-dimethoxybenzonitrile (151 mg, 0.85 mmol), benzonitrile (87 mg, 0.84 mmol), and potassium t-butoxide (10 mg, 0.089 mmol), flushed with nitrogen and subjected to microwave irradiation for 1 minute (180° C./1 min., ramp time 1 min., maximum power 200 W). The mixture was cooled to rt and the residue subjected to flash column chromatography [silica, 1:1 v/v Et$_2$O/Pet spirit elution] to give, after concentration of the appropriate fractions the compound BT2009 (57 mg, 24%) as a white solid. $^1$H NMR (CDCl$_3$, 400 MHz) δ 8.47-8.43 (m, 2H), 7.51-7.43 (m, 2H), 7.36-7.24 (m, 1H), 7.33 (s, 1H), 6.93 (s, 1H), 5.41 (s, 2H), 4.05 (s, 3H), 4.02 (s, 3H); (+)-LRESIMS m/z (rel. int.) 282 (100) [M+H]$^+$; (+)-HRESIMS calcd. for C$_{16}$H$_{16}$N$_3$O$_2$ [M+H]$^+$ 282.1237. found 282.1244; ν$_{max}$ 3485, 3379, 1626, 1578, 1551, 1467, 1482, 1365, 1231, 1210, 851, 774, 702 cm$^{-1}$.

Synthesis Example 6 BT2016

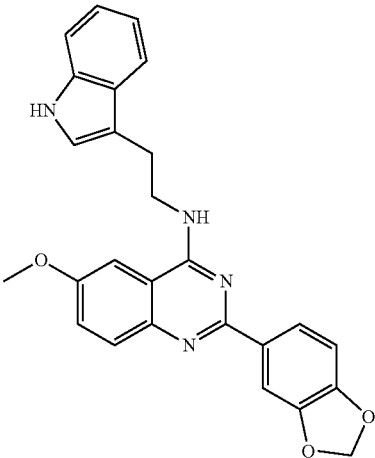 [SMILES: COc1ccc2nc(-c3ccc4c(c3)OCO4)nc(NCCc3c[nH]c4ccccc34)c2c1]

Prepared according to General Procedure C from reaction of 3,4-methylenedioxyphenylboronic acid, pinanol ester (32 mg, 0.13 mmol) and N-(2-(1H-indol-3-yl)ethyl)-2-chloro-6-methoxyquinazolin-4-amine (30 mg, 85 μmol) to afford a residue that was subjected to flash column chromatography [silica, 1:1 v/v EtOAc/Pet. spirit elution] to give, after concentration of the appropriate fractions the compound BT2016 as a white powder (21 mg, 56%). $^1$H NMR (DMSO-$d_6$, 400 MHz) δ 10.86 (s, 1H), 8.31 (t, J=5.6 Hz, 1H), 8.11 (dd, J=8.2, 1.6 Hz, 1H), 7.99 (d, J=1.2 Hz, 1H), 7.69-7.66 (m, 3H), 7.42-7.34 (m, 2H), 7.24 (d, J=2.3 Hz, 1H), 7.11-7.06 (m, 1H), 7.04-6.99 (m, 2H), 6.10 (s, 2H), 3.98-3.89 (m, 2H), 3.89 (s, 3H), 3.17 (app. t, J=7.6 Hz, 2H); $^{13}$C NMR (DMSO-$d_6$, 100 MHz) one signal obstructed or overlapping δ 158.9, 157.0, 156.6, 148.7, 147.4, 145.1, 136.3, 133.4, 129.2, 127.3, 123.5, 122.7, 122.1, 121.0, 118.3, 114.1, 112.0, 111.4, 107.9, 107.5, 102.4, 101.3, 55.8, 41.7, 24.8; (+)-LRESIMS m/z (rel. int.) 439 (100) [M+H]$^+$; (+)-HRESIMS calcd. for $C_{26}H_{23}N_4O_3$ [M+H]$^+$ 439.1765. found 439.1779; $v_{max}$ 3433, 3249, 1627, 1572, 1557, 1525, 1441, 1422, 1337, 1225, 1104, 1029, 837 cm$^{-1}$.

Synthesis Example 7 BT2030

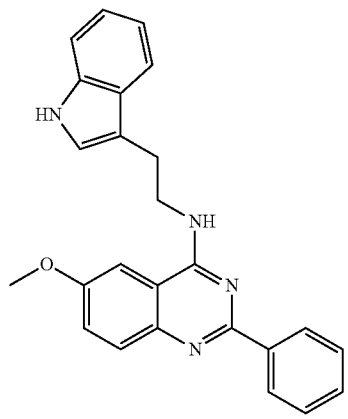 [SMILES: COc1ccc2nc(-c3ccccc3)nc(NCCc3c[nH]c4ccccc34)c2c1]

Prepared according to General Procedure C from reaction of phenylboronic acid (16 mg, 0.13 mmol) and N-(2-(1H-indol-3-yl)ethyl)-2-chloro-6-methoxyquinazolin-4-amine (30 mg, 85 μmol) to afford a residue that was subjected to flash column chromatography [silica, 1:1 v/v EtOAc/Pet. spirit elution] to give, after concentration of the appropriate fractions the compound BT2030 as a white powder (15 mg, 45%). $^1$H NMR (DMSO-$d_6$, 400 MHz) δ 10.85 (s, 1H), 8.49 (dd, J=7.7, 2.0 Hz, 2H), 8.38 (s br, 1H), 7.73 (d, J=9.1 Hz, 1H), 7.72-7.64 (m, 2H), 7.54-7.44 (m, 3H), 7.42 (dd, J=9.1, 2.7 Hz, 1H), 7.36 (d, J=8.0 Hz, 1H), 7.25 (d, J=2.7 Hz, 1H), 7.09 (t, J=7.6 Hz, 1H), 7.00 (t, J=7.4 Hz, 1H), 4.01-3.94 (m, 2H), 3.90 (s, 3H), 3.18 (t, J=7.6 Hz, 2H); (+)-LRESIMS m/z (rel. int.) 395 (100) [M+H]$^+$; (+)-HRESIMS calcd. for $C_{25}H_{23}N_4O$ [M+H]$^+$ 395.1866. found 395.1869; $v_{max}$ 3432, 1560, 1533, 1368, 1240, 1033, 831, 740, 710 cm$^{-1}$.

Synthesis Example 8 BT2031

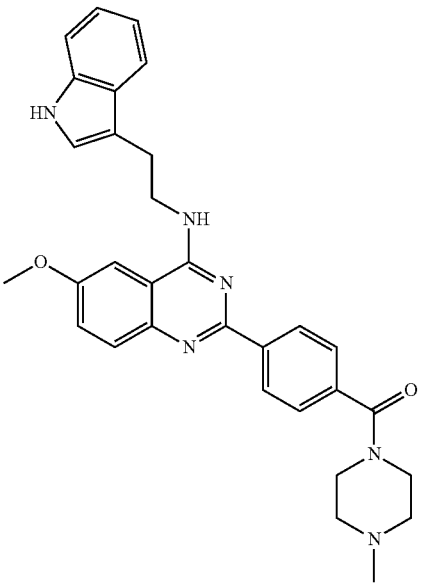 [SMILES: COc1ccc2nc(-c3ccc(C(=O)N4CCN(C)CC4)cc3)nc(NCCc3c[nH]c4ccccc34)c2c1]

Prepared according to General Procedure C from reaction [4-(4-methylpiperazine-1-carbonyl)phenyl]boronic acid pinacol ester (42 mg, 0.13 mmol) and N-(2-(1H-indol-3-yl)ethyl)-2-chloro-6-methoxyquinazolin-4-amine (30 mg, 85 μmol) to afford a residue that was subjected to flash column chromatography [silica, 1:10 v/v MeOH/DCM elution] to give, after concentration of the appropriate fractions the compound BT2031 as a white powder (29 mg, 65%). $^1$H NMR (DMSO-$d_6$, 400 MHz) δ 10.85 (s, 1H), 8.52 (d, J=8.3 Hz, 1H), 8.38 (t, J=5.6 Hz, 1H), 7.73 (d, J=9.0 Hz, 1H), 7.70 (d, J=2.7 Hz, 1H), 7.66 (d, J=7.8 Hz, 1H), 7.48 (d, J=8.3 Hz, 2H), 7.43 (dd, J=9.1, 2.7 Hz, 1H), 7.36 (d, J=8.0 Hz, 1H), 7.25 (d, J=1.8 Hz, 2H), 7.09 (t, J=7.3 Hz, 1H), 6.99 (t, J=7.4 Hz, 1H), 4.02-3.92 (m, 2H), 3.90 (s, 3H), 3.73-3.54 (m, 2H), 3.45-3.27 (m, 2H), 3.18 (app. t, J=7.6 Hz, 2H), 2.42-2.26 (m, 4H), 2.21 (s, 3H); (+)-LRESIMS m/z (rel. int.) 521 (100) [M+H]$^+$; (+)-HRESIMS calcd. for $C_{31}H_{33}N_6O_2$ [M+H]$^+$ 521.2660. found 521.2668; $v_{max}$ 3298, 2933, 1611, 1580, 1533, 1437, 1361, 1269, 1238, 1026, 999, 831, 740 cm$^{-1}$.

Synthesis Example 9 BT2036

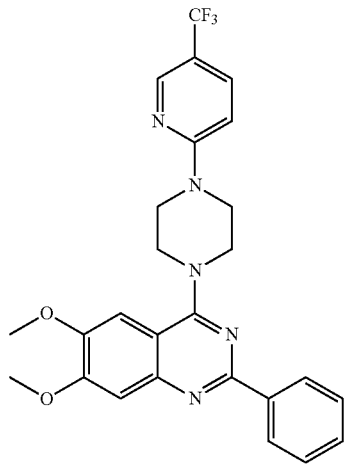 [SMILES: COc1cc2nc(-c3ccccc3)nc(N3CCN(c4ccc(C(F)(F)F)cn4)CC3)c2cc1OC]

A solution of 2,4-dichloro-6,7-dimethoxyquinazoline (100 mg, 0.39 mmol) and 1-(5-(trifluoromethyl)pyridin-2-yl)piperazine (89 mg, 0.41 mmol) in THF (4 mL) was treated with triethylamine (54 µL, 0.77 mmol) and stirred for 72 h. The mixture was concentrated in vacuo to afford a residue that was subjected to flash column chromatography [silica, 1:20 v/v MeOH/DCM elution] to give, after concentration of the appropriate fractions 2-chloro-6,7-dimethoxy-4-(4-(5-(trifluoromethyl)pyridin-2-yl)piperazin-1-yl)quinazoline as a white powder (170 mg, 97%). $^1$H NMR (DMSO-d$_6$, 400 MHz) δ 8.45 (s, 1H), 7.85 (dd, J=9.1, 2.6 Hz, 1H), 7.25 (s, 1H), 7.19 (s, 1H), 6.95 (d, J=9.1 Hz, 1H), 3.93 (s, 3H), 3.92 (s, 3H), 3.92-3.86 (m, 8H); $^{13}$C NMR (DMSO-d$_6$, 100 MHz) δ 163.6, 159.9, 154.8, 153.7, 150.0, 147.9, 145.3 (q, JC-F=4.0 Hz), 134.6 (q, JC-F=2.9 Hz), 124.9 (d, JC-F=270.3 Hz), 113.4 (q, JC-F=32.3 Hz), 108.3, 106.6, 106.1, 104.2, 56.0, 55.7, 48.1 (2C), 43.5 (2C); (+)-LRESIMS m/z (rel. int.) 454 (100) [M+H]$^+$; (+)-HRESIMS calcd. for $C_{20}H_{20}ClF_3N_5O_2$ [M+H]$^+$ 454.1252. found 454.1246; $v_{max}$ 1609, 1581, 1503, 1420, 1316, 1237, 1213, 1078, 854 cm$^{-1}$. A portion of the above material (33 mg, 73 µmol) was then reacted according to General Procedure C with phenylboronic acid (13 mg, 0.11 mmol) to afford a residue after workup, that was subjected to flash column chromatography [silica, 1:20 v/v ammoniacal MeOH/DCM elution] to give, after concentration of the appropriate fractions the compound BT2036 as a white powder (15 mg, 42%). $^1$H NMR (CDCl$_3$, 400 MHz) δ 8.56-8.50 (m, 2H), 8.45 (s, 1H), 7.69 (dd, J=9.0, 2.5 Hz, 1H), 7.53-7.42 (m, 3H), 7.37 (s, 1H), 7.19 (s, 1H), 6.73 (d, J=9.0 Hz, 1H), 4.07 (s, 3H), 4.02 (s, 3H), 3.96-3.86 (m, 8H); $^{13}$C NMR (CDCl$_3$, 100 MHz) δ 163.9, 160.4, 158.6, 154.6, 150.1, 148.5, 145.7 (1, JC-F=4.3 Hz), 138.6, 134.6 (q, JC-F=3.1 Hz), 129.9, 128.4 (2C), 128.0 (2C), 124.5 (q, JC-F=270.6 Hz), 115.7 (q, JC-F=33.0 Hz), 110.1, 108.0, 105.7, 102.9, 56.3, 56.1, 49.3 (2C), 44.5 (2C). (+)-LRESIMS m/z (rel. int.) 496 (100) [M+H]$^+$; (+)-HRESIMS calcd. for $C_{26}H_{25}F_3N_5O_2$ [M+H]$^+$ 496.1955. found 496.1960; $v_{max}$ 2963, 1612, 1505, 1413, 1259, 1246, 1097, 1083, 1019, 998, 952, 846, 794, 702 cm$^{-1}$.

Synthesis Example 10 BT2048

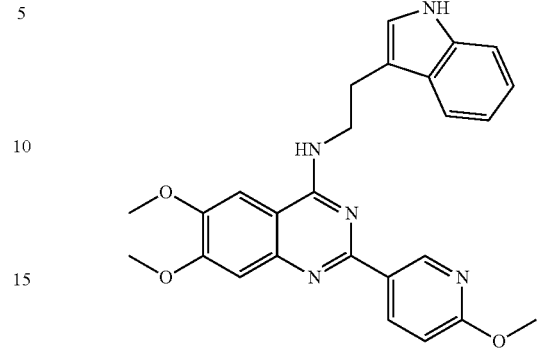

Prepared according to General Procedure C from reaction of 2-methoxy-5-pyridine boronic acid (39 mg, 0.25 mmol) and N-(2-(1H-indol-3-yl)ethyl)-2-chloro-6,7-dimethoxyquinazolin-4-amine (65 mg, 0.17 mmol) to afford a residue that was subjected to flash column chromatography [silica, 1:20 v/v MeOH/DCM elution] to give, after concentration of the appropriate fractions the compound BT2048 as a white powder (29 mg, 65%). $^1$H NMR (DMSO-d$_6$, 400 MHz) δ 10.85 (s, 1H), 9.22 (d, J=2.3 Hz, 1H), 8.64 (dd, J=8.7, 2.3 Hz, 1H), 8.19 (t, J=5.7 Hz, 1H), 7.63 (d, J=7.6 Hz, 1H), 7.63 (s, 1H), 7.36 (d, J=8.1 Hz, 1H), 7.24 (d, J=2.0 Hz, 1H), 7.16 (s, 1H), 7.08 (t, J=7.6 Hz, 1H), 6.99 (t, J=7.4 Hz, 1H), 6.91 (d, J=8.7 Hz, 1H), 3.96-3.92 (m, 2H), 3.93 (m, 6H), 3.90 (s, 3H), 3.15 (app. t, J=7.6 Hz, 2H); (+)-LRESIMS m/z (rel. int.) 456 (100) [M+H]$^+$; (+)-HRESIMS calcd. for $C_{26}H_{26}N_5O_3$ [M+H]$^+$ 456.2030. found 456.2024; $v_{max}$ 3438, 1621, 1605, 1578, 1520, 1494, 1427, 1369, 1336, 1251, 1237, 1212, 1131, 1002, 742 cm$^{-1}$.

Synthesis Example 11 BT2051

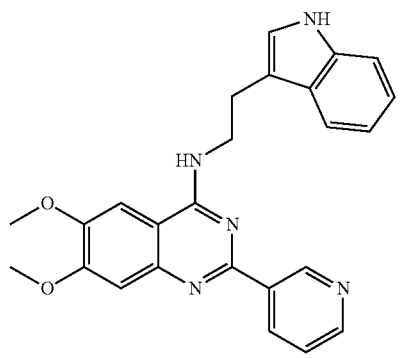 [SMILES: COc1cc2nc(-c3cccnc3)nc(NCCc3c[nH]c4ccccc34)c2cc1OC]

Prepared according to General Procedure C from reaction of 3-pyridylboronic acid pinacol ester (52 mg, 0.25 mmol) with N-(2-(1H-indol-3-yl)ethyl)-2-chloro-6,7-dimethoxyquinazolin-4-amine (65 mg, 0.17 mmol) to afford a residue that was subjected to flash column chromatography [silica, 1:20 v/v MeOH/DCM elution] to give, after concentration of the appropriate fractions the compound BT2051 as a white powder (35 mg, 48%). $^1$H NMR (DMSO-d$_6$, 400 MHz) δ 10.85 (s, 1H), 9.61 (s, 1H), 8.73-8.69 (m, 1H), 8.66-8.63 (m, 1H), 8.26 (t, J=5.7 Hz, 1H), 7.69-7.62 (m, 2H), 7.51 (dd, J=8.1, 4.9 Hz, 1H), 7.36 (d, J=8.1 Hz, 1H), 7.25-7.20 (m, 2H), 7.08 (t, J=7.5 Hz, 1H), 6.99 (t, J=7.5 Hz, 1H), 3.98-3.92 (m, 2H), 3.94 (s, 3H), 3.91 (s, 3H), 3.21-3.12 (m, 2H); (+)-LRESIMS m/z (rel. int.) 426 (100) [M+H]$^+$; (+)-HRESIMS calcd. for $C_{26}H_{24}N_6O_2$ [M+H]$^+$ 426.1925. found 426.1921; $v_{max}$ 1623, 1591, 1575, 1527, 1501, 1432, 1418, 1216, 1014, 826, 747 cm$^{-1}$.

Synthesis Example 12 BT2052

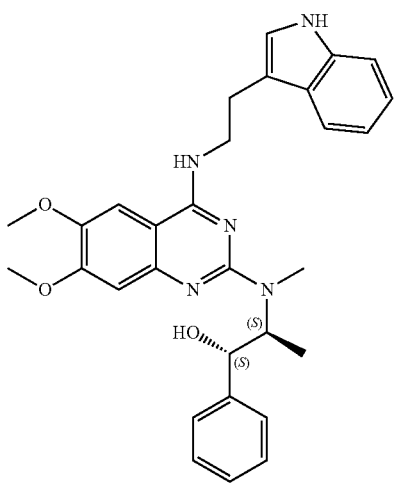

Prepared according to General Procedure D from reaction of (1S,2S)-pseudoephedrine hydrochloride (137 mg, 0.68 mmol) with triethylamine (267 µL, 1.53 mmol) and N-(2-(1H-indol-3-yl)ethyl)-2-chloro-6,7-dimethoxyquinazolin-4-amine (65 mg, 0.17 mmol) to afford a residue that was subjected to flash column chromatography [silica, 1:20 v/v ammoniacal MeOH/DCM elution] to give, after concentration of the appropriate fractions the compound BT2052 (56 mg, 64%) as a white powder. $^1$H NMR (DMSO-d$_6$, 400 MHz) 1H not observed or overlapping δ 8.10 (s, 1H), 7.68 (dd, J=7.9, 1.0 Hz, 1H), 7.46-7.37 (m, 3H), 7.36-7.27 (m, 2H), 7.27-7.18 (m, 2H), 7.14 (ddd, J=8.0, 7.0, 1.0 Hz, 1H), 7.08 (d, J=2.4 Hz, 1H), 6.90 (s, 1H), 6.44 (s, 1H), 5.36 (t, J=5.0 Hz, 1H), 4.76 (d, J=7.5 Hz, 1H), 4.61 (s br, 1H), 3.97 (s, 3H), 4.02-3.89 (m, 2H), 3.75 (s, 3H), 3.20 (t, J=6.6 Hz, 2H), 3.06 (s, 3H), 1.23 (d, J=7.1 Hz, 3H); (+)-LRESIMS m/z (rel. int.) 512 (100) [M+H]$^+$; (+)-HRESIMS calcd. for $C_{30}H_{34}N_5O_3$ [M+H]$^+$ 512.2656. found 512.2676; $v_{max}$ 1627, 1580, 1495, 1420, 1241, 1213, 1023, 741 cm$^{-1}$.

Synthesis Example 13 BT2053

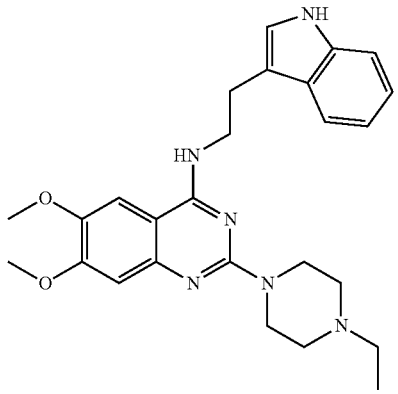 [SMILES: CCN1CCN(c2nc(NCCc3c[nH]c4ccccc34)c3cc(OC)c(OC)cc3n2)CC1]

Prepared according to General Procedure D from reaction of 1-ethylpiperazine (86 µL, 0.68 mmol) with N-(2-(1H-indol-3-yl)ethyl)-2-chloro-6,7-dimethoxyquinazolin-4-amine (65 mg, 0.17 mmol) to afford a residue that was subjected to flash column chromatography [silica, 1:10 v/v ammoniacal MeOH/DCM elution] to give, after concentration of the appropriate fractions the compound BT2053 (63 mg, 81%) as a colourless glass. $^1$H NMR (DMSO-d$_6$, 400 MHz) δ 10.83 (s, 1H), 7.82 (t, J=5.6 Hz, 1H), 7.58 (d, J=7.8 Hz, 1H), 7.42 (s, 1H), 7.35 (d, J=8.0 Hz, 1H), 7.18 (s, 1H), 7.09-7.05 (m, 1H), 7.00-6.96 (m, 1H), 6.74 (s, 1H), 3.86-3.70 (m, 6H), 3.83 (s, 3H), 3.80 (s, 3H), 3.06 (t, J=7.7 Hz, 2H), 2.43-2.38 (m, 4H), 2.35 (q, J=7.2 Hz, 2H), 1.03 (t, J=7.2 Hz, 3H); (+)-LRESIMS m/z (rel. int.) 461 (100) [M+H]$^+$; (+)-HRESIMS calcd. for $C_{26}H_{33}N_6O_2$ [M+H]$^+$ 461.2660. found 461.2657; $v_m$ 1627, 1576, 1489, 1436, 1420, 1239, 1209, 1006, 845, 739 cm$^{-1}$.

Synthesis Example 14 BT2056

Prepared according to General Procedure C from reaction of 4-methoxy-phenylboronic acid pinacol ester (60 mg, 0.25 mmol) and N-(2-(1H-indol-3-yl)ethyl)-2-chloro-6,7-dimethoxyquinazolin-4-amine (65 mg, 0.17 mmol) to afford a residue that was subjected to flash column chromatography [silica, 1:20 v/v MeOH/DCM elution] to give, after concentration of the appropriate fractions the compound BT2056 as a white powder (63 mg, 82%). $^1$H NMR (DMSO-d$_6$, 400 MHz) δ 10.86 (s, 1H), 8.47-8.43 (m, 2H), 8.10 (t, J=5.0 Hz, 1H), 7.67 (d, J=7.8 Hz, 1H), 7.62 (s, 1H), 7.38 (d, J=8.1 Hz, 1H), 7.25 (s, 1H), 7.16 (d, J=1.3 Hz, 1H), 7.10 (t, J=7.5 Hz, 1H), 7.09-6.97 (m, 3H), 3.99-3.92 (m, 2H), 3.93 (s, 3H), 3.90 (s, 3H), 3.84 (s, 3H), 3.17 (t, J=7.7 Hz, 2H); (+)-LRESIMS m/z (rel. int.) 455 (100) [M+H]$^+$; (+)-HRESIMS calcd. for $C_{27}H_{27}N_4O_3$ [M+H]$^+$ 455.2078. found 455.2083; $v_m$ 3404, 1622, 1606, 1588, 1575, 1523, 1498, 1427, 1413, 1362, 1247, 1212, 1163, 1030, 843, 742 cm$^{-1}$.

Synthesis Example 15—BT2057

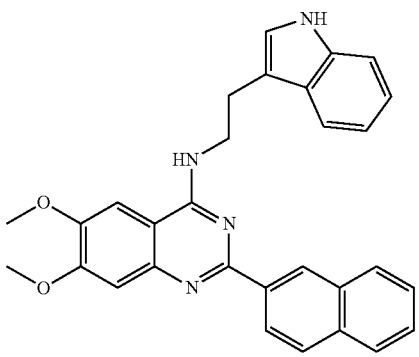 [SMILES: COc1cc2nc(-c3ccc4ccccc4c3)nc(NCCc3c[nH]c4ccccc34)c2cc1OC]

Figure 7:
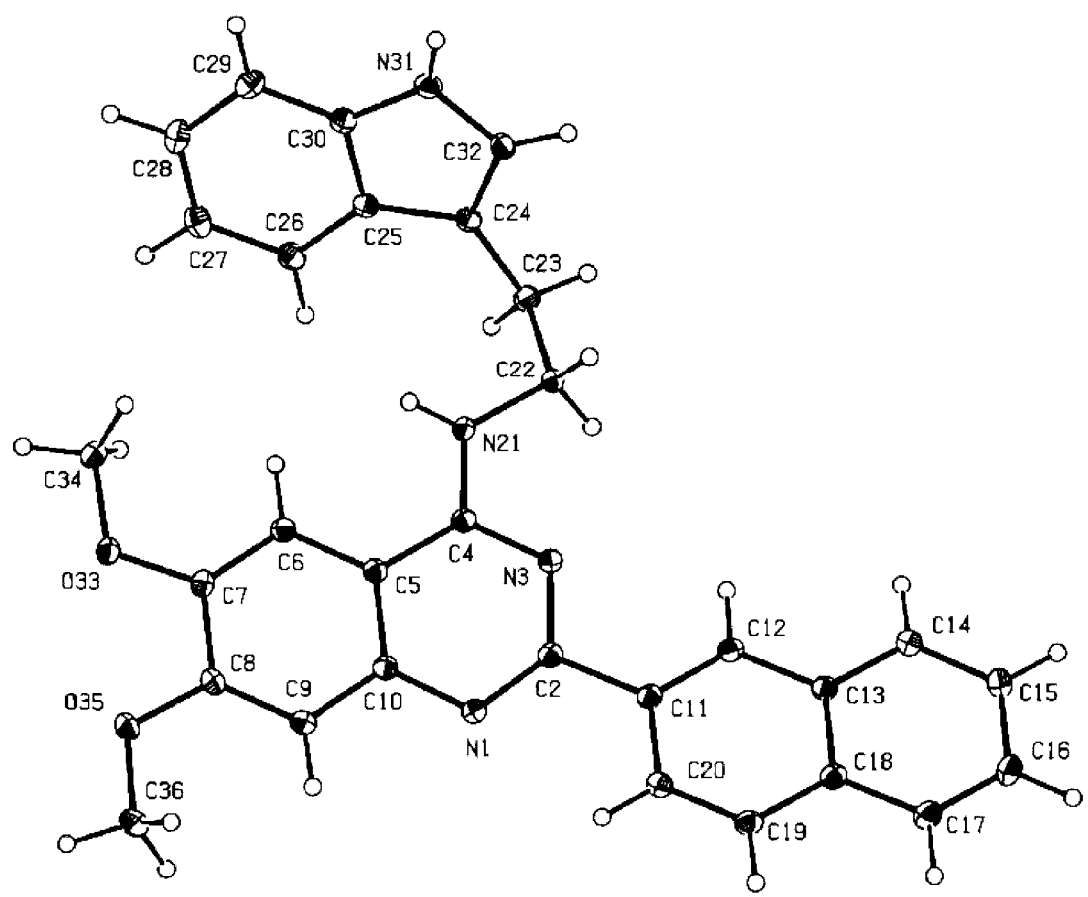
FIG. 7. X-ray crystal structure of compound BT2057. Anisotropic displacement ellipsoids display 30% probability levels. Hydrogen atoms are drawn as circles with small radii. The crystallographic asymmetric unit consists of one molecule of BT2057 and one molecule of dichloromethane. Data collection: CrysAlis PRO, Agilent Technologies, Version 1.171.37.33d (release 23 Apr. 2014 CrysAlis171 .NET) (compiled Apr. 23, 2014, 17:37:27); cell refinement: CrysAlis PRO; data reduction: CrysAlis PRO; program(s) used to solve structure: SIR92 (Altomare et al (1994) J. Appl. Cryst. 27, 435); program(s) used to refine structure: CRYSTALS (Betteridge el al (2003). J. Appl. Cryst. 36, 1487); molecular graphics: PLATON (Spek, A. L. (2008). PLATON, A Multipurpose Crystallographic Tool, Utrecht University, Utrecht, The Netherlands); software used to prepare material for publication: CRYSTALS (Betteridge et al., 2003).

Prepared according to General Procedure C from reaction of 2-naphthalene boronic acid (44 mg, 0.25 mmol) and N-(2-(1H-indol-3-yl)ethyl)-2-chloro-6,7-dimethoxyquinazolin-4-amine (65 mg, 0.17 mmol) to afford a residue that was subjected to flash column chromatography [silica, 1:5 v/v MeOH/DCM elution] to give, after concentration of the appropriate fractions the compound BT2057 as colourless needles (60 mg, 74%). Compound BT2057 was recrystallized from dichloromethane/methanol and the X-ray crystal structure is shown in FIG. 7. $^1$H NMR (DMSO-d$_6$, 400 MHz) δ 10.89 (s, 1H), 9.05 (s, 1H), 8.66 (dd, J=8.6, 1.4 Hz, 1H), 8.22 (t, J=5.5 Hz, 1H), 8.05-7.96 (m, 3H), 7.74 (d, J=7.8 Hz, 1H), 7.66 (s, 1H), 7.59-7.53 (m, 2H), 7.38 (d, J=8.1 Hz, 1H), 7.30 (d, J=2.0 Hz, 1H), 7.26 (s, 1H), 7.11 (app. t, J=7.4 Hz, 1H), 7.01 (app. t, J=7.4 Hz, 1H), 4.06-3.98 (m, 2H), 3.96 (s, 3H), 3.92 (s, 3H), 3.22 (app. t, J=7.8 Hz, 2H); $^{13}$C NMR (DMSO-d$_6$, 100 MHz) one peak overlapping δ 158.6, 157.9, 153.9, 148.3, 146.8, 136.7, 136.3, 133.7, 132.8, 128.7, 127.6, 127.5, 127.4, 127.0, 126.6, 126.2, 125.3, 122.8, 121.0, 118.4, 118.3, 112.1, 111.5, 107.5, 102.2, 56.0, 55.7, 41.8, 25.1; (+)-LRESIMS m/z (rel. int.) 475 (100) [M+H]$^+$; (+)-HRESIMS calcd. for $C_{30}H_{27}N_4O_2$ [M+H]$^+$ 475.2129. found 475.2134; $v_{max}$ 3448, 1620, 1583, 1524, 1495, 1422, 1368, 1215, 856, 787, 743, 725 cm$^{-1}$.

Synthesis Example 16 BT2059

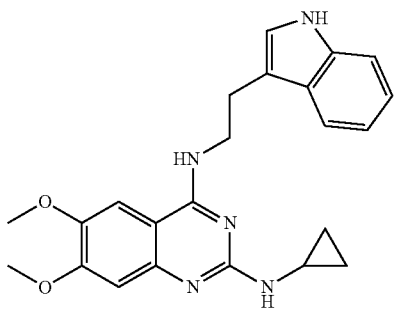 [SMILES: COc1cc2nc(NC3CC3)nc(NCCc3c[nH]c4ccccc34)c2cc1OC]

Prepared according to General Procedure D from reaction of cyclopropylamine (47 μL, 0.68 mmol) with N-(2-(1H-indol-3-yl)ethyl)-2-chloro-6,7-dimethoxyquinazolin-4-amine (65 mg, 0.17 mmol) to afford a residue that was subjected to flash column chromatography [silica, 1:10 v/v ammoniacal MeOH/DCM elution] to give, after concentration of the appropriate fractions the compound BT2059 (10 mg, 81%) as a white solid. $^1$H NMR (CDCl$_3$, 400 MHz) δ 8.28 (s, 1H), 7.67 (d, J=7.9 Hz, 1H), 7.39 (d, J=8.1 Hz, 1H), 7.21 (t, J=7.5 Hz, 1H), 7.11 (t, J=7.5 Hz, 1H), 7.07 (s, 1H), 6.91 (s, 1H), 6.58 (s, 1H), 5.64 (s, 1H), 5.52 (s, 1H), 3.96-3.90 (m, 2H), 3.89 (s, 3H), 3.73 (s, 3H), 3.17 (t, J=6.6 Hz, 2H), 2.94-2.81 (m, 1H), 0.84-0.75 (m, 2H), 0.61-0.56 (m, 2H); (+)-LRESIMS m/z (rel. int.) 404 (100) [M+H]$^+$; (+)-HRESIMS calcd. for $C_{23}H_{26}N_6O_2$ [M+H]$^+$ 404.2081. found 404.2088; $v_{max}$ 1626, 1580, 1496, 1459, 1235, 1209, 1009, 785, 740 cm$^{-1}$.

Synthesis Example 17 BT2060

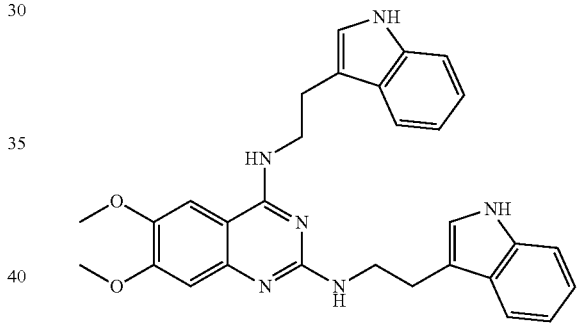

Prepared according to General Procedure D from reaction of tryptamine (109 mg, 0.68 mmol) with N-(2-(1H-indol-3-yl)ethyl)-2-chloro-6,7-dimethoxyquinazolin-4-amine (65 mg, 0.17 mmol) to afford a residue that was subjected to flash column chromatography [silica, 1:10 v/v ammoniacal MeOH/DCM elution] to give, after concentration of the appropriate fractions the compound BT2060 (22 mg, 26%) as a white solid. $^1$H NMR (CDCl$_3$, 400 MHz) δ 8.08 (s, 1H), 8.04 (s, 1H), 7.69 (d, J=8.0 Hz, 1H), 7.66 (d, J=8.0 Hz, 1H), 7.40 (dt, J=8.2, 0.8 Hz, 1H), 7.36 (dt, J=8.0, 0.8 Hz, 1H), 7.24-7.21 (m, 1H), 7.20-7.17 (m, 1H), 7.13-7.09 (m, 2H), 7.08 (d, J=2.3 Hz, 1H), 7.04 (d, J=2.3 Hz, 1H), 6.87 (s, 1H), 6.45 (s, 1H), 5.45 (s br, 2H), 3.93 (s, 3H), 3.92-3.81 (m, 4H), 3.73 (s, 3H); 3.15 (t, J=6.5 Hz, 2H), 3.12 (t, J=6.5 Hz, 2H); (+)-LRESIMS m/z (rel. int.) 507 (100) [M+H]$^+$; (+)-HRESIMS calcd. for $C_{30}H_{31}N_6O_2$ [M+H]$^+$ 507.2503. found 507.2508; $v_m$ 1644, 1580, 1502, 1454, 1231, 1210, 739 cm$^{-1}$.

Synthesis Example 18 BT2062

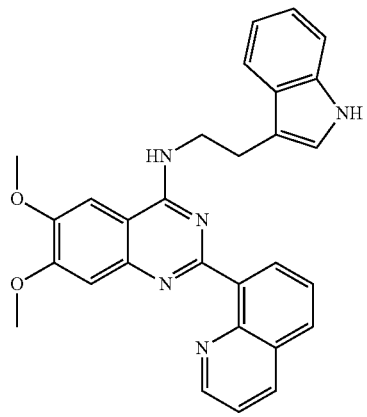 [SMILES: COc1cc2nc(-c3cccc4cccnc34)nc(NCCc3c[nH]c4ccccc34)c2cc1OC]

Prepared according to General Procedure C from reaction of 8-quinoline boronic acid (44 mg, 0.25 mmol) and N-(2-(1H-indol-3-yl)ethyl)-2-chloro-6,7-dimethoxyquinazolin-4-amine (65 mg, 0.17 mmol) to afford a residue that was subjected to flash column chromatography [silica, 1:30 v/v MeOH/DCM elution] to give, after concentration of the appropriate fractions the compound BT2062 as colourless needles (55 mg, 68%). $^1$H NMR (DMSO-$d_6$, 400 MHz) δ 10.72 (s, 1H), 8.82 (dd, J=4.1, 1.5 Hz, 1H), 8.43 (dd, J=8.3, 1.5 Hz, 1H), 8.17 (t, J=5.4 Hz, 1H), 8.06 (d, J=8.1 Hz, 1H), 7.87 (d, J=6.9 Hz, 1H), 7.70 (d, J=7.7 Hz, 1H), 7.67 (s, 1H), 7.51 (dd, J=8.3, 4.1 Hz, 1H), 7.37 (d, J=7.7 Hz, 1H), 7.25 (d, J=8.1 Hz, 1H), 7.16 (s, 1H), 7.11 (d, J=1.7 Hz, 1H), 6.94 (t, J=7.5 Hz, 1H), 6.54 (t, J=7.5 Hz, 1H), 3.93 (s, 3H), 3.90 (s, 3H), 3.76-3.66 (m, 2H), 3.07 (app. t, J=7.7 Hz, 2H); $^{13}$C NMR (DMSO-$d_6$, 100 MHz) δ 161.5, 158.1, 153.8, 150.1, 148.2, 146.2, 145.9, 140.5, 136.2, 136.1, 129.5, 128.2, 128.0, 127.3, 125.9, 122.5, 121.2, 120.7, 118.6, 117.8, 112.1, 111.1, 107.2, 107.1, 102.0, 56.0, 55.7, 41.7, 24.9; (+)-LRESIMS m/z (rel. int.) 476 (100) [M+H]$^+$; (+)-HRESIMS calcd. for $C_{29}H_{26}N_6O_2$ [M+H]$^+$ 476.2081. found 476.2087; $v_{max}$ 1622, 1585, 1524, 1502, 1419, 1356, 1219, 851, 797, 745, 639 cm$^{-1}$.

Synthesis Example 19 BT2090

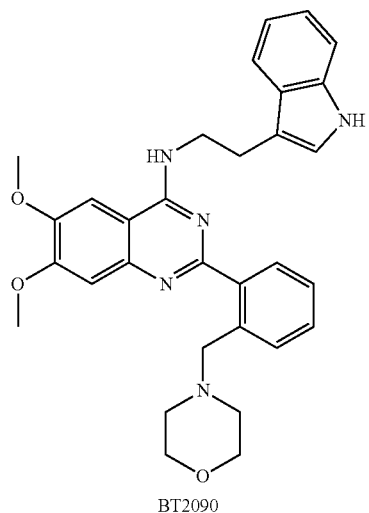

BT2090

Prepared according to General Procedure C from reaction of 4-(2-(4,4,5,5-tetramethyl-1,3,2-dioxaborolan-2-yl)benzyl)morpholine (119 mg, 0.39 mmol) and N-(2-(1H-indol-3-yl)ethyl)-2-chloro-6,7-dimethoxyquinazolin-4-amine (100 mg, 0.26 mmol) to afford a residue that was subjected to flash column chromatography [silica, 1:10 ammoniacal MeOH/DCM elution] to give, after concentration of the appropriate fractions BT2090 as a white powder (57 mg, 42%). $^1$H NMR (400 MHz, DMSO-$d_6$) δ 10.81 (s, 1H), 8.15 (s, 1H), 7.74 (d, J=7.5 Hz, 1H), 7.65 (s, 1H), 7.59 (d, J=7.9 Hz, 1H), 7.55 (dd, J=7.5, 0.8 Hz, 1H), 7.43-7.29 (m, 3H), 7.18 (d, J=2.3 Hz, 1H), 7.15 (s, 1H), 7.04 (ddd, J=8.0, 6.9, 1.1 Hz, 1H), 6.84 (ddd, J=8.0, 6.9, 1.0 Hz, 1H), 3.98-3.88 (m, 8H), 3.35-3.27 (m, 4H), 3.87-3.80 (m, 2H), 3.14-3.06 (m, 2H), 2.21-2.10 (m, 4H); (+)-LRESIMS m/z (rel. int.) 524 (100) [M+H]$^+$; (+)-HRESIMS calcd. for $C_{31}H_{34}N_5O_3$ [M+H]$^+$ 524.2656. found 524.2662.

Synthesis Example 20 BT2120

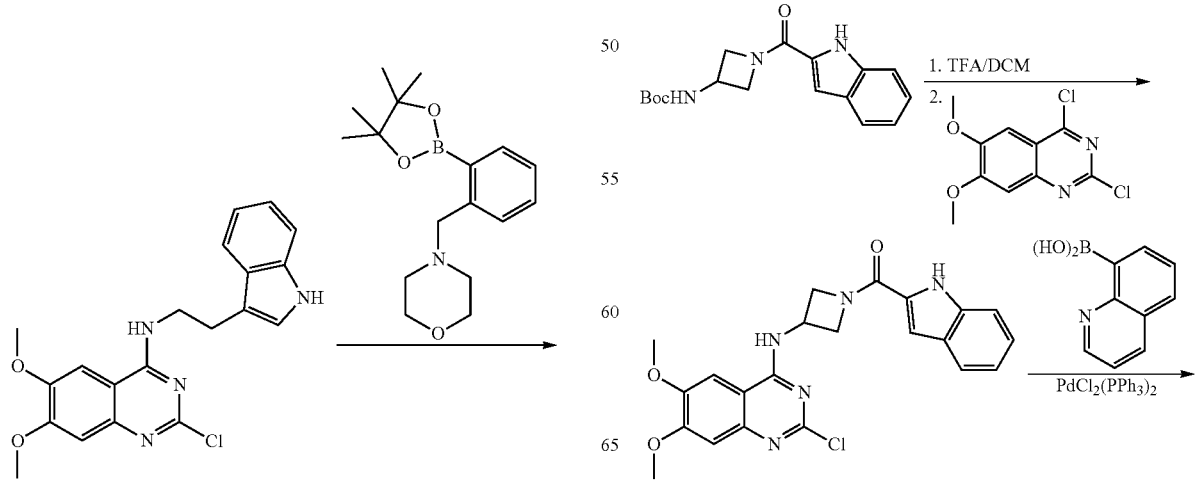

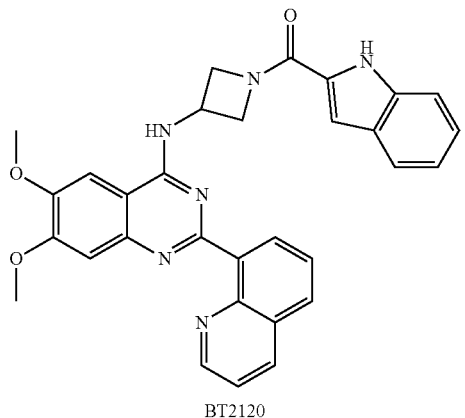

BT2120 tert-Butyl (1-(1H-indole-2-carbonyl)azetidin-3-yl)carbamate (383 mg, 1.22 mmol) was deprotected following General Procedure F with TFA (2.0 mL) and DCM (8.0 mL) to afford after trituration with ether (10 mL) the TFA salt of (3-aminoazetidin-1-yl)(1H-indol-2-yl)methanone (348 mg, 87%) as a gum that was used directly in the next step without further purification. A magnetically stirred solution of the TFA-salt in DMF (5 mL), cooled to 0° C. was treated with 2,4-dichloro-6,7-dimethoxyquinazoline (274 mg, 1.06 mmol) followed by dropwise addition of triethylamine (595 µL, 4.24 mmol). The mixture was stirred at 0° C. for 5 h then a further 18 h at 18° C. The precipitate was collected by vacuum filtration and washed with DMF (5 mL) then ether (15 mL) to afford (3-((2-chloro-6,7-dimethoxyquinazolin-4-yl)amino)azetidin-1-yl)(1H-indol-2-yl)methanone (329 mg, 71%) as a white powder and used without further purification. $^1$H NMR (400 MHz, DMSO-d$_6$) δ 11.66 (s, 1H), 8.89 (d, J=6.4 Hz, 1H), 7.72 (s, 1H), 7.63 (d, J=8.0 Hz, 1H), 7.45 (d, J=8.3 Hz, 1H), 7.20 (t, J=8.0 Hz, 1H), 7.12 (s, 1H), 7.05 (t, J=7.3 Hz, 1H), 6.90-6.86 (m, 1H), 5.14-5.01 (m, 1H), 5.00-4.92 (m, 1H), 4.62-4.46 (m, 2H), 4.32-4.18 (m, 1H), 3.91 (s, 3H), 3.90 (s, 3H). (+)-LRESIMS m/z (rel. int.) 438 (80) [M+H]$^+$, 460 (100) [M+Na]$^+$; $v_{max}$ 3303, 1617, 1577, 1541, 1516, 1452, 1432, 1240, 1149, 960, 736 cm$^{-1}$. The product formed directly above (100 mg, 0.23 mmol) was subjected to a palladium catalysed Suzuki-Miyaura reaction and reacted with 8-quinoline boronic acid (59 mg, 0.35 mmol) according to General Procedure C to afford a residue that was subjected to flash column chromatography [silica, 1:10 MeOH:DCM] to give, after concentration of the appropriate fractions BT2120 (75 mg, 61%) as white crystals. $^1$H NMR (400 MHz, DMSO-d$_6$) δ 11.63 (s, 1H), 8.94 (dd, J=4.4, 1.7 Hz, 1H), 8.70 (s, 1H), 8.49 (d, J=8.5 Hz, 1H), 8.15-8.04 (m, 2H), 7.78 (s, 1H), 7.72 (t, J=7.6 Hz, 1H), 7.66-7.59 (m, 2H), 7.44 (d, J=8.3 Hz, 1H), 7.30 (s, 1H), 7.20 (t, J=7.6 Hz, 1H), 7.05 (t, J=7.5 Hz, 1H), 6.83 (d, J=1.7 Hz, 1H), 5.14-5.02 (m, 1H), 4.90-4.80 (m, 1H), 4.64-4.55 (m, 1H), 4.50-4.41 (m, 1H), 4.32-4.24 (m, 1H), 3.96 (s, 3H), 3.93 (s, 3H). (+)-LRESIMS m/z (rel. int.) 531 (100) [M+H]$^+$; $v_{max}$ 3248, 1602, 1586, 1519, 1499, 1447, 1416, 1218, 794, 743 639 cm$^{-1}$.

Synthesis Example 21 BT2148

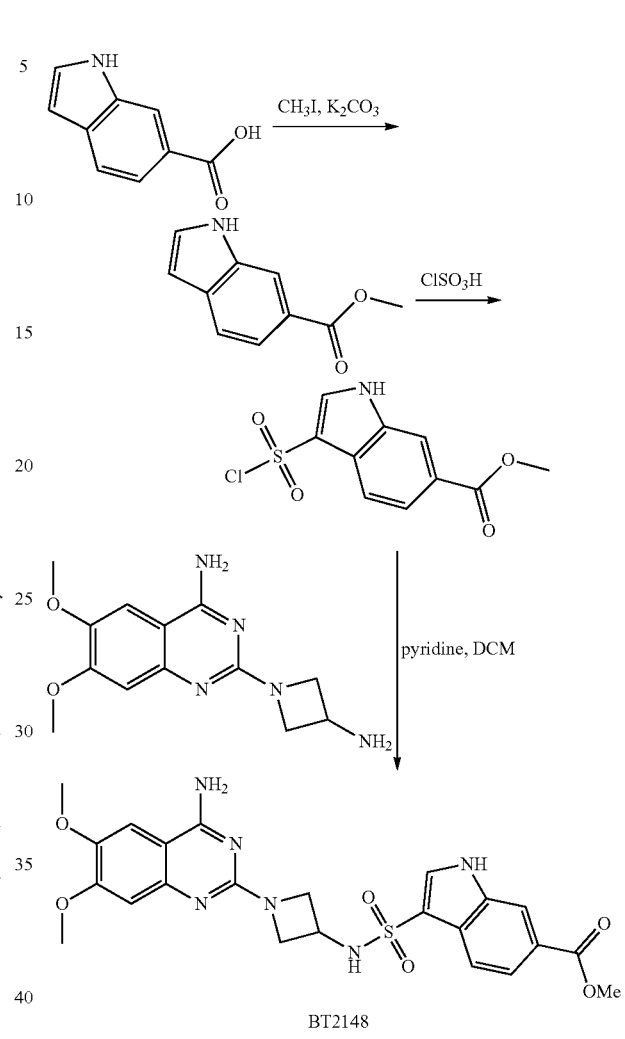

BT2148

Methyl 1H-indole-6-carboxylate

A magnetically stirred solution of 1H-indole-6-carboxylic acid (5.00 g, 31.02 mmol) in DMF (40 mL) was treated with potassium carbonate (4.29 g, 31.02 mmol) and dropwise with methyl iodide (1.93 mL, 31.02 mmol). After stirring at room temperature for 3 h, the resulting mixture was diluted with diethyl ether (150 mL) then washed with water (2×100 mL) before being dried over magnesium sulphate, filtered and concentrated under reduced pressure. The ensuing residue was subjected to flash chromatography [silica, 20:80 v/v diethyl ether/hexane] and concentration of the appropriate fractions (R$_f$=0.42) afforded methyl 1H-indole-6-carboxylate (4.29 g, 83%) as a light yellow crystalline solid. $^1$H NMR (400 MHz, chloroform-d) δ 8.71 (brs, 1H), 8.19 (s, 1H), 7.84 (dd, J=8.4 and 1.3 Hz, 1H), 7.67 (d, J=8.4 Hz, 1H), 7.37 (t, J=2.8 Hz, 1H), 6.60 (s, 1H), 3.95 (s, 3H); $^{13}$C NMR (100 MHz, chloroform-d) δ 168.5, 135.3, 131.7, 127.8, 123.6, 120.9, 120.4, 113.7, 103.0, 52.1; (+)-LRESIMS m/z (rel. int.) 198 (100) [M+Na]$^+$; $v_{max}$ 3337, 1680, 1617, 1569, 1508, 1438, 1335, 1290, 1262, 1220, 1205, 1128, 1115, 1084, 982, 911, 828, 775, 736, 659 cm$^{-1}$.

Methyl 3-(chlorosulfonyl)-1H-indole-6-carboxylate

Methyl 1H-indole-6-carboxylate (1.10 g, 6.28 mmol) was added in small portions to chlorosulfonic acid (2 mL) with intensive stirring. After 15 min, the mixture was carefully pipetted out into a flask placed in an ice bath containing ethyl acetate (30 mL). Then the resulting mixture was slowly poured into ice and the separated aqueous layer was extracted with ethyl acetate (3×30 mL). The combined organic phase was washed with $NaHCO_3$ (a saturated aqueous solution, 1×50 mL), brine (1×50 mL) before being dried over magnesium sulphate, filtered and concentrated under reduced pressure. The ensuing residue was subjected to flash chromatography (silica, 80:20 v/v diethyl ether/hexane) and concentration of the appropriate fractions ($R_f$=0.36, 80:20 v/v diethyl ether/hexane) afforded methyl 3-(chlorosulfonyl)-1H-indole-6-carboxylate (1.10 g, 64%) as a yellow crystalline solid. $^1$H NMR (400 MHz, acetone-$d_6$) δ 12.08 (s, 1H), 8.55 (d, J=3.4 Hz, 1H), 8.35 (s, 1H), 8.05 (dd, J=8.5 and 1.3 Hz, 1H), 8.00 (d, J=8.5 Hz, 1H), 3.92 (s, 3H); $^{13}$C NMR (100 MHz, acetone-$d_6$) δ 167.1, 136.6, 136.2, 127.4, 126.7, 124.8, 120.0, 119.6, 116.1, 52.5; (+)-LRESIMS m/z (rel. int.) 270 (70) [M-Cl+MeOH]$^+$; $v_{max}$ 3287, 1710, 1625, 1495, 1438, 1367, 1311, 1294, 1215, 1159, 1116, 1087, 1018, 766 cm$^{-1}$.

BT2148

A solution of methyl 3-(chlorosulfonyl)-1H-indole-6-carboxylate (149.1 mg, 0.54 mmol) in dichloromethane (3 mL) was treated with a solution of 2-(3-aminoazetidin-1-yl)-6,7-dimethoxyquinazolin-4-amine (50 mg, 0.18 mmol) in pyridine (0.5 mL) at 0° C. After 30 min, the resulting mixture was allowed to warm up to 20° C. for 2 h. Solvent was evaporated and the residue thus obtained was subjected to flash column chromatography [silica, 10:90 v/v methanol/dichloromethane elution] to give, after concentration of the appropriate fractions ($R_f$=0.22), BT2148 as a white solid (75 mg, 75%). $^1$H NMR (400 MHz, acetone-$d_6$) δ 11.57 (s, 1H), 8.33 (s, 1H), 8.15 (s, 1H), 8.03 (d, J=8.5 Hz, 1H), 7.91 (dd, J=8.5 and 1.4 Hz, 1H), 7.32 (s, 1H), 7.17 (d, J=9.5 Hz, 1H), 6.74 (s, 1H), 6.57 (s, 1H), 4.31 (m, 1H), 4.02 (t, J=8.2 Hz, 2H), 3.91 (s, 3H), 3.83 (s, 3H), 3.79 (s, 3H), 3.64 (dd, J=8.9 and 5.7 Hz, 2H); (+)-LRESIMS m/z (rel. int.) 513 (100) [M+H]$^+$; HRMS (ESI, +ve) Found: [M+H]$^+$ 513.1555, $C_{23}H_{25}N_6O_6S$ requires 513.1556; $v_{max}$ 3180, 1703, 1649, 1625, 1565, 1486, 1455, 1438, 1380, 1311, 1241, 1210, 1140, 1105, 1019, 999, 844, 768 cm$^{-1}$.

Synthesis Example 22 BT2162 and BT2172

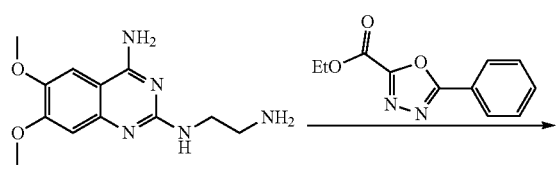

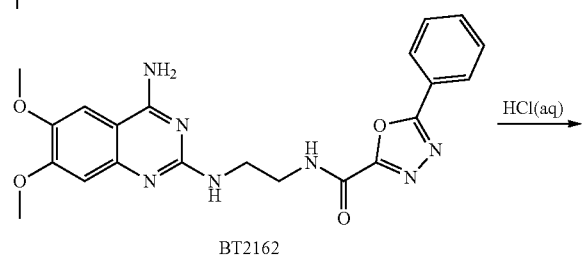

BT2162

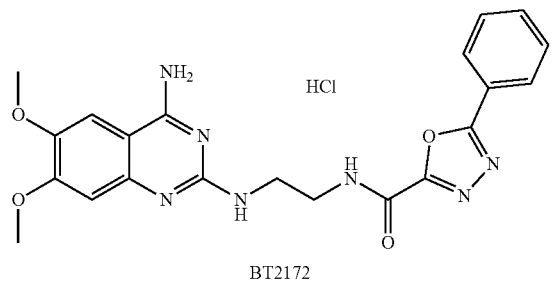

BT2172

According to General Procedure E, a solution of N$^2$-(2-aminoethyl)-6,7-dimethoxyquinazoline-2,4-diamine (120.7 mg, 0.46 mmol), ethyl 5-phenyl-1,3,4-oxadiazole-2-carboxylate (50.0 mg, 0.23 mmol) prepared according to the procedure of Dost, et al. (J. Prakt. Chem. 1985, 327, 109) in ethanol (1 mL) was irradiated at 80° C. for 3 h. BT2162 (91.0 mg, 91%) ($R_f$=0.24, 10:90 v/v methanol/dichloromethane) was obtained as a white solid. $^1$H NMR (400 MHz, DMSO-$d_6$) δ 9.93 (brs, 1H), 8.04 (d, J=7.1 Hz, 2H), 7.67 (m, 1H), 7.61 (m, 2H), 7.43 (s, 1H), 7.16 (brs, 2H), 6.91 (s, 1H), 6.52 (brs, 1H), 3.86 (s, 3H), 3.78 (s, 3H), 3.51 (s, 4H); $^{13}$C NMR (100 MHz, DMSO-$d_6$) δ 164.9, 161.2, 159.1, 158.6, 154.1, 153.1, 147.8, 144.8, 132.6, 129.5 (2C), 127.0 (2C), 122.8, 104.8, 103.9, 103.3, 55.9, 55.4, 41.2, 39.9; (+)-LRESIMS m/z (rel. int.) 436 (100) [M+H]$^+$; HRMS (ESI, +ve) Found: (M+H) 436.1719, $C_{21}H_{22}N_7O_4$ requires 436.1733; $v_{max}$ 3246, 2969, 1675, 1648, 1601, 1578, 1547, 1503, 1451, 1384, 1366, 1318, 1276, 1235, 1210, 1112, 1006, 829, 709 cm$^{-1}$.

BT2172

A magnetically stirred suspension of BT2162 (22.5 mg, 52 μmol) in dioxane (3 mL) maintained at 0° C. (ice water bath) was treated dropwise with a solution of HCl (100 μL, 4 M in dioxane). The mixture was stirred for 5 min then concentrated by a gentle stream of nitrogen then the solid triturated with ether (2 mL) and the residue held under high vacuum for 1 h to afford BT2172 (20 mg, 82%), the hydrochloride salt of BT2162 as a white powder. $^1$H NMR (400 MHz, DMSO-$d_6$) δ 12.28 (br s, 1H), 9.47 (t, J=5.7 Hz, 1H), 8.81 (br s, 1H), 8.60 (br s, 1H), 8.07 (d, J=7.6 Hz, 2H), 7.86 (br s, 1H), 7.74-7.56 (m, 4H), 7.00 (br s, 1H), 3.88 (s, 3H), 3.82 (s, 3H), 3.65-3.61 (m, 2H), 3.59-3.55 (m, 2H); (+)-LRESIMS m/z (rel. int.) 436 [(M+H)$^+$, 100%].

Synthesis Example 23 BT2164

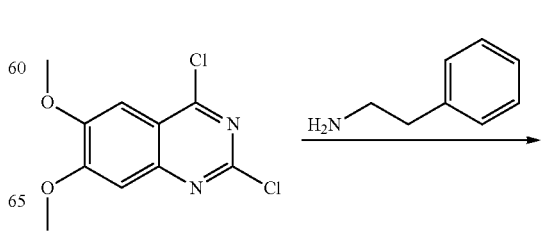

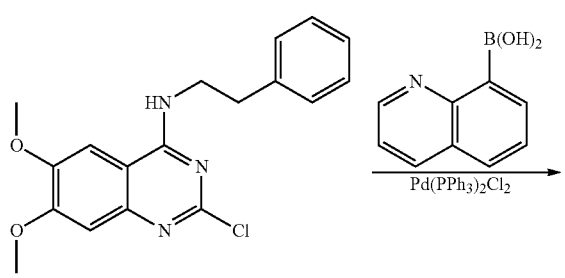

158.5, 157.9, 154.9, 150.4, 149.4, 146.0, 139.7, 137.7, 132.3, 132.1, 131.1, 129.1 (2C), 128.8, 128.5 (2C), 126.7, 126.3, 121.6, 107.4, 104.1, 103.1, 56.9, 56.6, 43.1, 35.3; MS (ESI, +ve) m/z 437.1 [(M+H), 100%]; HRMS (ESI, +ve) Found: (M+H)$^+$437.1978, $C_{27}H_{25}N_4O_2$ requires 437.1978; $v_{max}$ 3393, 3235, 3027, 1625, 1597, 1549, 1514, 1479, 1401, 1279, 1232, 1126, 1036, 794 cm$^{-1}$.

Synthesis Example 24 BT2167

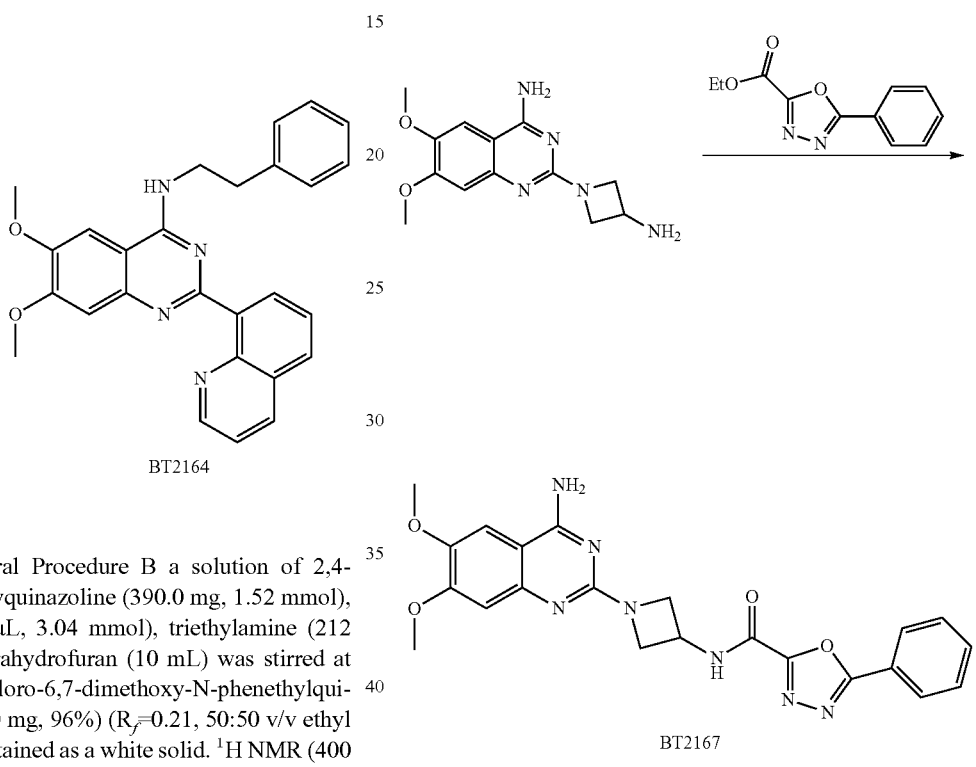

According to General Procedure B a solution of 2,4-dichloro-6,7-dimethoxyquinazoline (390.0 mg, 1.52 mmol), phenethylamine (382 μL, 3.04 mmol), triethylamine (212 μL, 1.52 mmol) in tetrahydrofuran (10 mL) was stirred at 18° C. for 18 h. 2-Chloro-6,7-dimethoxy-N-phenethylquinazolin-4-amine (500.0 mg, 96%) ($R_f$=0.21, 50:50 v/v ethyl acetate/hexane) was obtained as a white solid. $^1$H NMR (400 MHz, chloroform-d) δ 7.30-7.27 (m, 2H), 7.20-7.23 (m, 3H), 7.03 (s, 1H), 6.88 (s, 1H), 6.26 (t, J=5.7 Hz, 1H), 3.87-3.91 (m, overlapped, 2H), 3.88 (s, 3H), 3.83 (s, 3H), 3.00 (t, J=7.1 Hz, 2H); $^{13}$C NMR (101 MHz, chloroform-d) δ 159.9, 156.2, 154.9, 149.0, 147.8, 138.7, 128.9 (2C), 128.7 (2C), 126.7, 106.9, 106.9, 100.0, 56.2, 56.1, 42.6, 35.2; MS (ESI, +ve) m/z 366.1 [(M+Na), 100%]; $v_{max}$ 3399, 3279, 2936, 1621, 1582, 1530, 1508, 1454, 1425, 1340, 1240, 1221, 1146, 942, 851, 750, 700 cm$^{-1}$. According to General Procedure C, a solution of 2-chloro-6,7-dimethoxy-N-phenethylquinazolin-4-amine (50.0 mg, 0.14 mmol), quinolin-8-ylboronic acid (37.7 mg, 0.21 mmol), $K_2CO_3$ (100.5 mg, 0.72 mmol) and Pd(PPh$_3$)$_2$Cl$_2$ (5.1 mg, 0.007 mmol) in dimethoxyethane-water-ethanol (2 mL) was irradiated at 120° C. for 25 min. BT2164 (60.0 mg, 94%) ($R_f$=0.33, 10:90 v/v methanol/dichloromethane) was obtained as a yellow green solid. $^1$H NMR (400 MHz, chloroform-d) δ 9.74 (brs, NH), 9.07 (s, 1H), 8.67 (d, J=7.4 Hz, 1H), 8.31 (d, J=8.0 Hz, 1H), 8.03 (d, J=8.0 Hz, 1H), 8.00 (s, 1H), 7.69 (t, J=7.7 Hz, 1H), 7.52 (dd, J=8.3, 4.0 Hz, 1H), 7.32 (s, 1H), 7.16-7.24 (m, 5H), 4.05 (s, 3H), 3.98 (s, 3H), 3.81 (t, J=7.5 Hz, 2H), 3.07 (t, J=7.5 Hz, 2H); $^{13}$C NMR (101 MHz, chloroform-d) δ

According to General Procedure E, a solution of 2-(3-aminoazetidin-1-yl)-6,7-dimethoxyquinazolin-4-amine (100.0 mg, 0.36 mmol), ethyl 5-phenyl-1,3,4-oxadiazole-2-carboxylate (52.8 mg, 0.24 mmol) in ethanol (1 mL) was irradiated at 80° C. for 4 h. BT2167 (40.0 mg, 25%) ($R_f$=0.28, 5:95 v/v methanol/dichloromethane) was obtained as white solid. $^1$H NMR (400 MHz, DMSO-d$_6$) δ 9.98 (d, J=7.2 Hz, 1H), 8.11 (m, 2H), 7.66 (m, 3H), 7.44 (s, 1H), 7.26 (brs, 2H), 6.79 (s, 1H), 4.81 (h, J=7.3 Hz, 1H), 4.29 (t, J=8.2 Hz, 2H), 4.08 (dd, J=8.6 and 5.7 Hz, 2H), 3.83 (s, 3H), 3.79 (s, 3H); $^{13}$C NMR (100 MHz, DMSO-d$_6$) δ 164.9, 161.3, 160.3, 158.3, 154.2, 152.8, 148.5, 145.0, 132.7, 129.5 (2C), 127.1 (2C), 122.7, 105.0, 103.7, 103.1, 56.4 (2C), 55.8, 55.5, 39.9; (+)-LRESIMS m/z (rel. int.) 448 [(M+H)$^+$, 100%]; HRMS (ESI, +ve) Found: (M+H)$^+$448.1732, $C_{22}H_{22}N_7O_4$ requires 448.1733; $v_m$3341, 2871, 2393, 1672, 1651, 1624, 1556, 1479, 1452, 1434, 1414, 1377, 1336, 1240, 1214, 1005, 851 cm$^{-1}$.

Synthesis Example 26 BT2169 and BT2173

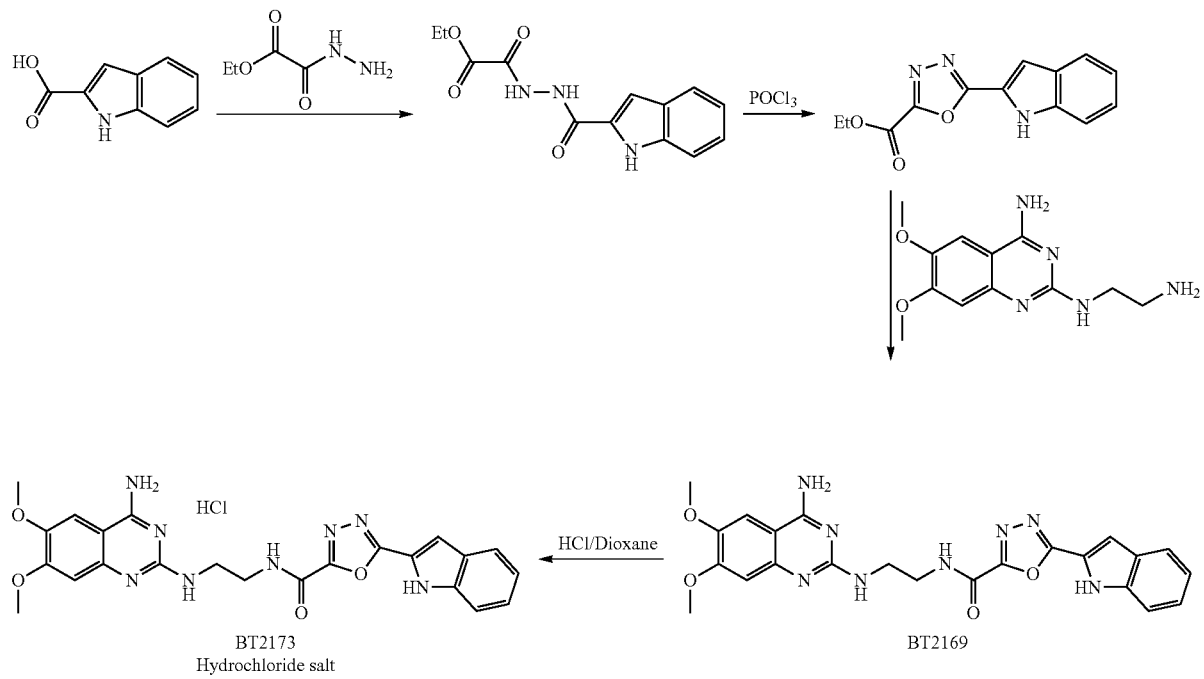

A magnetically stirred suspension of 1H-indole-2-carboxylic acid (3.56 g, 22.1 mmol) in DCM (80 mL) at 0° C. was treated with oxalyl chloride (1.99 mL, 23.2 mmol) dropwise, followed by DMF (1 drop). The mixture was stirred at 0° C. for 1 h and then the cold-bath was removed and stirring was continued at rt for 1 h. The clear solution was then concentrated with a gentle stream of nitrogen with heating, in a water bath at 40° C. The resulting tan coloured powder was then placed under high vacuum (1 mm Hg) for 1 h and redissolved in dioxane (60 mL) and ethyl 2-hydrazinyl-2-oxoacetate (2.92 g, 22.1 mmol) was added dropwise followed by sodium hydrogen carbonate (1.86, 22.1 mmol) and then magnetically stirred at 45-50° C. for 18 h. The mixture was then filtered and the filtrate concentrated in vacuo to afford a tan coloured solid which was washed with cold ether (15 mL) to afford ethyl 2-(2-(1H-indole-2-carbonyl)hydrazinyl)-2-oxoacetate (2.08 g) and used directly without further purification. MS (ESI, +ve) m/z 298 [(M+Na), 100%]. A portion of the above formed product (1.00 g, 3.64 mmol) was suspended in phosphoryl chloride (5 mL) and magnetically stirred under an atmosphere of nitrogen at 65° C. for 4 h. The phosphoryl chloride was removed by short-path distillation under high vacuum, and water (100 mL, ice-cold) was added and stirred for 0.2 h. The orange-coloured precipitate was collected and purified by flash chromatography (1:10 v/v diethyl ether/dichloromethane) to provide ethyl 5-(1H-indol-2-yl)-1,3,4-oxadiazole-2-carboxylate (351 mg, 38%) as a yellow powder. $^1$H NMR (400 MHz, CDCl$_3$) δ 9.71 (s, 1H), 7.72 (d, J=8.1 Hz, 1H), 7.60 (d, J=8.3 Hz, 1H), 7.42-7.35 (m, 2H), 7.20 (app. t, J=7.6 Hz, 1H), 4.58 (q, J=7.1 Hz, 2H), 1.50 (t, J=7.1 Hz, 3H); 13C NMR (100 MHz, CDCl$_3$) δ 161.4, 155.9, 154.2, 137.9, 127.6, 126.0, 122.2, 121.4, 119.7, 112.2, 108.4, 63.6, 14.1; MS (ESI, +ve) m/z 280 [(M+Na), 100%].

According to General Procedure E, a solution of N$^2$-(2-aminoethyl)-6,7-dimethoxyquinazoline-2,4-diamine (102.4 mg, 0.38 mmol), ethyl 5-(1H-indol-2-yl)-1,3,4-oxadiazole-2-carboxylate (50.0 mg, 0.19 mmol) in ethanol (1 mL) was irradiated at 80° C. for 3 h. BT2169 (80.0 mg, 87%) (R$_f$=0.22, 15:85 v/v methanol/dichloromethane) was obtained as a white solid. $^1$H NMR (400 MHz, DMSO-d$_6$) δ 12.37 (s, 1H), 9.93 (s, 1H), 7.69 (d, J=8.0 Hz, 1H), 7.49 (d, J=8.3 Hz, 1H), 7.45 (s, 1H), 7.29 (t, overlapped, J=7.2 Hz, 1H), 7.26 (s, overlapped, 1H), 7.21 (brs, overlapped, NH$_2$), 7.11 (t, J=7.5 Hz, 1H), 6.93 (s, 1H), 6.57 (brs, 1H), 3.88 (s, 3H), 3.79 (s, 3H), 3.52 (s, 4H); $^{13}$C NMR (100 MHz, DMSO-d$_6$) δ 161.3, 160.3, 158.8, 157.9, 154.2, 153.1, 147.6, 144.9, 138.0, 127.2, 124.6, 121.7, 120.5, 120.4, 112.4, 106.1, 104.8, 104.0, 103.3, 55.9, 55.5, 41.4, 39.9; (+)-LRESIMS m/z (rel. int.) 475 [(M-FH)$^+$, 100%]; HRMS (ESI, +ve) Found: (M-FH)$^+$448.1732, C$_{22}$H$_{22}$N$_7$O$_4$ requires 448.1733. ν$_{max}$ 3465, 3331, 3216, 3158, 2966, 1681, 1636, 1609, 1572, 1505, 1484, 1460, 1397, 1346, 1320, 1277, 1238, 1228, 1212, 1183, 1109, 1007, 831, 814, 736 cm$^{-1}$.
BT2173

A magnetically stirred suspension of BT2169 (21.7 mg, 52 μmol) in dioxane (3 mL) maintained at 0° C. (ice water bath) was treated dropwise with a solution of HCl (100 μL, 4 M in dioxane). The mixture was stirred for 5 min then concentrated by a gentle stream of nitrogen then the solid triturated with ether (2 mL) and the residue held under high vacuum for 1 h to afford BT2173 (19.5 mg, 82%), the hydrochloride salt of BT2169 as a white powder. $^1$H NMR (400 MHz, DMSO-d$_6$) One NH not observed δ 12.42 (s, 1H), 9.47 (t, J=5.7 Hz, 1H), 8.84 (brs, 1H), 8.62 (brs, 1H), 7.89 (s, 1H), 7.72 (s, 1H), 7.69 (d, J=8.2 Hz, 1H), 7.49 (d, J=8.3 Hz, 1H), 7.32-7.26 (m, 2H), 7.12 (t, J=7.5 Hz, 1H), 6.99 (br s, 1H), 3.89 (s, 3H), 3.82 (s, 3H), 3.71-3.61 (m, 2H), 3.64-3.53 (m, 2H).

Synthesis Example 26 BT2170

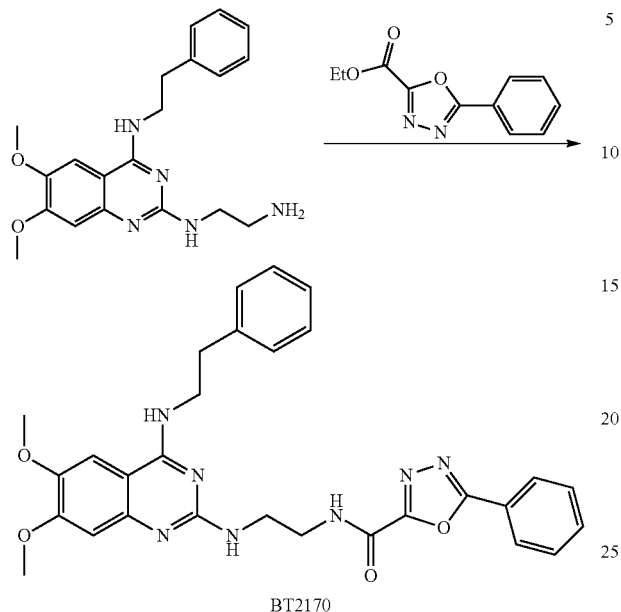

BT2170

According to General Procedure E, a solution of $N^2$-(2-aminoethyl)-6,7-dimethoxy-$N^4$-phenethylquinazoline-2,4-diamine (101 mg, 0.24 mmol), ethyl 5-(1H-indol-2-yl)-1,3,4-oxadiazole-2-carboxylate (30.0 mg, 0.14 mmol) in ethanol (1 mL) was irradiated at 80° C. for 3 h. BT2170 (70.0 mg, 94%) ($R_f$=0.14, 3.5:96.5 v/v methanol saturated ammonia/dichloromethane) was obtained as a yellow solid. $^1$H NMR (400 MHz, chloroform-d) δ 10.45 (s, NH), 8.03 (d, J=7.5 Hz, 2H), 7.58-7.37 (m, 4H), 7.31-7.14 (m, 5H), 6.59 (s, 1H), 5.40 (brs, overlapped, NH), (brs, overlapped, NH), 4.11 (s, 3H), 3.81 (s, 3H), 3.77 (q, overlapped, J=6.6 Hz, 2H), 3.70 (s, 4H), 2.94 (t, J=7.0 Hz, 2H); $^{13}$C NMR (100 MHz, chloroform-d) δ 166.0, 159.9, 159.3, 159.0, 154.80, 153.8, 148.1, 146.0, 139.3, 132.4, 129.2 (2C), 129.0 (2C), 128.8 (2C), 127.5 (2C), 126.7, 123.2, 106.9, 104.1, 100.4, 56.6, 56.2, 44.2, 42.3, 41.1, 35.6; (+)-LRESIMS m/z (rel. int.) 540.3 (100) [M+H]$^+$; HRMS (ESI, +ve) Found: [M+H]$^+$ 540.2356, $C_{29}H_{30}N_7O_4$ requires 540.2359. [M+Na]' 562.2182, $C_{29}H_{29}N_7O_4Na$ requires 562.2179; $v_{max}$ 3402, 2934, 1680, 1626, 1582, 1547, 1504, 1474, 1451, 1354, 1316, 1250, 1233, 1213, 1014, 855, 710 cm$^{-1}$.

Synthesis Example 27 BT2171

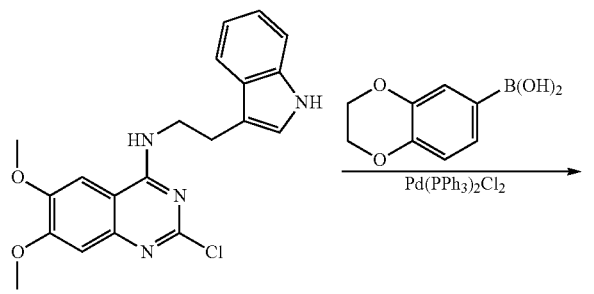

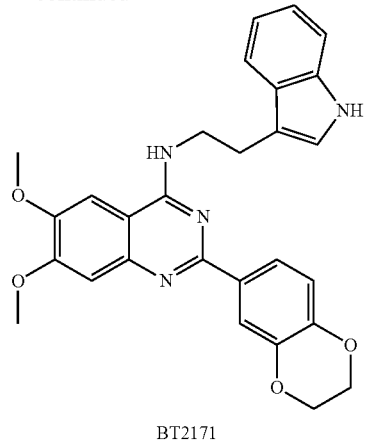

BT2171

According to General Procedure C, a solution of N-(2-(1H-indol-3-yl)ethyl)-2-chloro-6,7-dimethoxyquinazolin-4-amine (50.0 mg, 0.13 mmol), 1,4-benzodioxane-6-boronic acid (35.5 mg, 0.19 mmol), $K_2CO_3$ (90.2 mg, 0.65 mmol) and Pd(PPh$_3$)$_2$Cl$_2$ (4.6 mg, 0.006 (5) mmol) in dimethoxyethane-water-ethanol (2 mL) was irradiated at 120° C. for 25 min. BT2171 (40.0 mg, 63%) ($R_f$=0.25, 70:30 v/v ethyl acetate/hexane) was obtained as a white solid. $^1$H NMR (400 MHz, DMSO-d$_6$) δ 10.86 (s, NH), 8.11 (t, J=5.5 Hz, NH), 8.03-7.98 (m, 2H), 7.67 (d, J=7.8 Hz, 1H), 7.61 (s, 1H), 7.37 (d, J=8.0 Hz, 1H), 7.24 (d, J=2.2 Hz, 1H), 7.15 (s, 1H), 7.09 (t, J=8.0 Hz, 1H), 7.01 (t, J=7.8 Hz, 1H), 6.94 (d, J=8.4 Hz, 1H), 4.30 (s, 4H), 3.93 (s, 3H), 3.91 (m, overlapped, 2H), 3.89 (s, 3H), 3.16 (m, overlapped, 2H); $^{13}$C NMR (101 MHz, DMSO-d$_6$) δ 158.4, 157.5, 153.8, 147.9, 146.7, 144.9, 143.0, 136.3, 132.6, 127.3, 122.7, 121.0, 120.8, 118.3, 118.3, 116.7, 116.3, 112.1, 111.4, 107.34, 107.2, 102.1, 64.3, 64.1, 56.0, 55.7, 41.7, 25.0; MS (ESI, +ve) m/z 483.2 [(M+H), 100%]; HRMS (ESI, +ve) Found: (M-FH)$^+$ 483.2035, $C_{28}H_{27}N_4O_4$ requires 483.2032; $v_{max}$ 3307, 2932, 1622, 1577, 1528, 1502, 1457, 1433, 1420, 1359, 1313, 1283, 1259, 1237, 1222, 1210, 1171, 1127, 1065, 1049, 1025, 894, 740 cm$^{-1}$.

Synthesis Example 28 BT2177

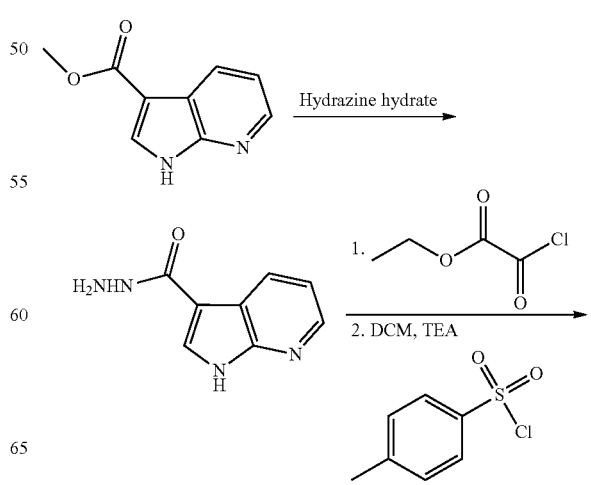

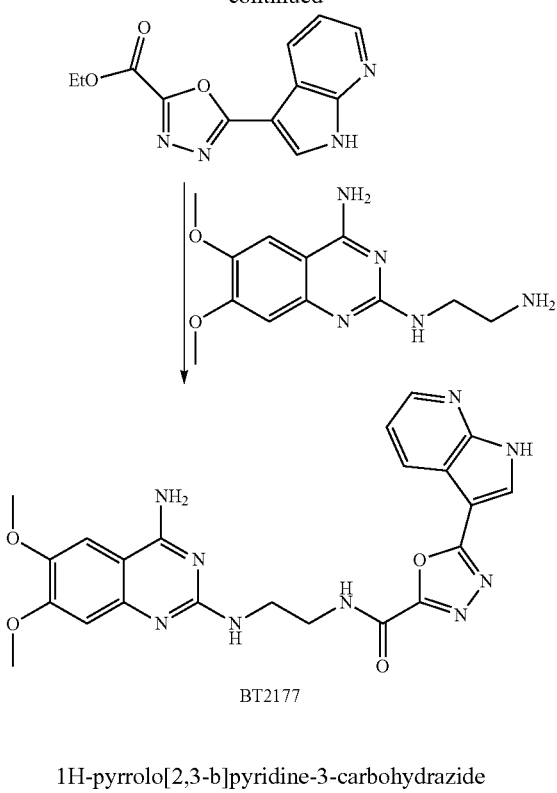

1H-pyrrolo[2,3-b]pyridine-3-carbohydrazide

A solution of methyl 1H-pyrrolo[2,3-b]pyridine-3-carboxylate (882 mg, 5.20 mmol) in dioxane (5 mL) was treated with hydrazine monohydrate (1.51 mL, 31 mmol) and refluxed for 18 h. The reaction mixture was cooled and the solid collected by vacuum filtration and the crystals washed with ether (10 mL) to afford 1H-pyrrolo[2,3-b]pyridine-3-carbohydrazide (553 mg, 60%), as fine white crystals, which was used without further purification. $^1$H NMR (400 MHz, DMSO-$d_6$) δ 12.03 (s, 1H), 9.27 (s, 1H), 8.43 (d, J=7.8 Hz, 1H), 8.26 (d, J=4.6 Hz, 1H), 8.08 (s, 1H), 7.16 (dd, J=7.9, 4.7 Hz, 1H), 4.34 (s, 2H).

Ethyl 5-(1H-pyrrolo[2,3-b]pyridin-3-yl)-1,3,4-oxadiazole-2-carboxylate

A solution of 1H-pyrrolo[2,3-b]pyridine-3-carbohydrazide (500.0 mg, 2.84 mmol) in DCM (20 mL) at 0° C. was treated with triethylamine (1.19 mL, 8.51 mmol) then dropwise ethyl chlorooxoacetate (0.33 mL, 2.98 mmol). The mixture was stirred at the same temperature for 30 min then warmed up to 18° C. for 30 min before being added p-toluenesulfonyl chloride (541.0 mg, 2.84 mmol). Ethyl 5-(1H-pyrrolo[2,3-b]pyridin-3-yl)-1,3,4-oxadiazole-2-carboxylate (120.0 mg, 16%) ($R_f$=0.31, 2:98 v/v methanol/diethyl ether) was obtained as white solid. $^1$H NMR (400 MHz, DMSO-$d_6$) δ 12.79 (s, 1H), 8.48 (s, 1H), 8.47-8.36 (m, 2H), 7.34 (dd, J=7.8, 4.8 Hz, 1H), 4.45 (q, J=7.1 Hz, 2H), 1.37 (t, J=7.1 Hz, 3H); $^{13}$C NMR (100 MHz, DMSO-$d_6$) δ 162.9, 154.8, 154.2, 148.7, 144.7, 130.2, 128.6, 117.9, 116.6, 97.5, 62.8, 13.9; (+)-LRESIMS m/z (rel. int.) 281.1 (100) [M+Na]; $v_{max}$ 3140, 2993, 2817, 1732, 1624, 1578, 1533, 1495, 1470, 1411, 1330, 1265, 1167, 1037, 1014, 839, 808, 780, 730 cm$^{-1}$.

BT2177

According to General Procedure E, a solution of N$^2$-(2-aminoethyl)-6,7-dimethoxy-N$^4$-phenethylquinazoline-2,4-diamine (80.0 mg, 0.30 mmol), ethyl 5-(1H-pyrrolo[2,3-b]pyridin-3-yl)-1,3,4-oxadiazole-2-carboxylate (46.1 mg, 0.18 mmol) in ethanol (1 mL) was irradiated at 80° C. for 3 h. BT2177 (60.0 mg, 71%) ($R_f$=0.47, 2.5:17.5:80 v/v/v methanol saturated ammonia/methanol/dichloromethane) was obtained as a cream solid. $^1$H NMR (400 MHz, DMSO-$d_6$) δ 12.40 (brs, NH), 9.98 (brs, NH), 8.50-8.32 (m, 3H), 7.41 (s, 1H), 7.34 (m, 1H), 7.05 (brs, NH$_2$), 6.96 (s, 1H), 6.42 (brs, NH), 3.90 (s, 3H), 3.78 (s, 3H), 3.51 (s, 4H); $^{13}$C NMR (100 MHz, DMSO-$d_6$)$^5$ 162.8, 161.6, 160.0, 157.4, 154.5, 153.7, 149.2, 149.0, 145.1 (CH+Cq), 130.2, 129.0, 118.2, 117.0, 105.9, 104.2, 103.8, 98.2, 56.3, 55.8, 41.9, 40.5; (+)-LRESIMS m/z (rel. int.) 476.3 (100) [M+H]$^+$; HRMS (ESI, +ve) Found: (M+H)$^+$476.1797, C$_{22}$H$_{22}$N$_9$O$_4$ requires 476.1795; $v_{max}$ 3556, 3398, 3279, 1686, 1651, 1630, 1563, 1502, 1446, 1313, 1271, 1231, 1211, 1184, 1143, 1103, 997, 852, 807, 791, 766 cm$^{-1}$.

Synthesis Example 29 BT2178

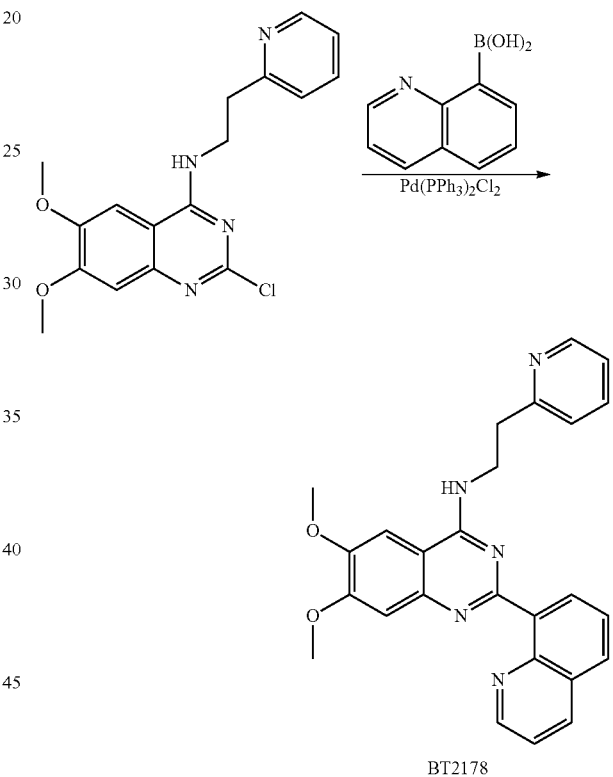

According to General Procedure C, a solution 2-chloro-6,7-dimethoxy-N-(2-(pyridin-2-yl)ethyl)quinazolin-4-amine (50.0 mg, 0.14 mmol), quinolin-8-ylboronic acid (37.6 mg, 0.21 mmol), K$_2$CO$_3$ (100.2 mg, 0.72 mmol) and Pd(PPh$_3$)$_2$Cl$_2$ (5.1 mg, 0.007 (3) mmol) in dimethoxyethane-water-ethanol (1.5 mL) was irradiated at 120° C. for 25 min. BT2178 (55.0 mg, 87%) ($R_f$=0.18, 5:95 v/v methanol saturated ammonia/dichloromethane) was obtained as a white solid. $^1$H NMR (400 MHz, DMSO-$d_6$) δ 8.83 (d, J=4.0 Hz, 1H), 8.46 (d, J=4.6 Hz, 1H), 8.41 (d, J=8.3 Hz, 1H), 8.08 (t, J=5.1 Hz, NH), 8.03 (d, J=8.2 Hz, 1H), 7.85 (d, J=7.0 Hz, 1H), 7.68 (t, J=7.7 Hz, 1H), 7.64 (s, 1H), 7.61 (t, J=7.7 Hz, 1H), 7.52 (dd, J=8.2, 4.0 Hz, 1H), 7.20-7.13 (m, 3H), 3.90 (s, 3H), 3.89 (s, 3H), 3.80 (q, J=6.5 Hz, 2H), 3.17 (m, overlapped with MeOH, 2H); $^{13}$C NMR (101 MHz, DMSO-$d_6$) δ 161.5, 159.5, 158.1, 153.7, 150.0, 149.2, 148.2, 146.5, 145.9, 140.9, 136.3, 136.0, 129.4, 128.1, 128.0, 125.9, 123.1, 121.4, 121.2, 107.2, 107.12, 101.9, 56.0, 55.6, 40.6, 36.9; MS (ESI, +ve) m/z 438.3 [(M+H), 100%]; HRMS (ESI, +ve) Found: (M+H)⁺438.1929, $C_{26}H_{24}N_5O_2$ requires 438.1930; $v_{max}$ 3266, 2935, 1619, 1586, 1522, 1499, 1474, 1423, 1355, 1253, 1219, 1175, 1145, 1042, 1000, 855, 836, 801, 788 cm⁻¹.

Synthesis Example 30 BT2179

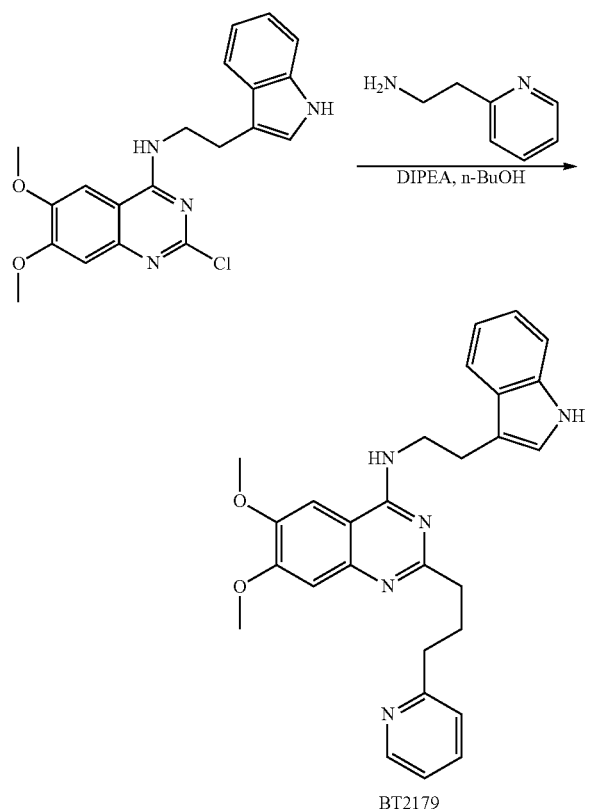

A 10 mL snap-cap microwave vessel was charged with a mixture of N-(2-(1H-indol-3-yl)ethyl)-2-chloro-6,7-dimethoxyquinazolin-4-amine (75.0 mg, 0.19 mmol), 2-pyridylethylamine (117 µL, 0.98 mmol), N,N-diisopropylethylamine (63 µL, 0.49 mmol) and n-butanol (2 mL). The tube was sealed then subjected to microwave irradiation (120° C./2 h, ramp time 5 minutes, maximum power 250 W). The mixture was cooled and concentrated in vacuo and the resulting residue was subjected to flash column chromatography [silica, 5:95 v/v methanol saturated ammonia/ethyl acetate elution] and concentration of the appropriate fractions ($R_f$=0.39, 5:95 v/v methanol saturated ammonia/ethyl acetate elution) to give the compound BT2179 (60.0 mg, 65%) as a white solid. ¹H NMR (400 MHz, methanol-d₄) δ 8.38 (d, J=4.7 Hz, 1H), 7.54 (m, 2H), 7.32 (d, J=8.1 Hz, 1H), 7.20 (s, 1H), 7.15 (m, 2H), 7.06 (t, overlapped, J=7.4 Hz, 1H), 7.04 (s, 1H), 6.92 (t, J=7.4 Hz, 1H), 6.76 (s, 1H), 3.85 (s, 3H), 3.84 (m, overlapped, 2H), 3.80 (s, 3H), 3.76 (m, overlapped, 2H), 3.12 (t, J=7.4 Hz, 2H), 3.07 (t, J=7.0 Hz, 2H); ¹³C NMR (101 MHz, methanol-d) δ 169.1, 168.9, 168.6, 163.7, 157.5, 157.0, 154.7, 146.4, 146.1, 136.9, 133.1, 131.3, 130.8, 130.2, 127.5, 127.4, 121.9, 120.2, 113.2, 112.9, 111.9, 64.6, 64.1, 51.1, 50.4, 47.2, 34.2; MS (ESI, +ve) m/z 469.2 [(M+H), 100%]; HRMS (ESI, +ve) Found: (M+H)⁺469.2352, $C_{27}H_{29}N_6O_2$ requires 469.2352; $v_{max}$ 3408, 2933, 1626, 1583, 1505, 1457, 1435, 1359, 1303, 1234, 1212, 1008, 853, 744 cm⁻¹.

Synthesis Example 31—BT2181

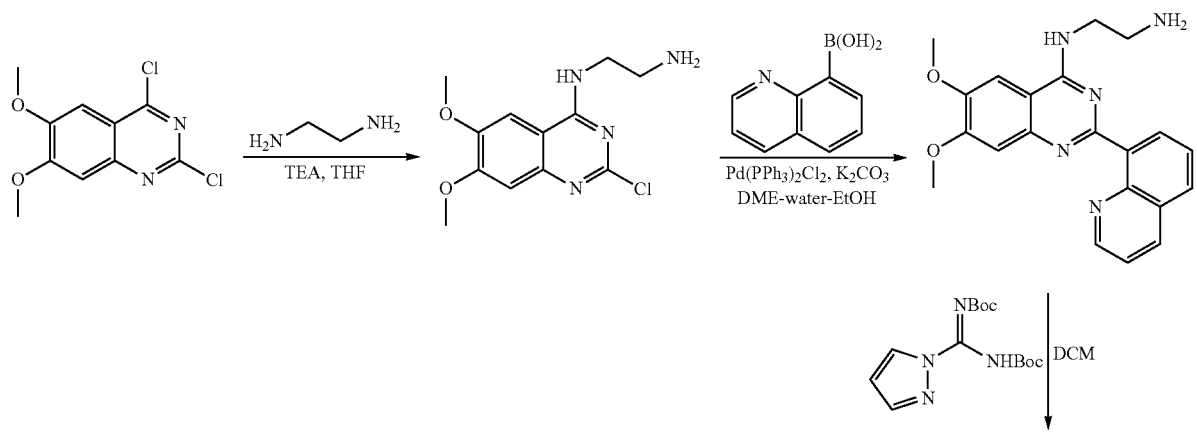

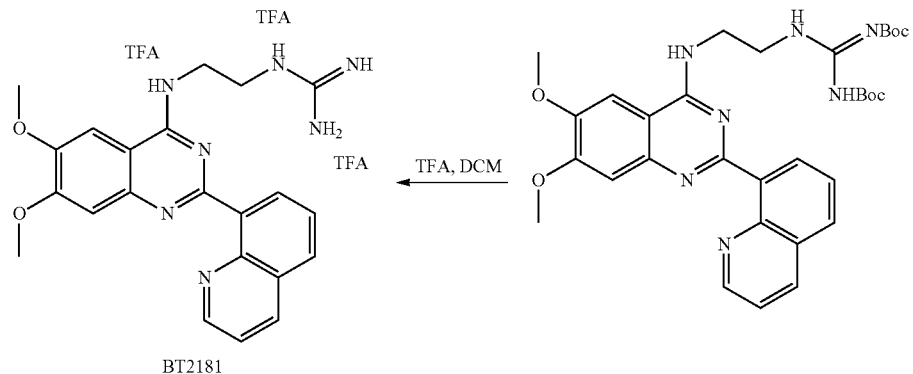

In accordance with General Procedure B, a solution of 2,4-dichloro-6,7-dimethoxyquinazoline (200.0 mg, 0.78 mmol), ethylenediamine (104 μL, 1.56 mmol), triethylamine (108 μL, 0.78 mmol) in tetrahydrofuran (10 mL) was stirred at 18° C. for 18 h. Flash chromatography ($R_f$=0.19, 12.5:87.5 v/v methanol saturated ammonia/dichloromethane) provided N$^1$-(2-chloro-6,7-dimethoxyquinazolin-4-yl)ethane-1,2-diamine (200.0 mg, 91%) as an ivory solid. $^1$H NMR (400 MHz, DMSO-d$_6$) δ 8.31 (s, NH), 7.63 (s, 1H), 7.05 (s, 1H), 3.88 (s, 6H), 3.49 (t, J=6.6 Hz, 2H), 2.97 (overlapped, brs, NH$_2$), 2.81 (t, J=6.6 Hz, 3H); $^{13}$C NMR (101 MHz, DMSO-d$_6$) b 160.2, 155.2, 154.3, 148.4, 147.1, 107.0, 106.5, 102.4, 56.1, 55.8, 44.3, 40.6; MS (ESI, +ve) m/z 283 [(M+H)$^+$, 100%].

According to General Procedure C, a solution of N$^1$-(2-chloro-6,7-dimethoxyquinazolin-4-yl)ethane-1,2-diamine (126.0 mg, 0.73 mmol), quinolin-8-ylboronic acid (189.0 mg, 1.09 mmol), K$_2$CO$_3$ (503.3 mg, 3.64 mmol) and Pd(PPh$_3$)$_2$Cl$_2$ (25.6 mg, 0.03 (6) mmol) in dimethoxyethane-water-ethanol (4 mL) was irradiated at 120° C. for 25 min. Flash chromatography ($R_f$=0.14, 15:15:95 v/v/v methanol saturated ammonia/methanol/ethylacetate) provided N$^1$-(6,7-dimethoxy-2-(quinolin-8-yl)quinazolin-4-yl)ethane-1,2-diamine (200.0 mg, 73%) as a yellow solid contaminated with quinolin-8-ylboronic acid. MS (ESI, +ve) m/z 376 [(M+H)$^+$, 100%].

A solution of the above N$^1$-(6,7-dimethoxy-2-(quinolin-8-yl)quinazolin-4-yl)ethane-1,2-amine (100.0 mg, 0.27 mmol) in dichloromethane (2 mL) was treated with tert-butyl (Z)-(((tert-butoxycarbonyl)amino)(1H-pyrazol-1-yl)methylene)carbamate (82.7 mg, 0.27 mmol) and the resulting reaction mixture was stirred at 18° C. for 18 h. Solvent was evaporated and the residue was subjected to flash column chromatography (silica, 5:95 v/v methanol saturated ammonia/diethyl ether elution) and concentration of the appropriate fractions ($R_f$=0.19, 5:95 v/v methanol saturated ammonia/diethylether elution) to give the di-Boc-protected guanidine derivate (128.0 mg, 77.8%) as an ivory solid. $^1$H NMR (400 MHz, Chloroform-d) δ 11.45 (s, 1H), 9.14 (d, J=4.1 Hz, 1H), 8.46 (t, J=5.3 Hz, 1H), 8.28 (d, J=8.3 Hz, 1H), 7.96 (d, J=7.6 Hz, 1H), 7.93 (d, J=7.6 Hz, 1H), 7.67 (t, J=7.6 Hz, 1H), 7.49 (dd, J=8.3, 4.1 Hz, 1H), 7.31-7.29 (m, 1H), 7.05 (s, 1H), 7.04 (s, 1H), 3.92 (s, 3H), 3.66 (s, 3H), 3.57 (m, 2H), 3.51 (m, 2H), 1.49 (s, 9H), 1.45 (s, 9H); $^{13}$C NMR (101 MHz, Chloroform-d) δ 163.6, 161.5, 159.0, 156.6, 153.9, 153.1, 150.2, 148.3, 146.7, 146.5, 140.8, 136.9, 130.5, 128.9, 128.3, 126.7, 121.1, 107.9, 107.2, 101.0, 83.1, 79.3, 56.1, 56.0, 40.3, 39.9, 28.4 (3C), 28.1 (3C); MS (ESI, +ve) m/z 618 [(M+H)+, 100%]; IR (ATR) v$_m$3285, 2980, 2254, 1720, 1621, 1582, 1528, 1501, 1415, 1367, 1344, 1252, 1218, 1134, 1045, 1021, 905, 724 cm$^{-1}$.

A solution of Boc-protected guanidine compound formed above, in dichloromethane (5 mL) was treated dropwise with trifluoroacetic acid (2.0 mL) at 0° C. The resulting mixture was stirred at 18° C. until the completion conversion (observed by TLC). Solvent was then evaporated to obtain the TFA salt of BT2181 (100.0 mg) as a yellow solid. $^1$H NMR (400 MHz, DMSO-d$_6$) δ 9.88 (t, J=5.8 Hz, NH), 9.31-9.19 (m, 1H), 9.07 (d, J=7.5 Hz, 1H), 8.75 (d, J=8.2 Hz, 1H), 8.41 (d, J=8.2 Hz, 1H), 8.13 (t, J=6.3 Hz, NH), 7.92-7.87 (m, 2H), 7.81 (s, 1H), 7.74 (s, 1H), 7.38 (brs, 3NH), 4.04 (s, 3H), 3.99-3.97 (m, 2H), 3.94 (s, 3H), 3.62-3.57 (m, 2H); $^{13}$C NMR (101 MHz, DMSO-d$_6$) δ 159.5, 157.6, 156.5, 155.1, 151.2, 150.5, 145.0, 139.8, 134.9, 134.7, 134.1, 128.9, 127.5, 124.3, 123.0, 106.6, 103.6, 101.9, 57.2, 56.8, 41.0, 40.3; MS (ESI, +ve) m/z 418 [(M+H)$^+$, 100%]; HRMS (ESI, +ve) Found: (M+H)+ 418.1993, C$_{22}$H$_{24}$N$_7$O$_2$ requires 418.1991; IR (ATR) v$_{max}$ 3333, 3095, 1710, 1673, 1621, 1598, 1549, 1510, 1471, 1443, 1424, 1401, 1274, 1198, 1176, 1119, 1105, 1053, 1042, 1027, 835, 796, 719 cm$^{-1}$.

Synthesis Example 32 BT2187

Synthesis Example 33 BT2184

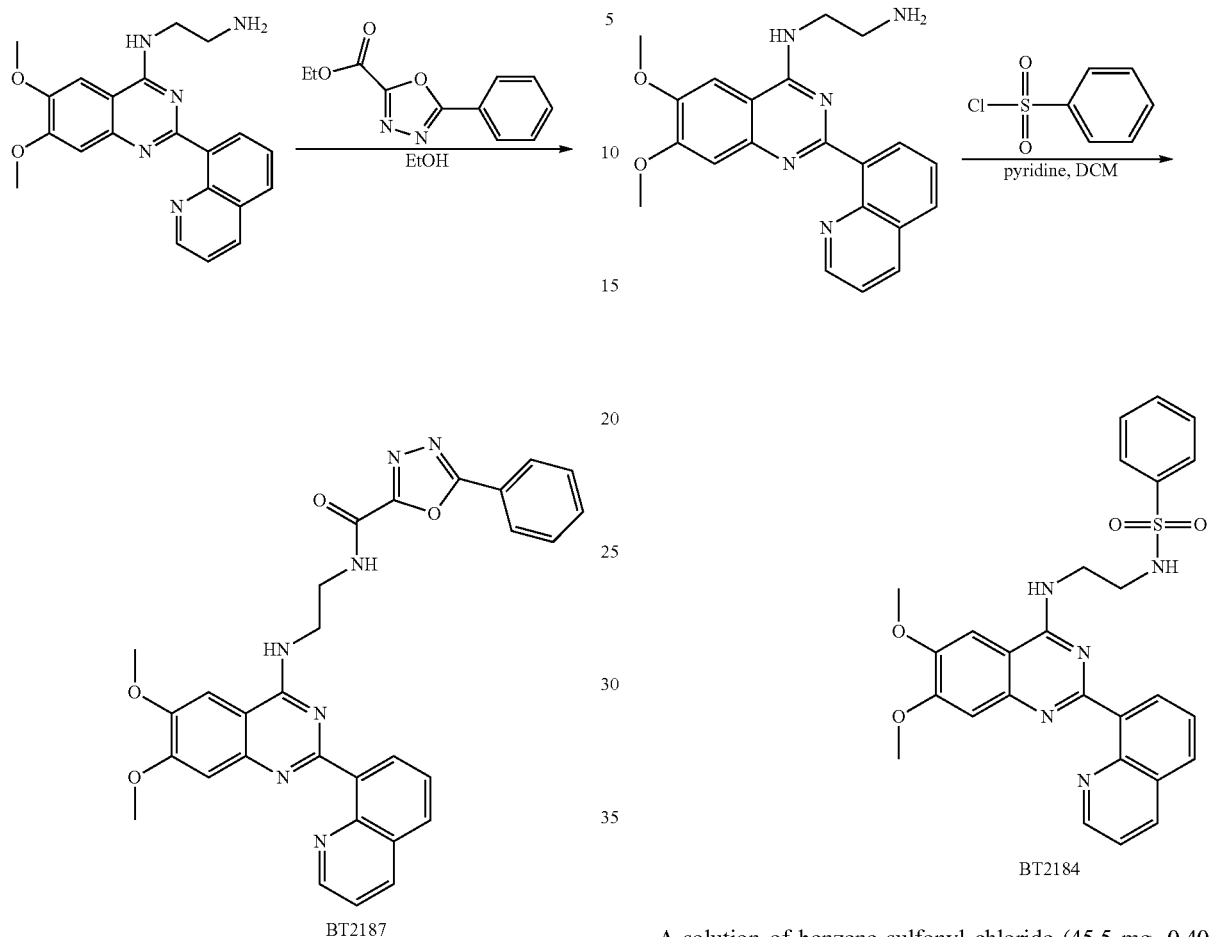

According to General Procedure E, a solution of $N^1$-(6,7-dimethoxy-2-(quinolin-8-yl)quinazolin-4-yl)ethane-1,2-diamine (103.2 mg, 0.27 mmol), ethyl 5-phenyl-1,3,4-oxadiazole-2-carboxylate (40.0 mg, 0.18 mmol) and ethanol (1 mL) was irradiated at 80° C. for 3 h. Flash chromatography ($R_f$=0.19, 10:90 v/v methanol saturated ammonia/diethyl ether) provided BT2187 (79.5 mg, 79%) as an ivory solid. $^1$H NMR (400 MHz, Chloroform-d) δ 9.03-9.02 (m, 1H), 8.64 (brs, 1H), 8.24 (d, J=8.3 Hz, 1H), 8.04 (d, J=7.0 Hz, 1H), 7.99-7.92 (m, 2H), 7.87 (d, J=8.3 Hz, 1H), 7.66-7.58 (m, 1H), 7.58-7.47 (m, 2H), 7.47-7.38 (m, 3H), 7.11 (s, 1H), 6.95 (s, 1H), 3.80 (s, 3H), 3.65 (m, 5H), 3.59 (s, 2H); $^{13}$C NMR (101 MHz, Chloroform-d) δ 166.0, 161.3, 159.3, 158.3, 154.4, 154.1, 149.9, 148.5, 146.5, 146.3, 140.0, 137.2, 132.5, 130.9, 129.2 (2C), 128.8, 128.6, 127.4 (2C), 126.8, 122.9, 121.2, 107.5, 107.0, 100.8, 56.1, 55.9, 40.8, 40.2. MS (ESI, +ve) m/z 548 [(M+H), 100%]; HRMS (ESI, +ve) Found: (M+H)$^+$548.2044, $C_{30}H_{26}N_7O_4$ requires 548.2046; IR (ATR) $v_{max}$ 3279, 3060, 3006, 2937, 2833, 2251, 1683, 1622, 1578, 1548, 1525, 1499, 1449, 1421, 1352, 1245, 1217, 1174, 1143, 911, 798, 727, 711 cm$^{-1}$.

A solution of benzene sulfonyl chloride (45.5 mg, 0.40 mmol) in dichloromethane (2 mL) and pyridine (1 mL) was treated with $N^1$-(6,7-dimethoxy-2-(quinolin-8-yl)quinazolin-4-yl)ethane-1,2-diamine (50.0 mg, 0.13 mmol) at 0° C. The resulting mixture was stirred at same temperature for 1 h then warmed up to 18° C. until the conversion was complete (observed by TLC). Solvent was then evaporated and the residue was subjected to flash column chromatography (silica, 5:95 v/v methanol saturated ammonia/ethyl acetate elution) and concentration of the appropriate fractions ($R_f$=0.30, 5:95 v/v methanol saturated ammonia/ethyl acetate elution) to give BT2184 (50.0 mg, 44%) as an off white solid. $^1$H NMR (400 MHz, Chloroform-d) δ 9.00 (d, J=3.8 Hz, 1H), 8.23 (d, J=8.2 Hz, 1H), 8.08 (d, J=7.0 Hz, 1H), 7.91 (d, J=8.2 Hz, 1H), 7.66 (t, J=7.6 Hz, 1H), 7.66 (overlapped, brs, NH), 7.50 (d, J=7.6 Hz, 2H), 7.42 (dd, J=8.1, 4.1 Hz, 1H), 7.15 (t, J=7.4 Hz, 1H), 7.07 (s, 1H), 7.04-7.01 (m, 2H), 6.72 (s, 1H), 6.63 (brs, NH), 3.89 (s, 3H), 3.67 (s, 3H), 3.52 (m, 2H), 3.22 (m, 2H); $^{13}$C NMR (101 MHz, Chloroform-d) δ 161.0, 158.8, 154.0, 150.6, 148.4, 146.7, 146.0, 140.6, 139.2, 136.9, 131.5, 131.2, 129.0, 128.8 (2C), 126.5, 126.3 (2C), 121.2, 107.2, 107.0, 100.4, 77.4, 56.1, 56.0, 44.6, 39.9; MS (ESI, +ve) m/z 516 [(M+H), 100%]; HRMS (ESI, +ve) Found: (M+H)+516.1695, $C_{27}H_{26}N_5O_4S$ requires 516.1706; IR (ATR) $v_{max}$ 3273, 3002, 2936, 2833, 1623, 1589, 1526, 1501, 1420, 1361, 1321, 1305, 1258, 1244, 1217, 1156, 1092, 999, 796, 754, 689 cm$^{-1}$.

Synthesis Example 34—BT2182

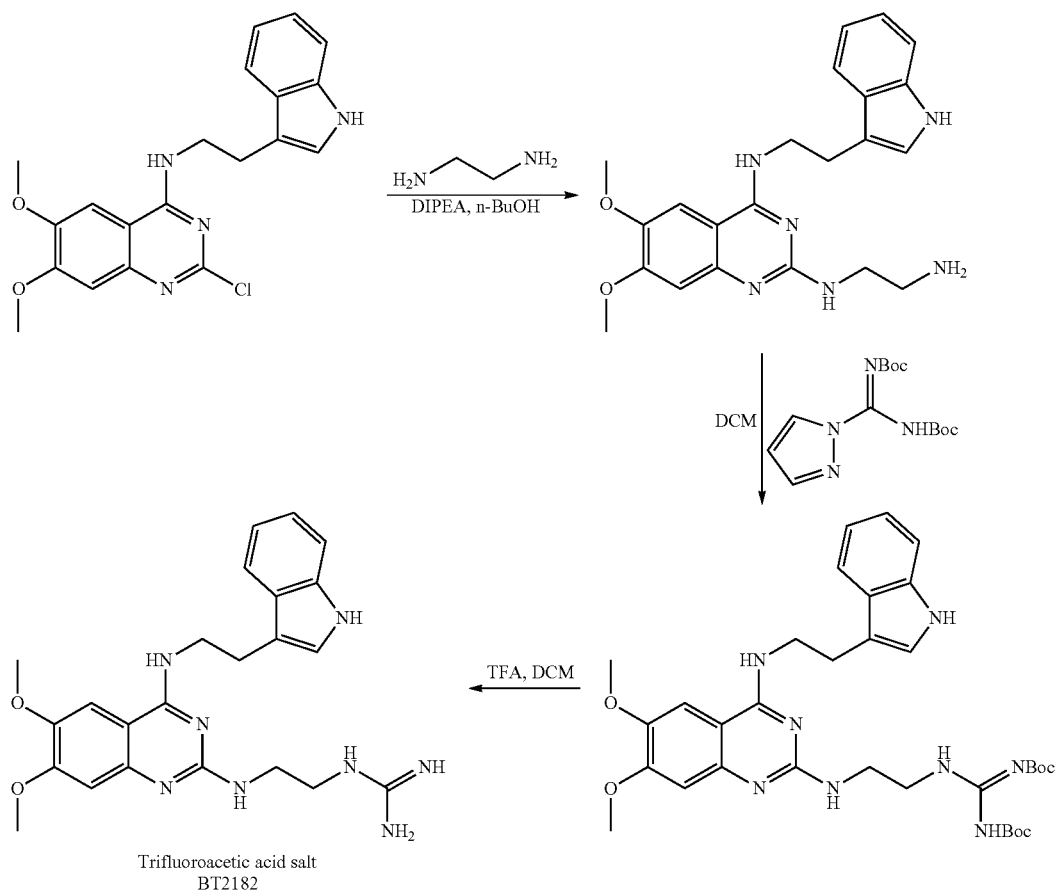

A 10 mL snap-cap microwave vessel was charged with a mixture of N-(2-(1H-indol-3-yl)ethyl)-2-chloro-6,7-dimethoxyquinazolin-4-amine (100.0 mg, 0.26 mmol), ethylenediamine (261 μL, 3.91 mmol), N,N-diisopropylethylamine (159 μL, 0.91 mmol) and n-butanol (2 mL). The tube was sealed then subjected to microwave irradiation (120° C./2 h, ramp time 5 minutes, maximum power 250 W). The mixture was cooled and concentrated in vacuo and the resulting residue was subjected to flash column chromatography (silica, 12.5:87.5 v/v methanol saturated ammonia/dichloromethane elution) and concentration of the appropriate fractions ($R_f$=0.24, 12.5:87.5 v/v methanol saturated ammonia/dichloromethane elution) afforded $N^4$-(2-(1H-indol-3-yl)ethyl)-$N^2$-(2-aminoethyl)-6,7-dimethoxyquinazoline-2,4-diamine (95.0 mg, 89%) as a yellow oil. $^1$H NMR (400 MHz, Methanol-$d_4$) δ 7.57 (d, J=7.9 Hz, 1H), 7.33 (d, J=8.1 Hz, 1H), 7.22 (s, 1H), 7.10-7.06 (m, 2H), 6.97 (t, J=7.5 Hz, 1H), 6.80 (s, 1H), 3.89 (s, 3H), 3.85 (overlapped t, J=7.3 Hz, 2H), 3.82 (s, 3H), 3.49 (t, J=6.2 Hz, 3H), 3.14 (t, J=7.3 Hz, 2H), 2.85 (t, J=6.2 Hz, 2H); $^{13}$C NMR (101 MHz, Methanol-$d_4$) δ 161.2, 161.0, 155.8, 149.0, 146.8, 138.2, 129.0, 123.4, 122.3, 119.5, 119.4, 113.9, 112.2, 105.3, 105.1, 104.0, 56.7, 56.2, 44.8, 43.1, 42.6, 26.3; MS (ESI, +ve) m/z 407.3 [(M+H)+, 100%].

A solution of the above $N^4$-(2-(1H-indol-3-yl)ethyl)-$N^2$-(2-aminoethyl)-6,7-dimethoxyquinazoline-2,4-diamine (84.0 mg, 0.21 mmol) in dichloromethane (2 mL) was treated with tert-butyl (Z)-(((tert-butoxycarbonyl)amino)(1H-pyrazol-1-yl)methylene)carbamate (70.5 mg, 0.23 mmol) and the resulting reaction mixture was stirred at 18° C. for 18 h. The solvent was evaporated and the residue was subjected to flash column chromatography (silica, 5:95 v/v methanol saturated ammonia/diethylether elution) and concentration of the appropriate fractions ($R_f$=0.19, 5:95 v/v methanol saturated ammonia/diethyl ether elution) to give the Boc-protected guanidine derivative (110.0 mg, 82.0%) as an ivory solid. $^1$H NMR (400 MHz, Chloroform-d) δ 11.50 (s, 1H), 8.85 (s, 1H), 8.57 (m, 1H), 7.60 (d, J=8.0 Hz, 1H), 7.34 (d, J=8.0 Hz, 1H), 7.15 (t, J=7.5 Hz, 1H), 7.06 (t, J=7.5 Hz, 1H), 7.02 (s, 1H), 6.82 (s, 1H), 6.59 (s, 1H), 5.95 (brs, 1H), 4.86 (brs, 1H), 3.94-3.83 (overlapped, m, 2H), 3.83 (s, 3H), 3.62 (m, 7H), 3.12 (t, J=6.3 Hz, 2H), 1.47 (s, 9H), 1.40 (s, 9H). $^{13}$C NMR (101 MHz, Chloroform-d) δ 163.5, 159.4, 159.3, 156.7, 154.2, 153.0, 148.7, 145.2, 136.4, 127.7, 122.3, 122.0, 119.4, 118.6, 113.3, 111.5, 105.6, 104.1, 101.2, 83.0, 79.4, 55.9 (3), 55.8 (7), 41.9, 41.4, 40.7, 28.3 (3C), 28.0 (3C), 24.9; MS (ESI, +ve) m/z 649.5 [(M+H)+, 100%]; IR (ATR) $v_{max}$ 3328, 2977, 1722, 1615, 1580, 1499, 1455, 1413, 1323, 1294, 1228, 1211, 1132, 1050, 1024, 732 cm$^{-1}$.

A solution of Boc-protected guanidine compound (70 mg, 0.11 mmol) obtained above in dichloromethane (5 mL) was treated dropwise with trifluoroacetic acid (1.0 mL) at 0° C. The resulting mixture was stirred at 20° C. until the completion conversion (observed by TLC). Solvent was then evaporated to obtain the TFA salt of BT2182 (70.0 mg) as an ivory solid. $^1$H NMR (400 MHz, DMSO-d$_8$) δ 12.87 (brs, 1H), 10.90 (s, 1H), 9.40 (brs, 1H), 8.36 (brs, 1H), 7.93 (brs, 1H), 7.70 (s, 1H), 7.56 (d, J=7.9 Hz, 1H), 7.36 (d, J=8.2 Hz, 1H), 7.20 (s, 1H), 7.07 (t, J=7.7 Hz, 1H), 7.00-6.95 (m, 2H), 3.89-3.84 (overlapped, m, 8H), 3.58 (brs, 2H), 3.40 (brs, 2H), 3.11 (brs, 2H); $^{13}$C NMR (101 MHz, DMSO-d$_8$) b 159.6, 157.6, 155.6, 153.2, 147.1, 136.7, 135.8, 127.6, 123.4, 121.4, 118.8, 118.6, 111.9, 111.9, 104.9, 102.6, 98.7, 65.4, 56.6, 56.5, 42.6, 24.8, 15.6; MS (ESI, +ve) m/z 449.3 [(M+H)+, 100%]; HRMS (ESI, +ve) Found: (M-FH)$^+$ 449.2413, C$_{23}$H$_{29}$N$_8$O$_2$ requires 449.2413; IR (ATR) v$_{max}$ 3310, 3145, 1673, 1611, 1580, 1515, 1432, 1395, 1278, 1199, 1176, 1127, 835, 743, 720 cm$^{-1}$.

Synthesis Example 35 BT2179

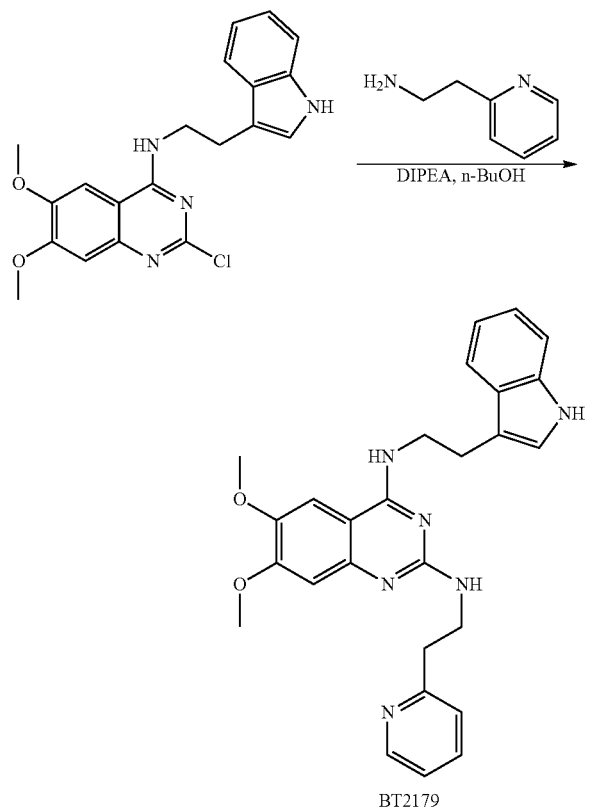

BT2179

In accordance with General Procedure D, a solution of N-(2-(1H-indol-3-yl)ethyl)-2-chloro-6,7-dimethoxyquinazolin-4-amine (75.0 mg, 0.19 mmol), 2-pyridylethylamine (117 μL, 0.98 mmol), N,N-diisopropylethylamine (63 μL, 0.49 mmol) and n-butanol (1.5 mL) was subjected to microwave irradiation (120° C./2 h, ramp time 5 minutes, maximum power 250 W). Flash chromatography (R$_f$=0.38, 5:95 v/v methanol saturated ammonia/ethyl acetate elution) provided BT2179 (60.0 mg, 65%) as an ivory solid. $^1$H NMR (400 MHz, Methanol-d$_4$) δ 8.38 (d, J=4.7 Hz, 1H), 7.56-7.51 (m, 2H), 7.32 (d, J=8.1 Hz, 1H), 7.20 (s, 1H), 7.19-7.13 (m, 2H), 7.09-7.00 (m, 2H), 6.92 (t, J=7.4 Hz, 1H), 6.76 (s, 1H), 3.86 (s, 3H), 3.86-3.83 (overlapped, m, 2H), 3.80 (s, 3H), 3.80-3.75 (m, 2H), 3.12 (app, t, J=7.4 Hz, 2H), 3.07 (app, t, J=7.0 Hz, 2H); $^{13}$C NMR (101 MHz, Methanol-d$_4$) δ 161.1, 161.0, 160.6, 155.8, 149.6, 149.0, 146.7, 138.5, 138.1, 129.0, 125.2, 123.3, 122.9, 122.3, 119.6, 119.4, 113.9, 112.2, 105.2, 105.0, 103.9, 56.7, 56.2, 43.1, 42.4, 39.2, 26.3; MS (ESI, +ve) m/z 469.2 [(M+H)$^+$, 100%]; HRMS (ESI, +ve) Found: (M-FH)$^+$469.2352, C$_{27}$H$_{29}$N$_6$O$_2$ requires 469.2352; IR (ATR) v, 3408, 2933, 2626, 1583, 1504, 1457, 1435, 1359, 1303, 1234, 1212, 743 cm$^{-1}$.

Synthesis Example 36 BT2186

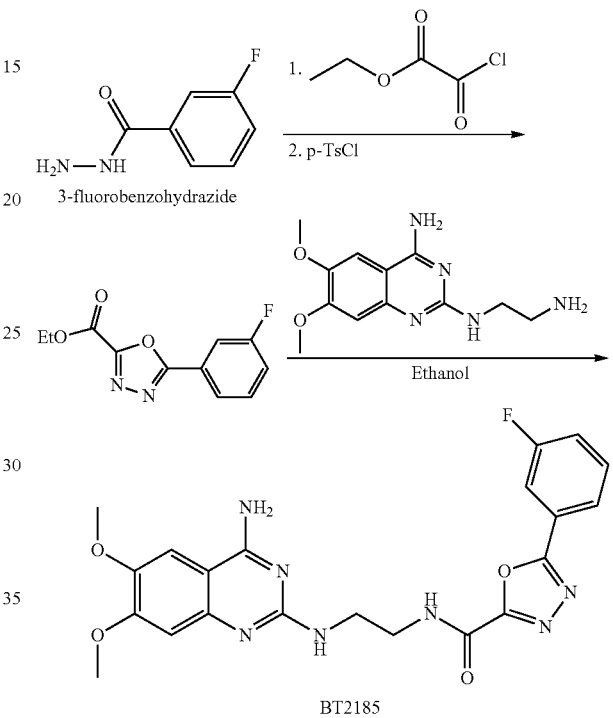

BT2185

A magnetically stirred solution of 3-fluorobenzohydrazide (502 mg, 3.26 mmol) in DCM (20 mL) maintained at 0° C. was treated with triethylamine (1.20 mL, 8.60 mmol) followed by dropwise addition of ethyl chlorooxoacetate (0.33 mL, 2.98 mmol). The mixture was stirred for 0.5 h then warmed and held at 18° C. for 0.5 h before p-toluenesulfonyl chloride (543 mg, 2.85 mmol) was added in one portion. The mixture was stirred for 18 h then a saturated aqueous solution of NaHCO$_3$ (10 mL) was added and the solution extracted with DCM (2×15 mL). The combined organic layers were then washed with brine (15 mL), dried (Na$_2$SO$_4$) and concentrated in vacuo to afford a residue which was purified by flash chromatography (1:20 v/v diethyl ether/DCM elution) to afford ethyl 5-(3-fluorophenyl)-1,3,4-oxadiazole-2-carboxylate (442 mg, 66%) as white crystals. $^1$H NMR (400 MHz, Chloroform-d) δ 7.99-7.95 (m, 1H), 7.89-7.85 (m, 1H), 7.57-7.51 (m, 1H), 7.34-7.28 (m, 1H), 4.56 (q, J=7.1 Hz, 2H), 1.49 (t, J=7.2 Hz, 3H); $^{13}$C NMR (101 MHz, Chloroform-d) δ 165.5 (d, JC-F=3.3 Hz), 164.2, 161.7, 155.6 (d, J=242.7 Hz), 131.3 (d, JC-F=8.1 Hz), 124.7 (d, JC-F=8.6 Hz), 123.5 (d, JC-F=3.2 Hz), 120.1 (d, JC-F=21.1 Hz), 114.7 (d, JC-F=24.5 Hz), 63.8, 14.2.

According to General Procedure E, a solution of N$^2$-(2-aminoethyl)-6,7-dimethoxyquinazoline-2,4-diamine (83.6 mg, 0.32 mmol), ethyl 5-(3-fluorophenyl)-1,3,4-oxadiazole-2-carboxylate (50.0 mg, 0.21 mmol) described directly above, and ethanol (1 mL) was irradiated at 80° C. for 3 h. Flash chromatography ($R_f$=0.32, 8:92 v/v methanol saturated ammonia/dichloromethane) provided BT2185 (85.0 mg, 88%) as an off white solid. $^1$H NMR (400 MHz, DMSO-$d_6$) δ 9.94 (brs, 1H), 7.87 (d, J=7.7 Hz, 1H), 7.79 (d, J=9.0 Hz, 1H), 7.66 (q, J=7.6 Hz, 1H), 7.52 (t, J=8.2 Hz, 1H), 7.41 (s, 1H), 7.08 (brs, 2H), 6.88 (s, 1H), 6.44 (brs, 1H), 3.86 (s, 3H), 3.78 (s, 3H), 3.52 (brs, 4H); $^{13}$C NMR (101 MHz, DMSO-$d_6$) δ 163.8 (JC-F=3.2 Hz), 162.2 (JC-F=245.6 Hz), 161.2, 159.4, 158.8, 154.1, 152.9, 148.2, 144.7, 131.8 (JC-F=8.3 Hz), 124.8 (JC-F=8.9 Hz), 123.3 (JC-F=3.0 Hz), 119.5 (JC-F=21.1 Hz), 113.8 (JC-F=21.4 Hz), 105.1, 103.8, 103.3, 55.8, 55.4, 41.3, 39.9; MS (ESI, +ve) m/z 454.1 [(M+H), 100%]; HRMS (ESI, +ve) Found: (M+H)+454.1639, $C_{21}H_{21}N_7O_4F$ requires 454.1639; IR (ATR) $v_{max}$ 3542, 3412, 3345, 3231, 3045, 1681, 1652, 1605, 1578, 1554, 1504, 1455, 1434, 1364, 1321, 1227, 1208, 1112, 998, 852, 830, 789, 727 cm$^{-1}$.

Synthesis Example 37—BT2229

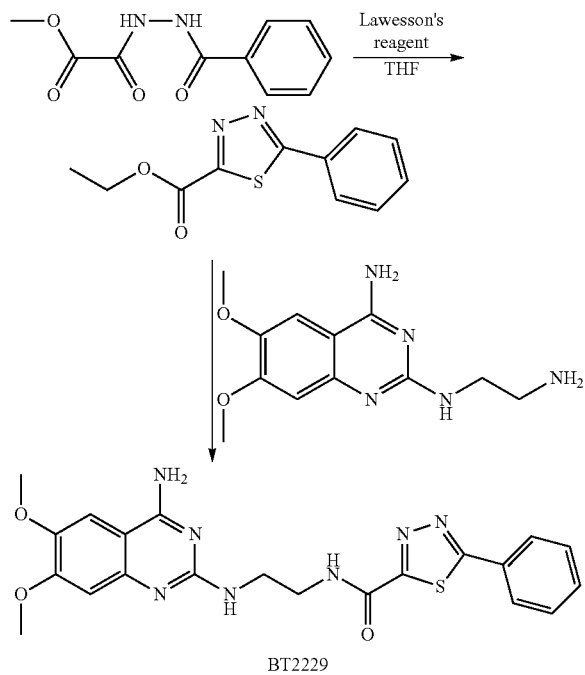

BT2229

Following a procedure reported by Banville, J et al in WO 2013/163279, a magnetically stirred mixture of ethyl 2-(2-benzoylhydrazineyl)-2-oxoacetate (790 mg, 3.35 mmol) in anhydrous THF (5 mL) was treated at rt with Lawesson's Reagent (1.35 g, 3.35 mmol) and then heated at reflux for 24 h. The solvent was removed in vacuo and the residue purified by flash column chromatography (silica, 1:20 v/v EtOAc/DCM elution) to afford ethyl 5-phenyl-1,3,4-thiadiazole-2-carboxylate (239 mg, 30%) as a white powder. $^1$H NMR (400 MHz, CDCl$_3$) δ 8.06-7.99 (m, 2H), 7.59-7.46 (m, 3H), 4.54 (q, J=7.1 Hz, 2H), 1.48 (t, J=7.1 Hz, 3H); $^{13}$C NMR (101 MHz, CDCl$_3$) δ 172.6, 159.6, 158.8, 132.1, 129.4 (3C), 128.3 (2C), 63.3, 14.2; MS (ESI, +ve) m/z 257 [(M+Na), 100%].

According to General Procedure E, a solution of $N^2$-(2-aminoethyl)-6,7-dimethoxyquinazoline-2,4-diamine (247 mg, 0.94 mmol), 5-phenyl-1,3,4-thiadiazole-2-carboxylate (110 mg, 0.47 mmol) and ethanol (4 mL) was irradiated at 80° C. for 3 h. Flash chromatography (1:20 v/v methanol saturated ammonia/dichloromethane) provided BT2229 (177 mg, 83%) as a yellow solid. $^1$H NMR (400 MHz, DMSO-$d_6$) δ 10.04 (br s, 1H), 8.08-7.99 (m, 2H), 7.65-7.55 (m, 3H), 7.42 (s, 1H), 7.07 (br s, 2H), 6.99 (br s, 1H), 6.45 (s, 1H), 3.94 (s, 3H), 3.78 (s, 3H), 3.56-3.47 (m, 4H); $^{13}$C NMR (101 MHz, DMSO-$d_6$) one peak obscured or overlapping δ 171.3, 165.5, 161.2, 159.5, 157.4, 154.0, 148.4, 144.7, 132.0, 129.6 (2C), 129.1, 127.9 (2C), 103.8, 103.3, 64.9, 55.8, 55.4, 41.9, 40.1; MS (ESI, +ve) m/z 452 [(M+H), 100%]; Single Crystal X-Ray Data collection: CrysAlis PRO 1.171.38.46 (Rigaku OD, 2015); cell refinement: CrysAlis PRO 1.171.38.46 (Rigaku OD, 2015); data reduction: CrysAlis PRO 1.171.38.46 (Rigaku OD, 2015); program(s) used to solve structure: SHELXT (Sheldrick, Acta Cryst. A71, 3-8. 2015); program(s) used to refine structure: SHELXL (Sheldrick, Acta Cryst. A71, 3-8.2015); molecular graphics: Olex2 (Dolomanov et al., J. Appl. Cryst. 42, 339-341. 2009); software used to prepare material for publication: Olex2 (Dolomanov et al., J. Appl. Cryst. 42, 339-341. 2009). Crystal data: $C_{21}H_{21}N_7O_3S$ Mr=451.51 Monoclinic, P21/n a=9.3352 (10) Å b=17.4633 (9) Å c=13.1223 (11) Å β=97.834 (9°) V=2119.3 (3) Å$^3$ Z=4 F(000)=944 Dx=0.415 Mg m$^{-3}$ Cu Kα radiation, λ=1.54184 Å Cell parameters from 2892 reflections θ=5.1-71.8° μ=1.70 mm$^{-1}$. T=150 K Plate, colourless 0.18×0.09×0.02 mm.

II. Biological Examples

Figure 2:
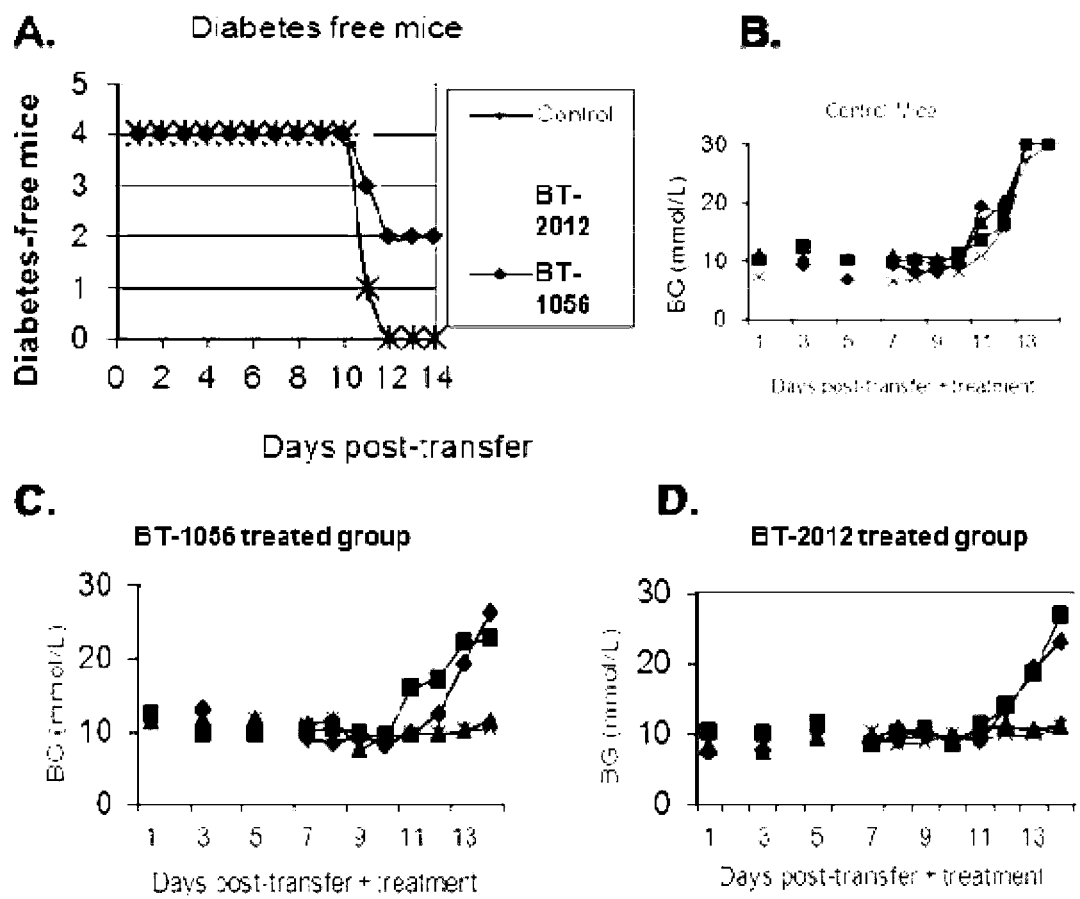
FIG. 2. Treatment of RIP-OVA$^{hi}$ mice from the time of adoptive transfer of OVA-specific OT-I and activated OT-II tg T cells with a small molecule heparanase inhibitor ("BT- 2012") (10 mg/kg QD, IP in saline/50% DMSO). (A) Incidence of diabetes (blood glucose >12 mmol) was significantly reduced (50%) following treatment with the small molecule heparanase inhibitor. Daily blood glucose levels of individual control (saline/50% DMSO treated) mice (B) were significantly higher in all controls compared to the treatment groups (C & D) where blood glucose remained normal in 50% of the individual treated mice or did not reach the same high levels as untreated in the 14 day assay period when treated with small molecule heparanase inhibitor compounds ("BT-2012" or "BT-1056" (as a comparator)).
Figure 3:
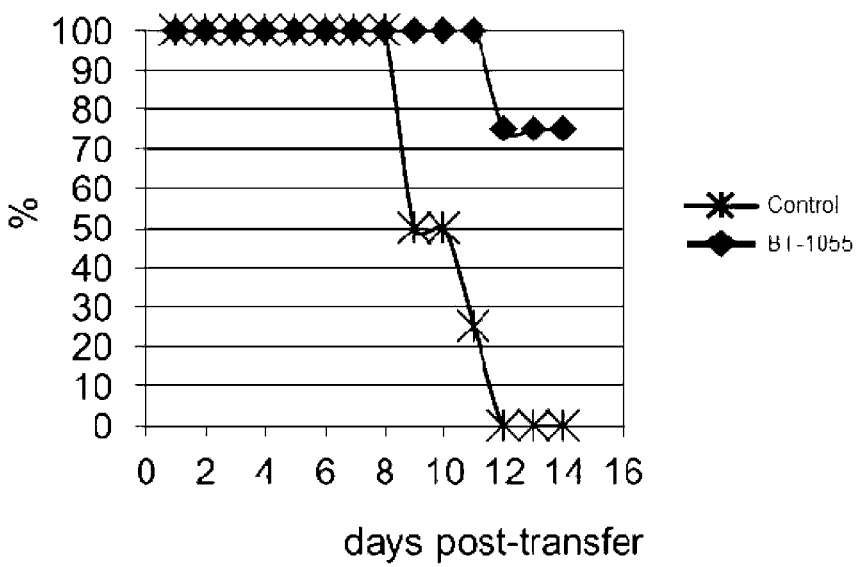
FIG. 3. Treatment of RIP-OVA$^{hi}$ mice from the time of adoptive transfer of OVA-specific OT-I and activated OT-II tg T cells with a control heparanase inhibitor ("BT-1055") (10 mg/kg QD, IP in saline/20% DMSO). (A) Incidence of diabetes (blood glucose >12 mmol) was significantly reduced (75%) following treatment with a heparanase inhibitor compound ("BT-1055"). Daily blood glucose levels of individual control (saline/20% DMSO treated) mice (B) were significantly higher in all controls compared to mice treated with comparator heparanase inhibitor (C) where blood glucose remained normal in 75% of the individual treated mice or did not reach the same high levels as untreated in the 14 day assay period.
Figure 3:
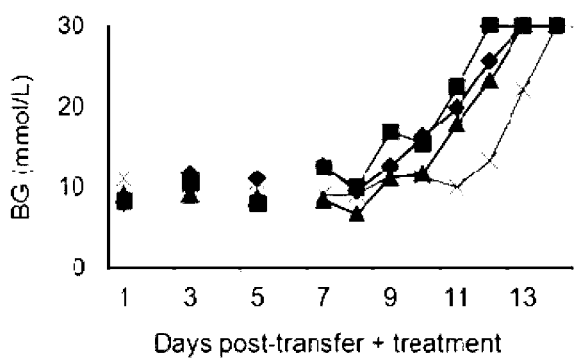
Figure 3:
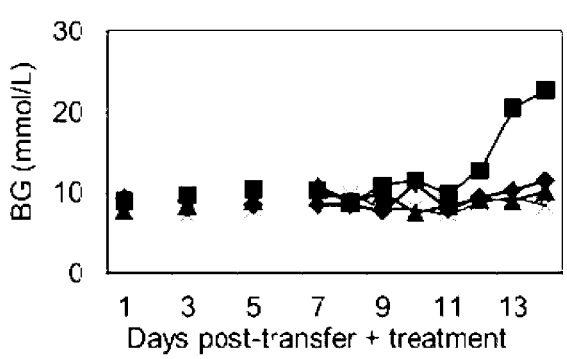
Figure 4:
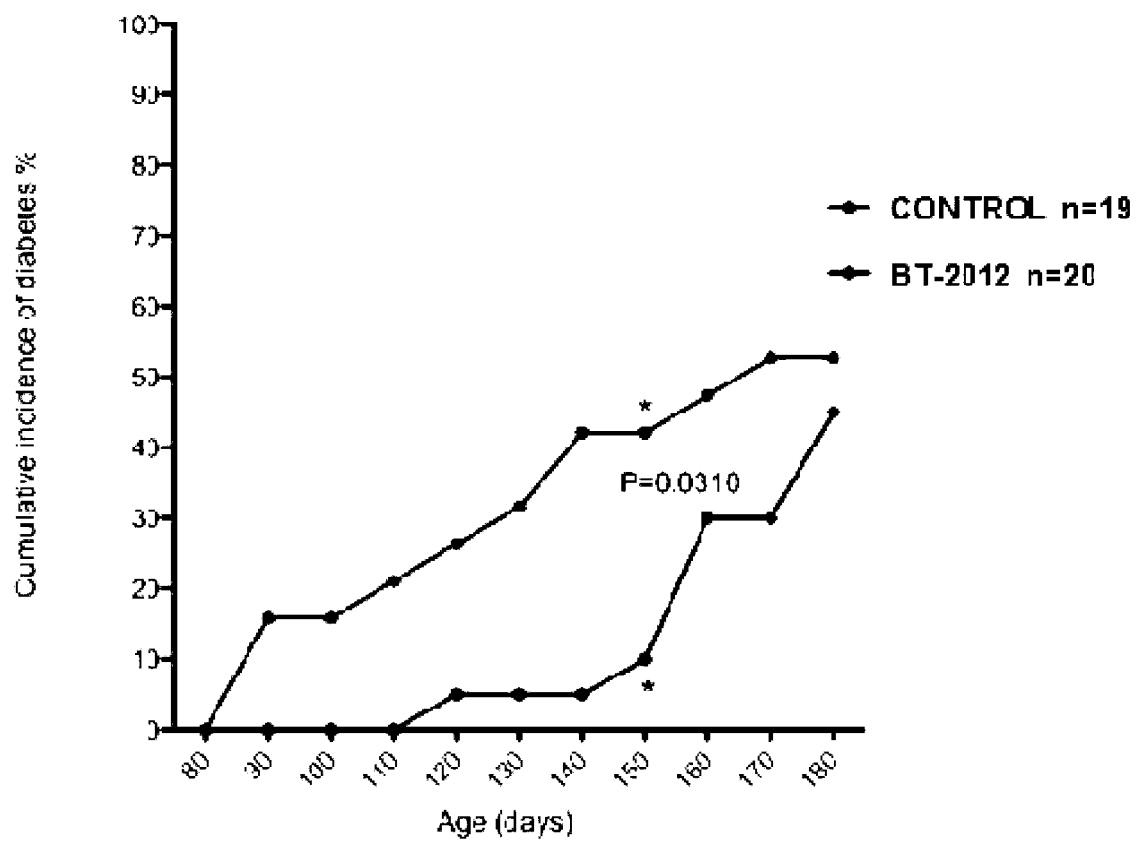
FIG. 4. Treatment of NOD/Lt mice with a small molecule heparanase inhibitor ("BT-2012"). All mice were dosed daily at 10 mg/kg, IP in saline/50% DMSO from 80-180 days of age. Onset of clinical diabetes was determined by measuring urine glucose twice weekly with Multistix reagent strips and confirmed by measuring non-fasting blood glucose levels in tail vein blood using a MediSense glucometer with hyperglycemia defined as 2 consecutive blood glucose readings of 16 mmol/l or greater.

Comparative Example I—Establishment of the Adoptive Transfer of Type I Diabetes in Transgenic RIP-OVAhi Mice: An Acute Experimental Type I Diabetes Model for Rapid Drug Efficacy Profiling In NOD mice, the autoimmune disease process develops slowly because of the asynchronous destruction of the beta cells in different islets. Indeed Type I diabetes develops only after >90% of the total islet beta cell mass has been destroyed. The slow course of the disease in NOD mice offers realistic potential for immune intervention but, unfortunately, high throughput screening of test drugs is not feasible. A more acute model of diabetes can be induced experimentally using RIP-OVAhi transgenic mice which express a foreign ovalbumin (OVA) peptide, under the control of the rat insulin promoter (RIP), only in islet beta cells. Following adoptive transfer of nave OVA specific CD8+(OT-I) and activated OVA-specific CD4+(OT-II) transgenic T cells, the transgenic T cells traffic to the host lymph nodes where the OT-I T cells become activated and then to the OVA-expressing pancreatic islets where they rapidly induce islet beta cell destruction and diabetes, all mice succumbing to rapid onset of high blood glucose levels (hyperglycaemia) in the second week after cell transfer. Using heparanase knockout donor and recipient mouse strains, it has been demonstrated that this acute model of Type I diabetes is heparanase-dependent (FIG. 1). Compared to the development of Type I diabetes within 14 days in heparanase normal mice, lack of heparanase completely prevented Type I diabetes and the mice remained normoglycemic for the duration of the experiment (FIG. 1). These findings together with the acute clinical manifestation of this highly aggressive 'pseudoautoimmune' disease allows rapid initial screening of compounds to identify compounds that inhibit the development of Type I diabetes. Using the RIP-OVAhi acute model of Type I diabetes, the inventors have demonstrated that heparanase inhibitor compounds administered at 10 mg/kg ("BT-2012", disclosed in U.S. 62/433,639, and comparator heparanase inhibitor compounds denoted "BT-1056" and "BT-1055") protected RIP-OVAhi mice from Type I diabetes induction following adoptive transfer of diabetogenic tg T cells, with significant numbers of mice remaining Type I diabetes disease-free by 14 days after transfer (FIGS. 2 and 3).

Comparative Example II—Control of Blood Glucose Levels

Using the RIP-OVAhi transgenic mice the effect of a heparanase inhibitor compound (denoted "BT-1055") was tested for its effect on blood glucose levels. Following adoptive transfer of nave OVA specific CD8+(OT-I) and activated OVA-specific CD4+(OT-II) transgenic T cells into a number of RIP-OVAhi mice blood glucose was monitored regularly over two weeks in populations of mice treated with a comparative compound and a control group administered saline (FIG. 3).

Figure 5:
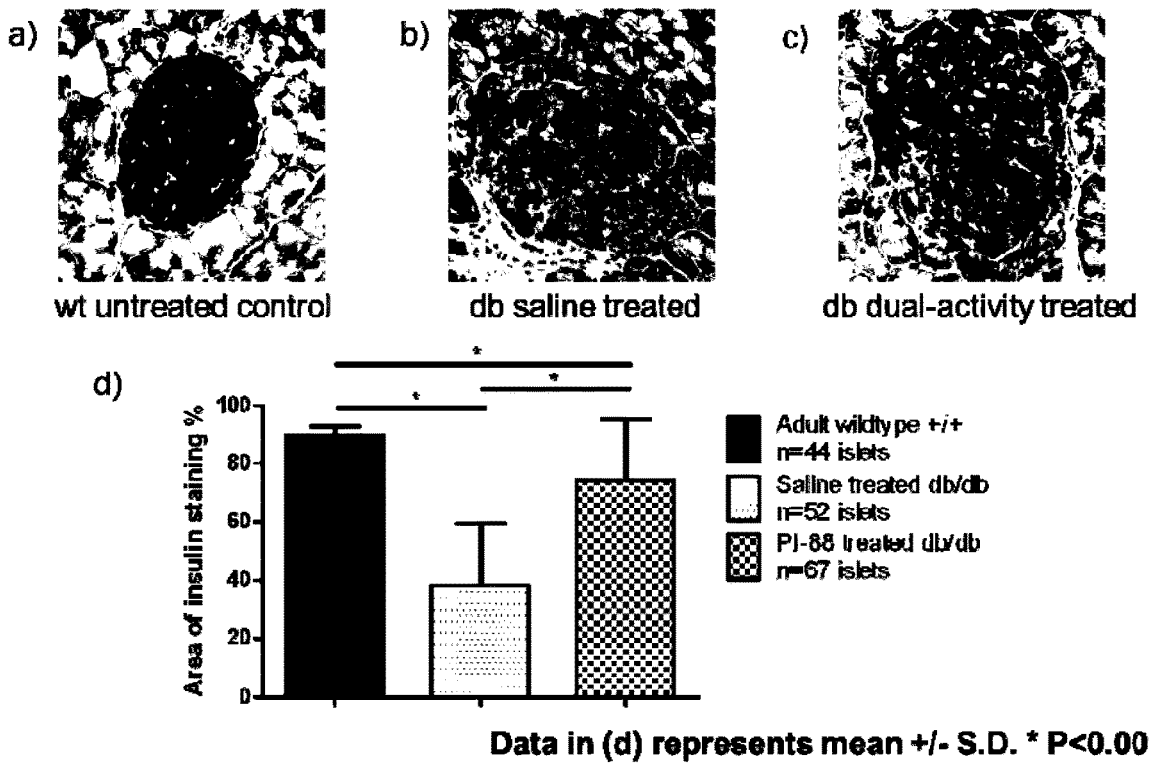
FIG. 5. Insulin content in pancreas sections in db/db mice a model of Type 2 diabetes. Mice were treated daily with 50 mg/kg PI-88 IP from 4 weeks of age. Onset of clinical diabetes was determined by measuring urine glucose twice weekly with Multistix reagent strips and confirmed by measuring non-fasting blood glucose levels in tail vein blood using a MediSense glucometer with hyperglycemia defined as 2 consecutive blood glucose readings of 16 mmol/l or greater. Insulin was detected by anti-insulin antibody staining.

Comparative Example III Effect of Treatment with a Sulfated Oligosaccharide (PI-88) on Insulin Production The db/db mouse has defective leptin signalling resulting from a point mutation in the leptin receptor gene. Plasma insulin levels become elevated very early in life (10-14 days of age), and the affected animals are obese by the time they are 3-4 weeks old. The animals are insulin resistant, hypertriglyceridemic, and have impaired glucose tolerance.

db/db mice were treated with saline or 50 mg/kg of PI-88 by daily intraperitoneal injection. At the cessation of treatment pancreatic islets were isolated and stained for insulin and the level of insulin expression assessed by quantitative morphometric analyses. FIG. 5 shows that compared to islets from untreated wild-type mice a significant reduction in insulin expression occurs in db/db mice treated with saline. However treatment of the db/db mice with PI-88 results in expression of insulin in islets that is increased compared to the saline treated db/db mice and is near to the level of insulin expression in the wild-type mice.

Figure 6:
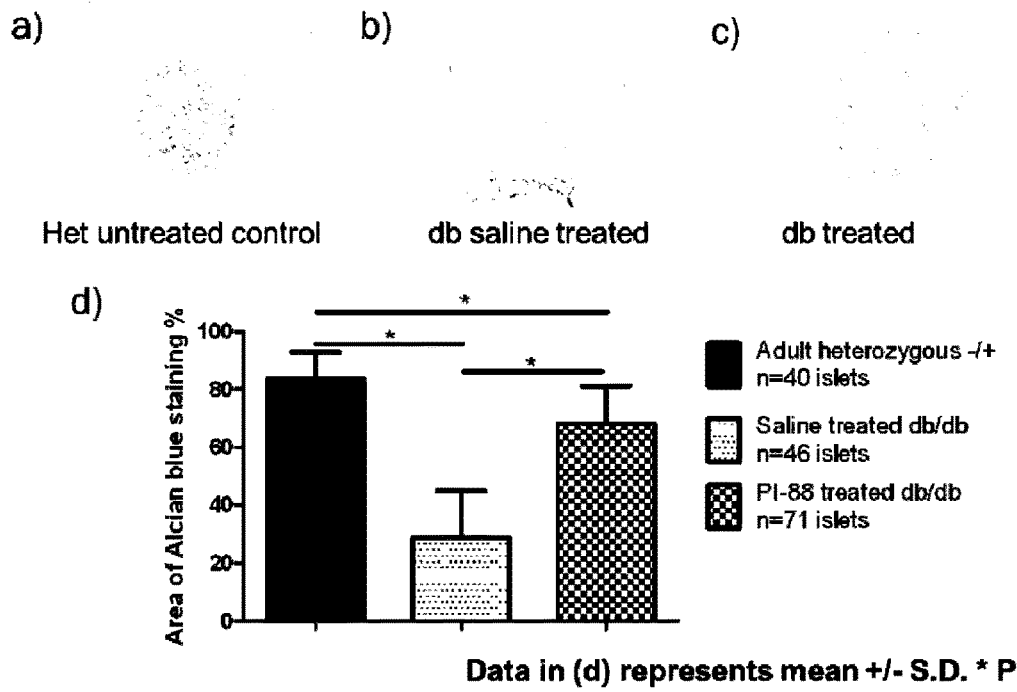
FIG. 6. Intra-islet HS content in pancreas sections in treated db/db mice. Mice were treated daily with 50 mg/kg PI-88 IP from 4 weeks of age. Onset of clinical diabetes was determined by measuring urine glucose twice weekly with Multistix reagent strips and confirmed by measuring non-fasting blood glucose levels in tail vein blood using a MediSense glucometer with hyperglycemia defined as 2 consecutive blood glucose readings of 16 mmol/l or greater. Islet HS was detected by Alcian blue staining.

Comparative Example IV Effect of Treatment with a Sulfated Oligosaccharide (PI-88) on Heparan Sulfate Levels db/db mice were treated with saline or 50 mg/kg of PI-88 daily by intraperitoneal injection. At the cessation of treatment pancreatic islets were isolated and stained with alcian blue to visualise heparan sulfate and the heparan sulfate content of the islets was assessed by quantitative morphometric analyses. FIG. 6 shows that compared to islets from untreated wild-type mice a significant reduction in heparan sulfate content occurs in the islets of db/db mice treated with saline. However treatment of the db/db mice with the sulfated polysaccharide results in islet heparan sulfate levels that are increased compared to the saline treated db/db mice and are near to the levels of heparan sulfate in the islets of wild-type mice.

Example V—General Screening Protocol for Test Compounds

1. Heparanase Inhibition:

Heparanase inhibitor compounds of the invention may be tested for inhibition of heparanase at 10 µM using a standardised enzymatic assay (Hammond E, et al. Development of a colorimetric assay for heparanase activity suitable for kinetic analysis and inhibitor screening. *Anal Biochem.* 2010; 396:112-116). Molecules exhibiting 50% or greater heparanase inhibition may be further assessed to determine the specific half-maximal inhibitor concentrations of heparanase ($IC_{50}$). Molecules with heparanase inhibition $IC_{50}$ within a desired range (e.g., 100 µM and below, 50 µM and below, 10 µM and below, 5 µM and below, 2 µM and below, etc) may be prioritised for further in vitro and in vivo screening as appropriate.

2. Establish Off-Target Activity Counter-Screens:

A first category of counter-screens may be used to determine whether heparanase inhibition by compounds of formula (I) occurs via competitive inhibition and not protein aggregation. A second category of counter-screens forms part of a larger suite of biochemical characterization to identify areas that might be improved as part of lead optimisation. For example, the second category of counter-screens may be used to assess off-target activity against the following:

heparanase-related glycosidases including ($\alpha$,$\beta$)-glucosidase and $\beta$-glucuronidase;

heparan sulfate binding proteins including VEGF, FGF-1 and FGF-2; and kinase inhibition panels to establish the ratio of on-target to off-target activity.

3. In Vitro Toxicity:

Heparanase inhibitors of formula (I) may be tested for dose dependent in vitro toxicity using the Jurkat cell line and the MTT assay which provides a measure of mitochondrial function as a surrogate for cell viability. Data will be represented as $Tox_{50}$ as drug concentration at which only 50% of cells remain viable. Typically, compounds that have a $Tox_{50}$ of 200 µM or greater may be prioritised for further evaluation.

4. In Vitro ADME (Absorption, Distribution, Metabolism, and Excretion):

Compounds of formula (I) may undergo an initial assessment of ADMET (absorption, distribution, metabolism, excretion and toxicology) properties using standard methods.

Initial in vitro assays may include the following:

A. Solubility: Compounds will be tested for solubility in a standard kinetic solubility assay at different pH levels (pH 2.1, 4.0 and 7.4) with a target solubility of 100 µg/ml.

B. PAMPA assays (membrane permeability/adsorption): The PAMPA assay is a well validated surrogate measure of membrane permeability which uses an artificial lipid bilayer, and is used increasingly in place of the Caco2 cell. Compounds will be compared with known standards drug compounds including Verapamil (high permeability) and Theophylline (low). High permeability will be required to prioritise molecules.

C. Liver microsome assay: The liver microsome assay is a well-established method for determining the oxidative metabolic stability of drug candidates. We propose to use both mouse and human microsomes to support decision making when selecting candidate for in vivo studies in mouse models. The percentage of compound remaining at multiple time points (0, 5, 15, 30, 45 min) will be determined in comparison with standard drug compounds including Propranolol (highly stable), Ketoprofen (intermediate stability) and Verapamil (rapid clearance).

D. Protein binding: The plasma clearance of drug candidates is determined by a combination of metabolic and renal clearance. The renal clearance of drug candidates which have high protein binding is lowered, since renal clearance is size dependent and proteins exceed the upper cut-off. Excessive protein binding can however limit the availability of the drug towards the biological target. Acceptable values may typically be in the range 90-98%. Measurement of free drug concentration in plasma using equilibrium dialysis in comparison to drug standards including Propranolol (low binding), Paroxetine (intermediate) and Losartan (high). Compounds with intermediate protein binding will be prioritised.

Example VI—Heparanase Inhibition

Heparanase inhibition assays were conducted as described previously (Hammond et al. *Anal Biochem,* 396 (1): 112-116 (2010)). Recombinant human active heparanase derived from Chinese hamster ovary cells was from R&D Systems. Bovine serum albumin-coated 96 well microplates (96F Maxisorp NNC #456537, Thermo Scientific) were used for the assays and were prepared by incubation of the plates with 1% (w/v) BSA dissolved in phosphate-buffered saline containing 0.05% (v/v) Tween-20 (PBST) at 37° C. for 1 h. The plates were washed three times with PBST, shaken dry, and stored for up to two weeks at 4° C. before use. Assay mixtures typically contained 42.5 mM sodium acetate buffer (pH 5.0), 0.8 nM heparanase, 100 µM fondaparinux (Arixtra™, Aspen Pharmacare), 5% (v/v) DMSO, and varying concentrations of inhibitor in a total volume of 100 µL. Following initiation of the reaction by addition of fondaparinux, the plate was sealed with adhesive film and incubated at 37° C. for 20-24 h. 100 µL of 1.69 mM WST-1 (Dojindo) solution in 0.1 M NaOH was added to the assay mixture. The plate was resealed and developed by incubation at 60° C. for 1 h, and the absorbance was measured at 584 nm. For the enzymatic assays, test compounds were dissolved and added to the assay at varying concentrations to calculate the level of inhibition.

Heparanase inhibition activity of various compounds of the invention was determined using standard methods. The results, expressed as the half maximal inhibitory concentration ($IC_{50}$), being the concentration of the compound of the invention required to achieve 50% inhibition of heparanase, are shown in Table 1:

TABLE 1

| Compound Code | Structure | $IC_{50}$ |
|---|---|---|
| BT2005 | *[structure]* | 41 µM |
| BT2007 | *[structure]* | 92.7 µM |

TABLE 1-continued
| Compound Code | Structure | IC$_{50}$ |
|---|---|---|
| BT2013 (doxazosin mesylate) | 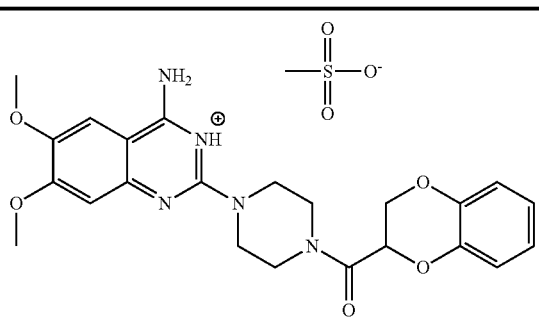 | 57.5 μM |
| BT2057 | 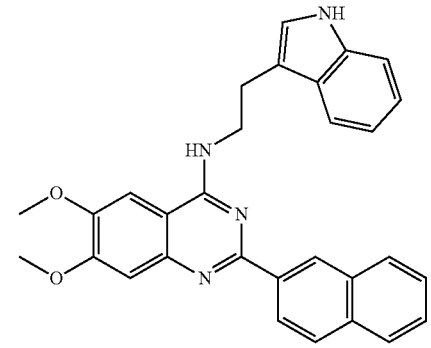 [SMILES: COc1cc2nc(-c3ccc4ccccc4c3)nc(NCCc3c[nH]c4ccccc34)c2cc1OC] | 56 μM |
| BT2062 | 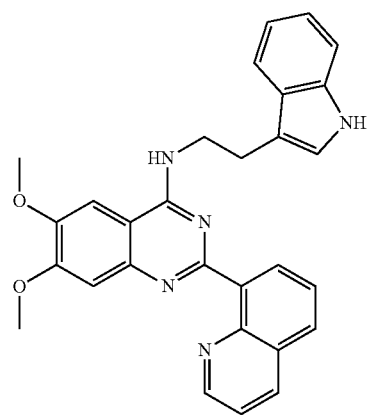 [SMILES: COc1cc2nc(-c3cccc4cccnc34)nc(NCCc3c[nH]c4ccccc34)c2cc1OC] | 1 μM |
| BT2090 | 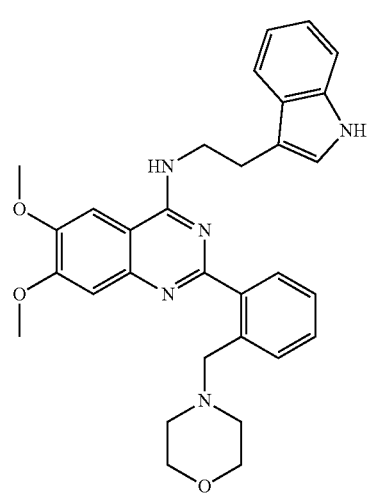 [SMILES: COc1cc2nc(-c3ccccc3CN3CCOCC3)nc(NCCc3c[nH]c4ccccc34)c2cc1OC] | 53.6 μM |
Heparanase inhibition (IC$_{50}$)

TABLE 1-continued
Heparanase inhibition (IC$_{50}$)
| Compound Code | Structure | IC$_{50}$ |
|---|---|---|
| BT2120 | 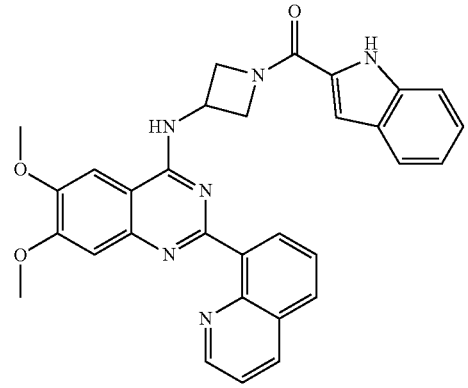 [SMILES: COc1cc2nc(-c3cccc4cccnc34)nc(NC3CN(C(=O)c4cc5ccccc5[nH]4)C3)c2cc1OC] | 0.7 μM |
| BT2148 | 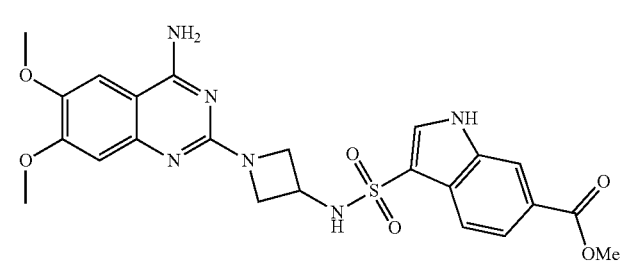 [SMILES: COC(=O)c1ccc2c(S(=O)(=O)NC3CN(c4nc(N)c5cc(OC)c(OC)cc5n4)C3)c[nH]c2c1] | 20.5 μM |
| BT2161 | 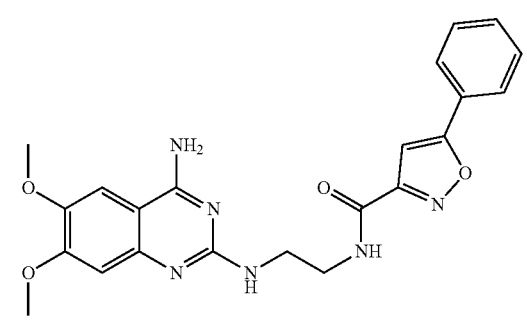 [SMILES: COc1cc2nc(NCCNC(=O)c3cc(-c4ccccc4)on3)nc(N)c2cc1OC] | 18.9 μM |
| BT2162 | 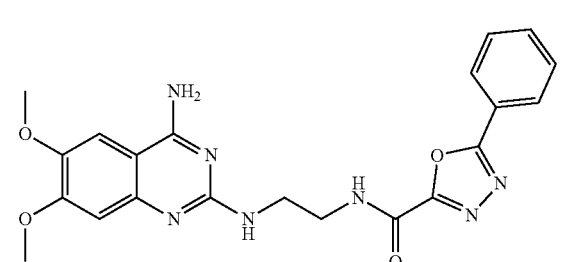 | 22.6 μM |
| BT2164 | 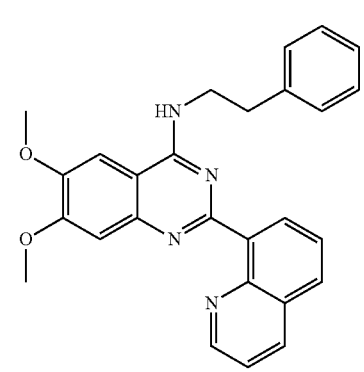 [SMILES: COc1cc2nc(-c3cccc4cccnc34)nc(NCCc3ccccc3)c2cc1OC] | 6.1 μM |

TABLE 1-continued
Heparanase inhibition (IC$_{50}$)
| Compound Code | Structure | IC$_{50}$ |
|---|---|---|
| BT2167 | 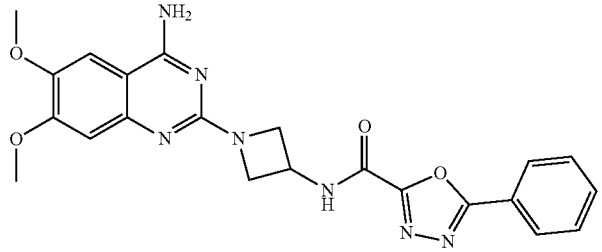 [SMILES: COc1cc2nc(N3CC(NC(=O)c4nnc(-c5ccccc5)o4)C3)nc(N)c2cc1OC] | 33 µM |
| BT2169 | 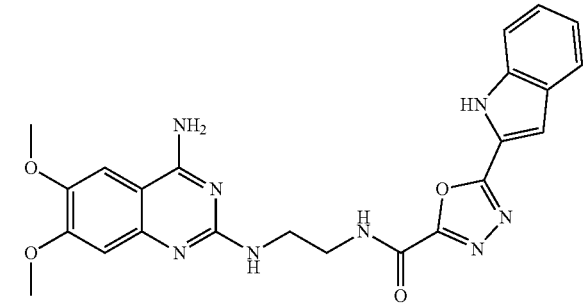 [SMILES: COc1cc2nc(NCCNC(=O)c3nnc(-c4cc5ccccc5[nH]4)o3)nc(N)c2cc1OC] | 3.3 µM |
| BT2170 | 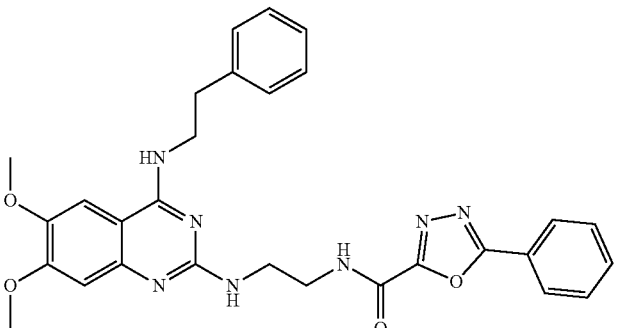 | 55 µM |
| BT2171 | 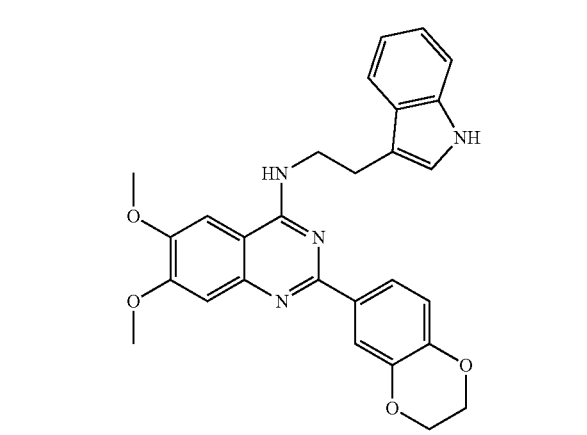 [SMILES: COc1cc2nc(-c3ccc4c(c3)OCCO4)nc(NCCc3c[nH]c4ccccc34)c2cc1OC] | 14 µM |
| BT2172 (BT2162 HCl) | 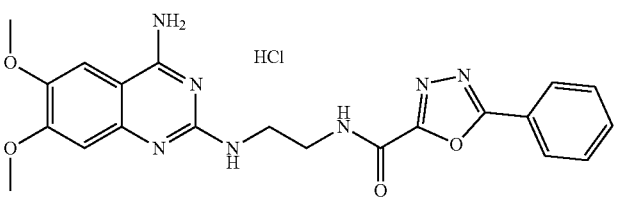 [SMILES: COc1cc2nc(NCCNC(=O)c3nnc(-c4ccccc4)o3)nc(N)c2cc1OC ; Cl] | 6.7 µM |

TABLE 1-continued

Heparanase inhibition (IC$_{50}$)

| Compound Code | Structure | IC$_{50}$ |
|---|---|---|
| BT2173 (BT2169 HCl) | 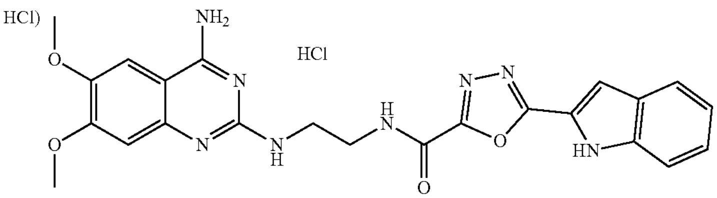 | 4.3 μM |
| BT2177 | 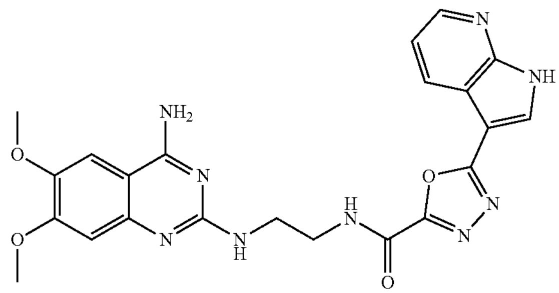 [SMILES: COc1cc2nc(NCCNC(=O)c3nnc(-c4c[nH]c5ncccc45)o3)nc(N)c2cc1OC] | 21 μM |
| BT2178 | 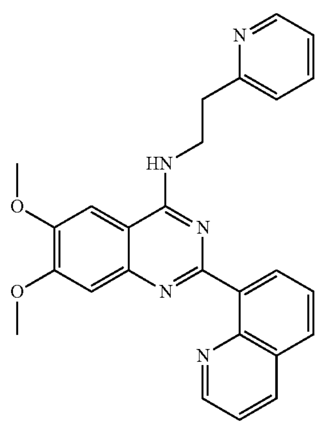 [SMILES: COc1cc2nc(-c3cccc4cccnc34)nc(NCCc3ccccn3)c2cc1OC] | 11 μM |
| BT2179 | 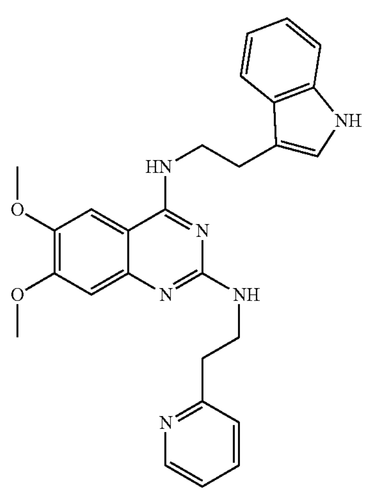 [SMILES: COc1cc2nc(NCCc3ccccn3)nc(NCCc3c[nH]c4ccccc34)c2cc1OC] | 18 μM |

TABLE 1-continued

Heparanase inhibition (IC$_{50}$)

| Compound Code | Structure | IC$_{50}$ |
|---|---|---|
| BT2181 | 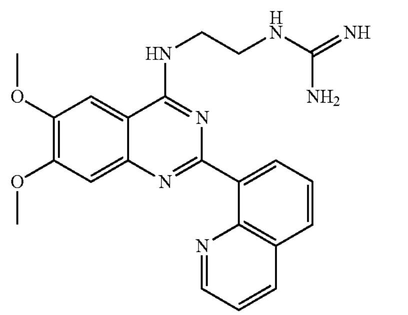 [SMILES: COc1cc2nc(-c3cccc4cccnc34)nc(NCCNC(=N)N)c2cc1OC] | 11 μM |
| BT2182 | TFA Salt | 18 μM |
| BT2184 | 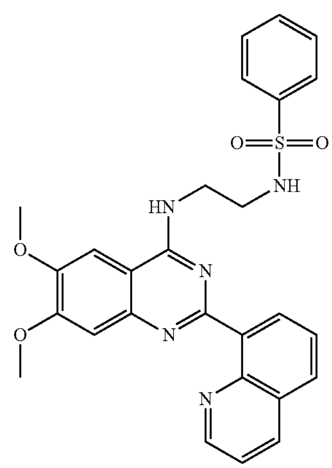 [SMILES: COc1cc2nc(-c3cccc4cccnc34)nc(NCCNS(=O)(=O)c3ccccc3)c2cc1OC] | 3.39 μM |
| BT2185 | 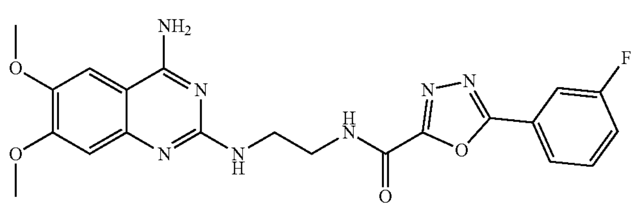 [SMILES: COc1cc2nc(NCCNC(=O)c3nnc(-c4cccc(F)c4)o3)nc(N)c2cc1OC] | 22 μM |

TABLE 1-continued

Heparanase inhibition (IC$_{50}$)

| Compound Code | Structure | IC$_{50}$ |
|---|---|---|
| BT2187 | 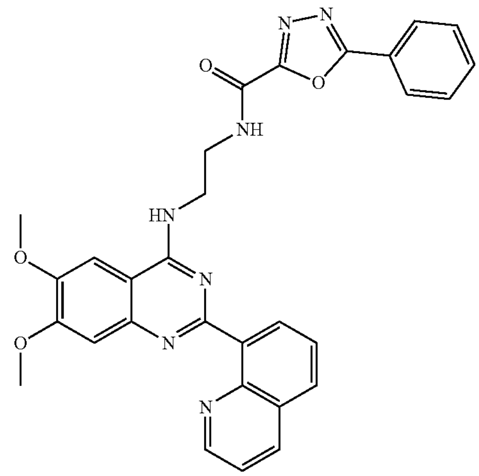 [SMILES: COc1cc2nc(-c3cccc4cccnc34)nc(NCCNC(=O)c3nnc(-c4ccccc4)o3)c2cc1OC] | 4.1 µM |
| BT2229 | 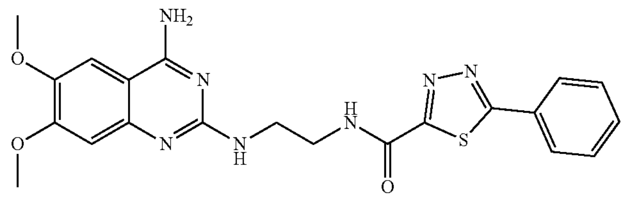 [SMILES: COc1cc2nc(NCCNC(=O)c3nnc(-c4ccccc4)s3)nc(N)c2cc1OC] | 13.4 µM |

Heparanase enzyme inhibition was further determined using a subset of compounds with direct comparison to a previously described heparanase inhibitor, OGT_2115, which was reported to have a relative heparanase inhibition activity of 400 µM as well as other biological activities (Courtney S M et al. *Bioorg Med Chem Lett,* 15:2295-9 (2005)). Average IC$_{50}$ values for each test compound are presented along with the previously with OGT_2115 (obtained from Tocris Biosciences) are presented in Table 2. Overall, the test compounds demonstrate similar or improved heparanase enzymatic inhibition to the control OGT_2115.

TABLE 2

Heparanase enzyme inhibition of select compounds compared to OGT_2115

| Compound Code | Structure | Average IC$_{50}$ (µM ± SEM) |
|---|---|---|
| BT2120 | 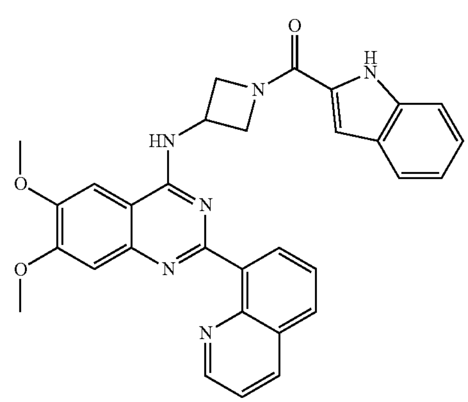 [SMILES: COc1cc2nc(-c3cccc4cccnc34)nc(NC3CN(C(=O)c4cc5ccccc5[nH]4)C3)c2cc1OC] | 0.70 ± 0.28 |

TABLE 2-continued

Heparanase enzyme inhibition of select compounds compared to OGT_2115

| Compound Code | Structure | Average IC$_{50}$ (μM ± SEM) |
|---|---|---|
| BT2184 | 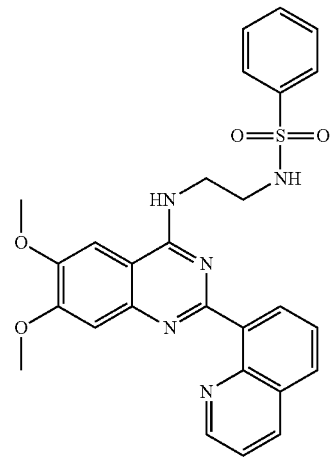 [SMILES: COc1cc2nc(-c3cccc4cccnc34)nc(NCCNS(=O)(=O)c3ccccc3)c2cc1OC] | 3.39 ± 0.33 |
| BT2187 | 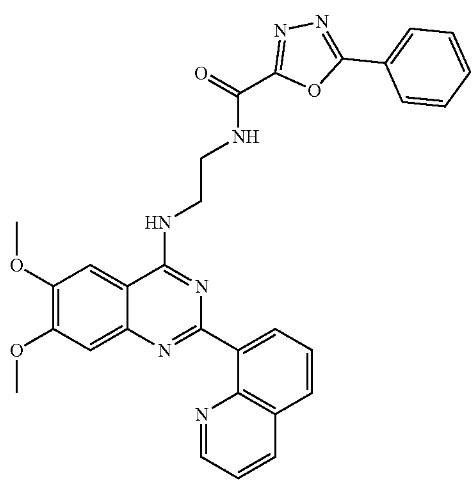 [SMILES: COc1cc2nc(-c3cccc4cccnc34)nc(NCCNC(=O)c3nnc(-c4ccccc4)o3)c2cc1OC] | 3.64 ± 0.62 |
| BT2169 | 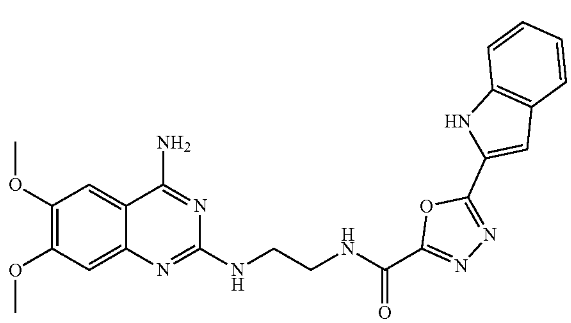 [SMILES: COc1cc2nc(NCCNC(=O)c3nnc(-c4cc5ccccc5[nH]4)o3)nc(N)c2cc1OC] | 4.00 ± 0.09 |

TABLE 2-continued

Heparanase enzyme inhibition of select compounds compared to OGT_2115

| Compound Code | Structure | Average IC$_{50}$ (µM ± SEM) |
|---|---|---|
| BT2164 | 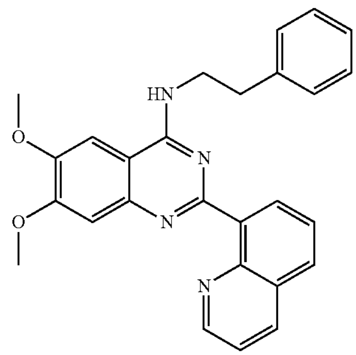 [SMILES: COc1cc2nc(-c3cccc4cccnc34)nc(NCCc3ccccc3)c2cc1OC] | 3.13 ± 0.72 |
| BT2229 | 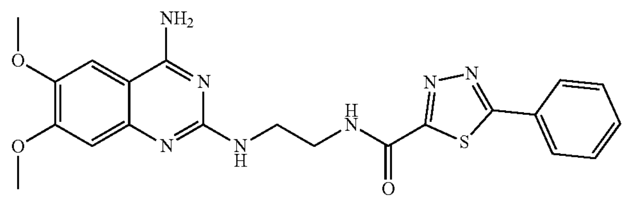 [SMILES: COc1cc2nc(NCCNC(=O)c3nnc(-c4ccccc4)s3)nc(N)c2cc1OC] | 13.4 ± 0.9 |
| BT2162 | 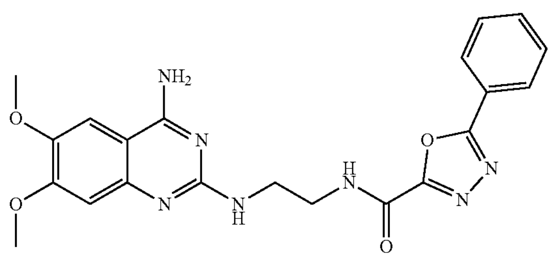 [SMILES: COc1cc2nc(NCCNC(=O)c3nnc(-c4ccccc4)o3)nc(N)c2cc1OC] | 22.6 ± 2.3 |
| OGT_2115 | 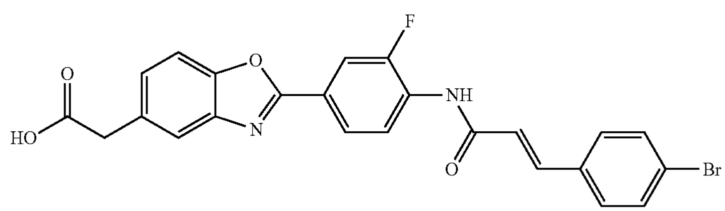 [SMILES: O=C(O)Cc1ccc2oc(-c3ccc(NC(=O)/C=C/c4ccc(Br)cc4)c(F)c3)nc2c1] | 7.68 ± 1.0 |

Example VII In Vivo Efficacy of Heparanase Inhibitors Following Photo-Oxidative Damage of the Retina Materials and Methods Animal Experimentation All experiments were conducted in accordance with the ARVO Statement for Use of Animals in Ophthalmic and Vision Research. The study was approved by the Australian National University Animal Experimentation Ethics Committee. C57BL6J mice were born and raised in 12:12 hrs light:dark cycle of 5 lux in individually vented cages, with free access to food and water. Age-matched adult mice (8-10 weeks) were randomly assigned to light damage and dim-reared control (non-light damage) groups. Animals of the light damage group were continuously exposed to 100 k lux white LED light for 1, 3, 5 and 7 days. Pupils were dilated twice daily at 10 am and 6 µm with a single drop of 1% atropine sulfate (8.3 mg of atropine). Dim-reared control animals were also pupil dilated twice each day, but were returned to dim cyclic light (12:12 hrs light:dark, 5 lux light).

Light Exposure Device

During bright-light exposure, animals were housed in plastic boxes (two per box), with free access to food and water. The floors of the cages were coated with a reflective Perspex surface and illuminated by a 100-W 65000 k natural white LED (high CRI LED, Yuji, Beijing) mounted 18 cm above the plastic boxes. The LED light has an emission spectrum which more closely resembles daylight than halogen or incandescent bulbs. Temperature in the cages was maintained at ~23±2° C. with a dual exhaust system to alleviate any heat generated from the LED, with one exhaust fan mounted next to the LED light source, and another one on the side of the cage. In order to regulate accurate illumination, each box was equipped with a dimmer and adjusted to 100 k lux using a light meter data logging device (Extech HD450). Animals were provided with bedding, food and water during the time course of light exposure, and their behaviour was monitored daily. All graphing and statistical analysis was performed using Prism 6 (GraphPad Software, CA, USA). Significant trends in time-course datasets were ascertained using the one-way or two-way analysis of variance (ANOVA) to determine statistical significance ($p<0.05$).

Measurement of Retinal Function Using Electroretinography (ERG)

Full-field scotopic ERGs were performed to assess the retinal function of dim-reared control and 7 days light damaged animals. Briefly, mice were dark adapted overnight, anesthetized by intraperitoneal injection of xylazine (10 mg/kg) and ketamine (100 mg/kg) and the pupils dilated with a single drop of 1% atropine sulfate (8.3 mg of atropine). A single- or twin-flash paradigm was used to elicit mixed (rod and cone) or isolated cone responses, respectively. Flash stimuli for mixed responses were provided by an LED-based system (FS-250A Enhanced Ganzfeld, Photometric Solutions International, Melbourne), over a stimulus intensity range of 6.3 log cd s m−2 (range 4.4-1.9 log cd s m$^{-2}$). Interstimulus interval was increased from 2 s for the lowest intensities to 5 min for the highest intensities to allow complete recovery of the b-wave between stimuli. Isolated cone responses were obtained at 1.6 log cd s m$^{-2}$ following a rod-saturating stimulus of 1.9 log cd s m$^{-2}$ given 400 ms before the test stimulus. This short interval after a rod-saturating flash does not allow recovery of rod function, thereby revealing cone-only responses. The a-wave amplitude was measured from the baseline to the trough of the a-wave response and the b-wave amplitude was measured from the trough of the a-wave to the peak of the b-wave. Data are expressed as the mean wave amplitude±SEM (μV). Two-way ANOVA, with Tukey's multiple comparisons post-hoc test, was performed to compare the responses from control and light damaged mice over the flash stimulus range. The a-wave and b-wave data were fitted with a Naka-Rushton equation [R/Rmax=I/(I+K)] using the Solver function in Excel (Microsoft Version 2013) to determine Rmax (maximum amplitude) and K (semisaturation constant) from the response amplitude (R) and the flash intensity (I) over the range of −4.4 to 1.9 log cd s m$^{-2}$. Statistics were performed using Prism (GraphPad Software V5; GraphPad Software, Inc., La Jolla, Calif., USA) and either a 2-way ANOVA for mixed a-wave and b-wave and students t-test for cone b-wave. For each analysis, differences with a $p<0.05$ were considered statistically significant (indicated by asterisks, *, in FIG. 8).

Intravitreal Injections

Intravitreal injections were performed as described in detail previously (Rutar M V et al (2012) J Neuroinflammation 9: 221) wherein animals were anesthetized using an intraperitoneal injection of ketamine (100 mg/kg; Troy Laboratories, NSW, Australia) and xylazil (12 mg/kg; Troy Laboratories).

The BT-2172 formulation was prepared as follows. BT2172 was suspended in ultrapure PBS to a concentration of 200 μM and sonicated until dissolved. The solution was filtered using a 0.22 μm syringe filtration system. Injections into individual animals consisted of a 1 μL solution containing PBS (control), or BT-2172 (200 μM).

Animals were allowed to wake from anesthesia, during which corneal hydration was maintained through application of a synthetic tear gel (GenTeal Gel; Novartis, NSW, Australia). Animals were then exposed to photo-oxidative damage for 5 days as described above.

Results

Figure 8A:
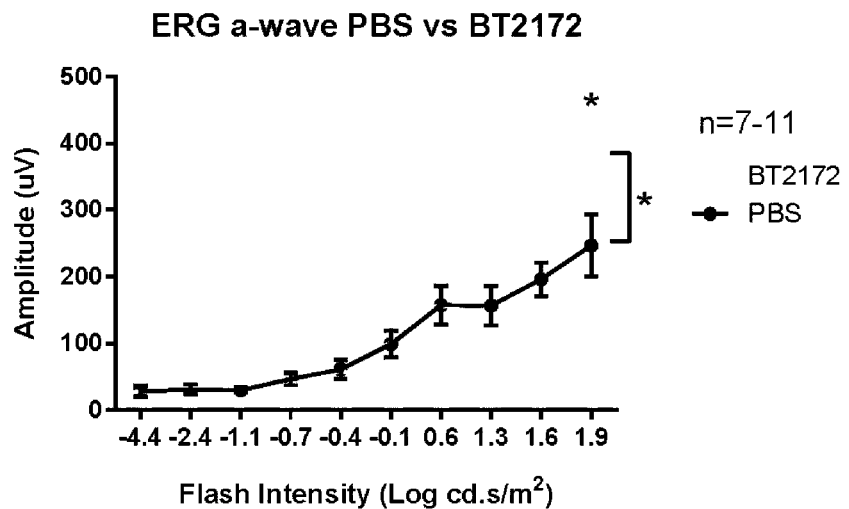
FIG. 8A presents the maintenance of retinal function by ERG analysis of a-wave and b-wave amplitudes over different flash intensities five days after induction of photo-oxidative damage and following treatment with the heparanase inhibitor BT-2172.
Figure 8A:
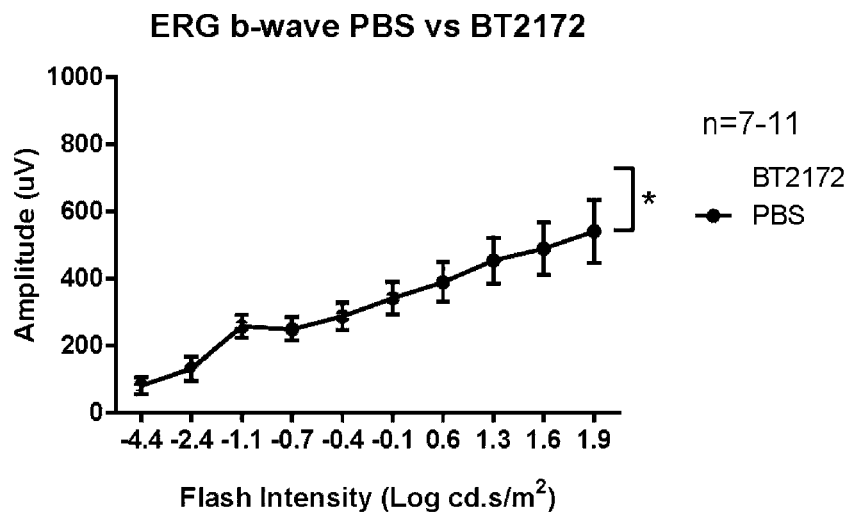
Figure 8B:
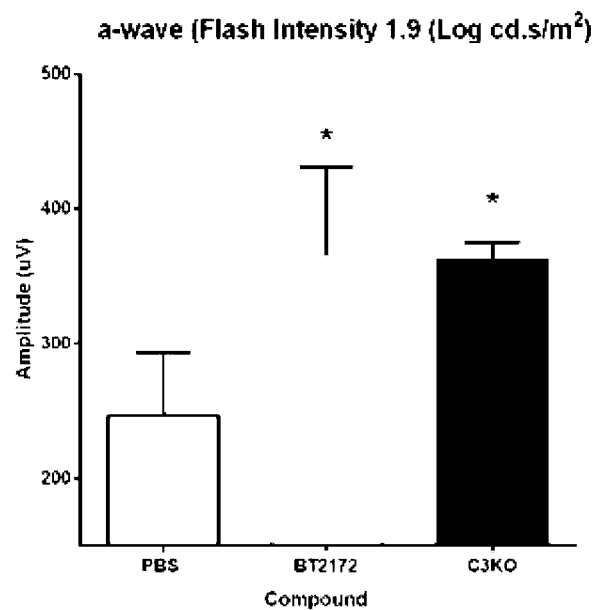
FIG. 8B presents the a-wave and b-wave amplitude at the highest flash intensity (1.9 cd·s/m$^2$) following treatment with the heparanase inhibitor BT-2172 in comparison to complement factor C3 knockout mouse eyes (C3KO) as well as untreated control (PBS) in normal mouse eyes five days after photo-oxidative damage. Significant trends in data points were ascertained using the one-way or two-way analysis of variance (ANOVA) to determine statistical significance (p<0.05) that is indicated by asterisks (*).
Figure 8B:
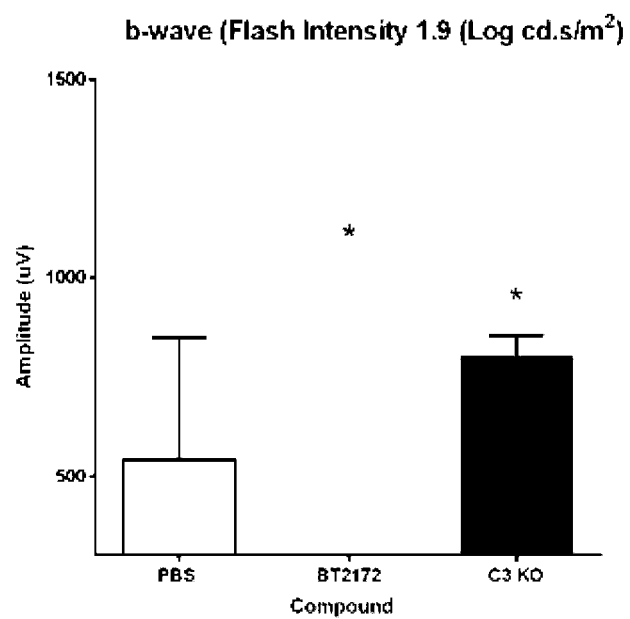
Figure 9:
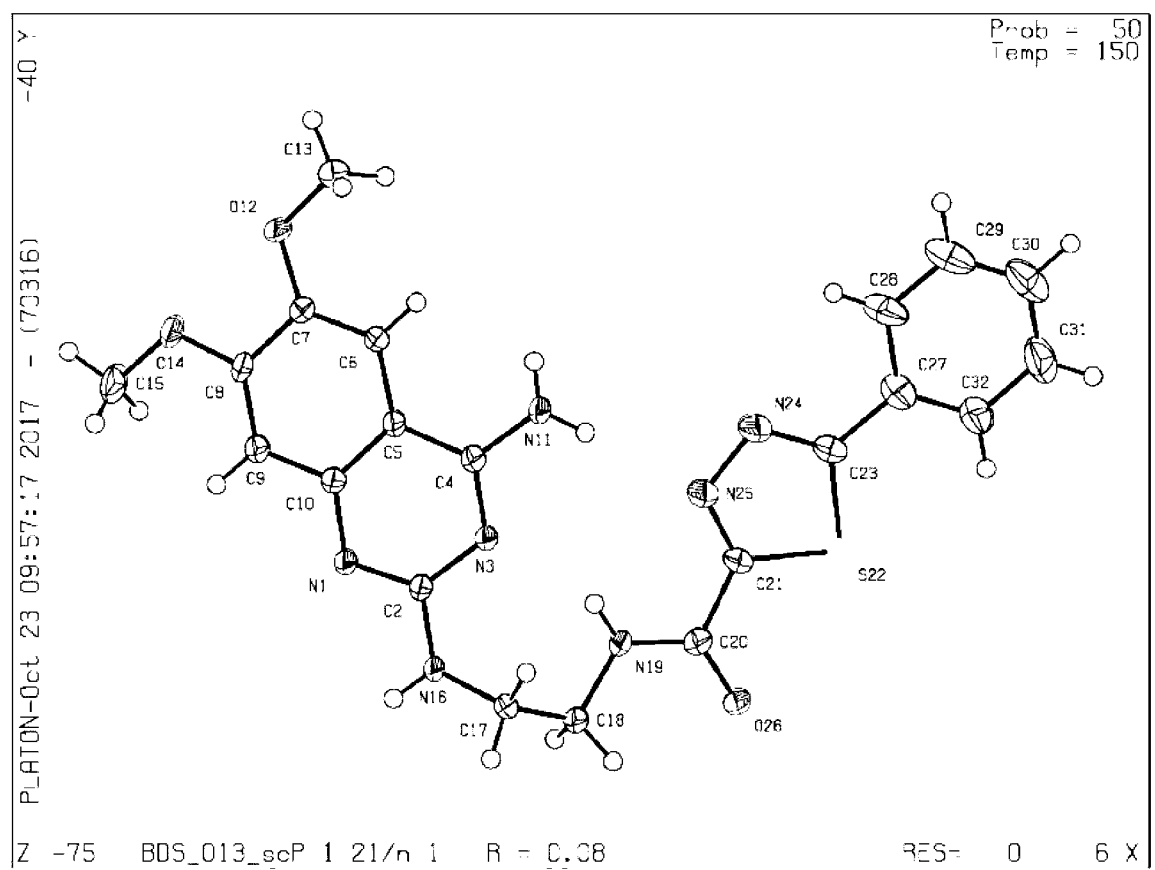
FIG. 9. X-ray crystal structure of compound BT2229 with labeling of selected atoms. Anisotropic displacement ellipsoids show 50% probability levels. Hydrogen atoms are drawn as circles with small radii.

The heparanase inhibitor BT-2172 delivered by intravitreal injection maintained retinal function (FIGS. 8A and 8B) in comparison to treatment with vehicle alone (PBS) and knocking out the C3 complement factor gene in mice exposed to photo-oxidative damage, a model related to dry age-related macular degeneration. The a-wave and b-wave responses of the ERG (FIG. 8A) reflects the differences in retinal morphology of untreated and treated animals described above. ERG a-wave and b-wave intensity response characteristics between BT-2172 treated mice was significantly different ($p<0.05$) compared to control mice (PBS). The benefit of BT-2172 treatment was demonstrated across multiple flash intensities and was most pronounced at the highest flash intensity ($p<0.05$, FIG. 8A). The BT-2172 treated had higher a- and b-wave responses than the control (PBS) group and was similar to the C3 complement factor gene knockout at high flash intensities (FIG. 8B).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A compound of the general formula

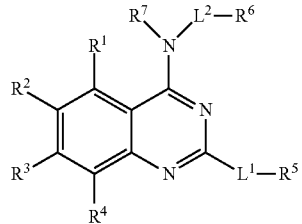

or a salt, hydrate, solvate, tautomer or stereoisomer thereof, wherein:

$R^1$ is selected from the group consisting of H, hydroxyl, halo, $C_{1-6}$ alkyl, $C_{1-4}$ alkoxy, O-CH$_2$phenyl, and O-phenyl;

$R^2$ is selected from the group consisting of H, hydroxyl, halo, $C_{1-6}$ alkyl, $C_{1-4}$ alkoxy, O-CH$_2$phenyl, and O-phenyl;

$R^3$ is selected from the group consisting of H, hydroxyl, halo, $C_{1-6}$ alkyl, $C_{1-4}$ alkoxy, O-CH$_2$phenyl, and O-phenyl;

$R^4$ is selected from the group consisting of H, hydroxyl, halo, $C_{1-6}$ alkyl, $C_{1-4}$ alkoxy, O-CH$_2$phenyl, and O-phenyl;

or $R^1$ and $R^2$, or $R^2$ and $R^3$, or $R^3$ and $R^4$ together form $C_{1-3}$alkylenedioxy;

wherein at least one of $R^1$, $R^2$, $R^3$ and $R^4$ is not H, $L^1$ is selected from the group consisting of NHC$_{1-4}$alkyl-NHC(O)—, azetidinyl-NHC(O)—, and azetidinyl-NHSO$_2$—;

$R^5$ is selected from the group consisting of $C_{3-9}$ cycloalkyl, naphthyl, $C_{2-9}$ N-heteroaryl optionally substituted with 1 or 2 $R^x$ groups, morpholinyl, piperidinyl, piperazinyl, and $C_{1-4}$ alkylC$_{2-5}$ heterocycloalkyl optionally substituted with 1 or 2 $R^x$ groups;

$L^2$ is selected from the group consisting of $C_{1-4}$ alkyl, azetidinyl-C(O)—, $C_{1-4}$alkyl-NHC(O)—, $C_{1-4}$alkyl-NHSO$_2$—, —C(O)—, and —SO$_2$—; or $L^2$ is absent;

R[6] is selected from the group consisting of H, $C_{2-6}$ alkyl, guanidinyl, NHC(NH)NH($C_{1-3}$alkyl), ureido, NHC(O)NH($C_{1-3}$alkyl), $C_{6-10}$ aryl optionally substituted with 1 or 2 R[X] groups, $C_{1-9}$ heteroaryl optionally substituted with 1 or 2 R[X] groups, $C_{2-5}$ heterocycloalkyl optionally substituted with 1 or 2 R[X] groups, and C3-9cycloalkyl optionally substituted with 1 or 2 R[X] groups;

R[7] is H or $C_{1-6}$ alkyl;

each R[X] is independently selected from the group consisting of hydroxyl, halo, nitro, NR'R'' (wherein R' and R'' are independently selected from H and $C_{1-3}$alkyl), $C_{1-4}$ alkyl, $C_{3-9}$cycloalkyl, halo$C_{1-4}$alkyl, $C_{1-4}$alkoxy, C(O)$C_{1-3}$alkyl, C(O)O$C_{1-4}$alkyl, C(O)NHR[Y], $C_{6-10}$aryl optionally substituted with 1 or 2 R[Y] groups, $C_{2-9}$heteroaryl optionally substituted with 1 or 2 R[Y] groups, $C_{1-4}$alkyl-($C_{2-9}$heteroaryl), $C_{2-5}$heterocycloalkyl optionally substituted with 1 or 2 $C_{1-4}$alkyl groups, $C_{1-4}$alkyl-($C_{2-5}$heterocycloalkyl) optionally substituted with 1 or 2 $C_{1-4}$alkyl groups, C(O)—$C_{2-9}$heteroaryl optionally substituted with 1 or 2 $C_{1-4}$ alkyl groups, SO2-$C_{2-9}$heteroaryl optionally substituted with 1 or 2 $C_{1-4}$ alkyl groups, and halo$C_{1-4}$ alkyl groups; or two adjacent R[X] groups together form $C_{1-3}$alkylenedioxy; and R[Y] is selected from the group consisting of H, hydroxyl, halo, $C_{1-4}$alkyl, halo$C_{1-4}$alkyl, and $C_{1-4}$alkoxy.

2. The compound according to claim 1, wherein each N-heteroaryl and each heterocycloalkyl has at least one nitrogen heteroatom.

3. The compound according to claim 1, wherein R[1] and R[4] are H and R[2] and R[3] are independently H, halo, or $C_{1-3}$alkoxy, or R[2] and R[3] together form methylenedioxy.

4. The compound according to claim 3, wherein R[1] and R[4] are H and R[2] and R[3] are both methoxy.

5. The compound according to claim 1, wherein R[5] is a group selected from the group consisting of cyclopropyl, indolyl, pyridyl, quinolinyl, isoquinolinyl, triazolyl, pyrazolyl, oxazolyl, oxadiazolyl, benzodiazolyl, and pyrrolopyridinyl, wherein each group is optionally substituted with 1 or 2 R[X] groups.

6. The compound according to claim 1, wherein R[7] is H, methyl or ethyl.

7. The compound according to claim 1, wherein L[2] is absent; R[6] is H and R[7] is H.

8. The compound according to claim 1, wherein L[2] is $C_{1-3}$alkyl; R[6] is indolyl, pyridyl or phenyl, wherein each group is optionally substituted with 1 or 2 R[X] groups; and R[7] is H.

9. The compound according to claim 1, wherein each R[X] is independently selected from the group consisting of hydroxyl, halo, $C_{1-3}$alkyl, halo$C_{1-3}$alkyl, $C_{1-3}$alkoxy, C(O)$C_{1-3}$alkyl, C(O)O$C_{1-3}$alkyl, NR'R'' (wherein R' and R'' are independently selected from H and $C_{1-3}$alkyl), phenyl optionally substituted with 1 or 2 R[Y] groups, morpholinyl optionally substituted with 1 or 2 R[Y] groups, piperazinyl optionally substituted with 1 or 2 R[Y] groups, C(O)piperazinyl optionally substituted with 1 or 2 R[Y] groups, C(O)morpholinyl optionally substituted with 1 or 2 R[Y] groups, pyridyl optionally substituted with 1 or 2 R[Y] groups, indolyl optionally substituted with 1 or 2 R[Y] groups, and SO2-indolyl optionally substituted with 1 or 2 R[Y] groups, or two adjacent R[X] groups together form methylenedioxy.

10. The compound according to claim 1, wherein R[Y] is selected from the group consisting of hydroxyl, halo, $C_{1-3}$alkyl, halo$C_{1-3}$alkyl, and $C_{1-3}$alkoxy.

11. The compound according to claim 1, wherein the compound is according to formula (IC), or a salt, hydrate, solvate, tautomer or stereoisomer thereof:

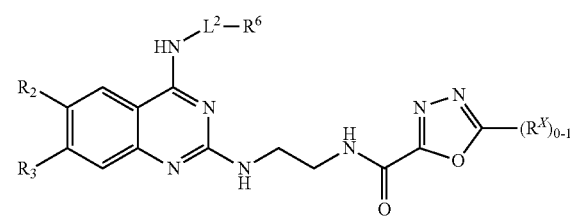

(IC)

12. A compound selected from

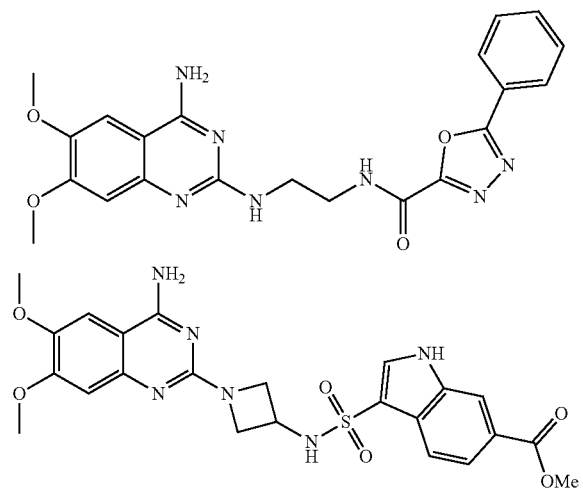

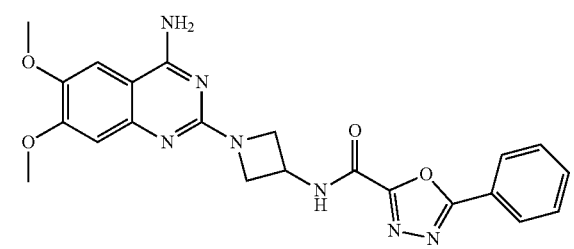

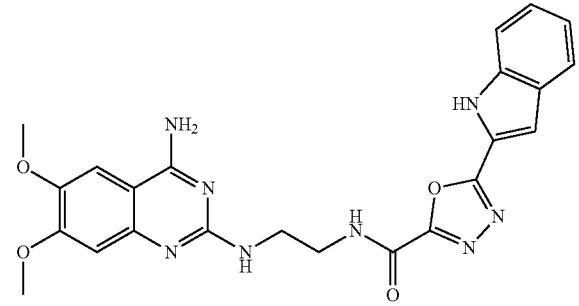

-continued

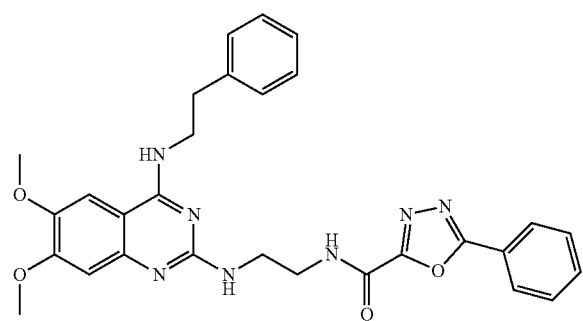

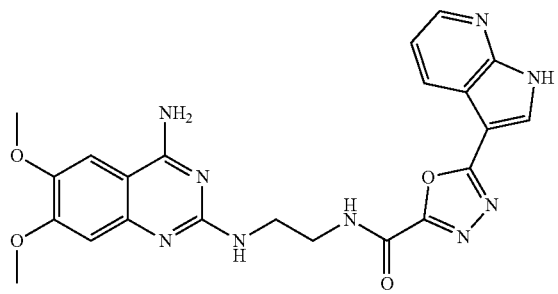

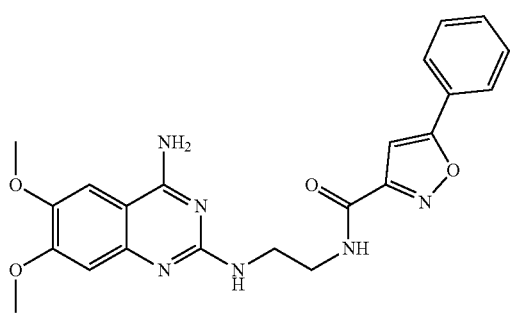

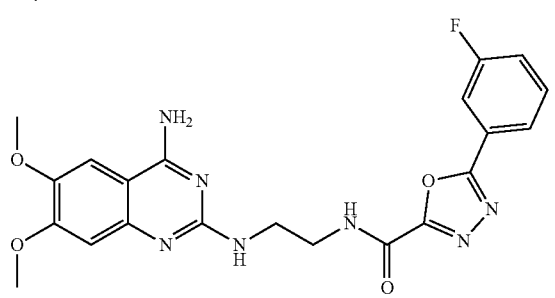

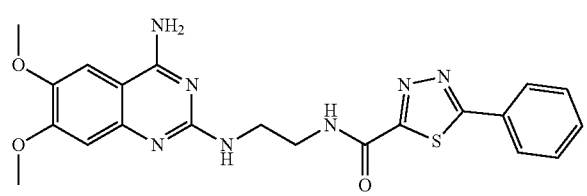

or a salt, hydrate, solvate, tautomer or stereoisomer thereof.

13. A pharmaceutical composition comprising a compound according to claim 1, together with a pharmaceutically acceptable carrier, diluent or excipient.

14. A method of palliative therapy for a disease or condition associated with heparanase activity in a subject, the method comprising administering to the subject an effective amount of a compound of general formula (I)

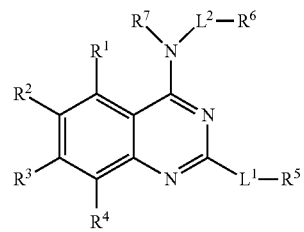

(I)

or a salt, hydrate, solvate, tautomer or stereoisomer thereof, wherein:

$R^1$ is selected from the group consisting of H, hydroxyl, halo, $C_{1-6}$ alkyl, $C_{1-4}$ alkoxy, O-$CH_2$phenyl, and O-phenyl;

$R^2$ is selected from the group consisting of H, hydroxyl, halo, $C_{1-6}$ alkyl, $C_{1-4}$ alkoxy, O-$CH_2$phenyl, and O-phenyl;

$R^3$ is selected from the group consisting of H, hydroxyl, halo, $C_{1-6}$ alkyl, $C_{1-4}$ alkoxy, O-$CH_2$phenyl, and O-phenyl;

$R^4$ is selected from the group consisting of H, hydroxyl, halo, $C_{1-6}$ alkyl, $C_{1-4}$ alkoxy, O-$CH_2$phenyl, and O-phenyl;

or $R^1$ and $R^2$, or $R^2$ and $R^3$, or $R^3$ and $R^4$ together form $C_{1-3}$alkylenedioxy;

$L^1$ is selected from the group consisting of $NHC_{1-4}$alkyl-NHC(O)—, azetidinyl-NHC(O)—, and azetidinyl-$NHSO_2$—;

$R^5$ is selected from the group consisting of $C_{3-9}$ cycloalkyl, naphthyl, $C_{2-9}$ N-heteroaryl optionally substituted with 1 or 2 $R^X$ groups, morpholinyl, piperidinyl, piperazinyl, $C_{1-4}$ alkyl$C_{2-5}$ heterocycloalkyl optionally substituted with 1 or 2 $R^X$ groups;

$L^2$ is selected from the group consisting of $C_{1-4}$ alkyl, azetidinyl-C(O)—, $C_{1-4}$alkyl-NHC(O)—, $C_{1-4}$alkyl-$NHSO_2$—, —C(O)—, and —$SO_2$—; or $L^2$ is absent;

$R^6$ is selected from the group consisting of H, $C_{2-6}$ alkyl, guanidinyl, NHC(NH)NH($C_{1-3}$alkyl), ureido, NHC(O)NH($C_{1-3}$alkyl), $C_{6-10}$ aryl optionally substituted with 1 or 2 $R^X$ groups, $C_{1-9}$ heteroaryl optionally substituted with 1 or 2 $R^X$ groups, $C_{2-5}$ heterocycloalkyl optionally substituted with 1 or 2 $R^X$ groups, and C3-9cycloalkyl optionally substituted with 1 or 2 $R^X$ groups;

$R^7$ is H or $C_{1-6}$ alkyl;

each $R^X$ is independently selected from the group consisting of hydroxyl, halo, nitro, NR'R" (wherein R' and R" are independently selected from H and $C_{1-3}$alkyl), $C_{1-4}$ alkyl, C3-cycloalkyl, halo$C_{1-4}$alkyl, $C_{1-4}$alkoxy, C(O)$C_{1-3}$alkyl, C(O)O$C_{1-4}$alkyl, C(O)NHR$^Y$, $C_{6-10}$aryl optionally substituted with 1 or 2 $R^Y$ groups, $C_{2-9}$heteroaryl optionally substituted with 1 or 2 $R^Y$ groups, $C_{1-4}$alkyl-($C_{2-9}$heteroaryl), $C_{2-5}$heterocycloalkyl optionally substituted with 1 or 2 $C_{1-4}$alkyl groups, $C_{1-4}$alkyl-($C_{2-5}$heterocycloalkyl) optionally substituted with 1 or 2 $C_{1-4}$alkyl groups, C(O)—$C_{2-9}$heteroaryl optionally substituted with 1 or 2 $C_{1-4}$ alkyl groups, $SO_2$—$C_{2-9}$heteroaryl optionally substituted with 1 or 2 $C_{1-4}$ alkyl groups, and halo$C_{1-4}$ alkyl groups;

or two adjacent $R^X$ groups together form $C_{1-3}$alkylenedioxy; and $R^Y$ is selected from the group consisting of H, hydroxyl, halo, $C_{1-4}$alkyl, halo$C_{1-4}$alkyl, and $C_{1-4}$alkoxy.

15. The method according to claim 14, wherein the disease or condition is selected from the group consisting of Type 1 diabetes, Type 2 diabetes, nephritis, glomerulonephritis, cell-mediated autoimmune inflammation, diabetic nephropathy, gestational diabetes, diabetic ketoacidosis, hyperglycemia, hyperosmolar state, hypoglycemia, diabetic coma, diabetic cardiomyopathy, diabetic neuropathy, diabetic foot, diabetic retinopathy, diabetic myonecrosis, diabetic encephalopathy, cancer, allergies, dermatitis, psoriasis, macular degeneration, retinitis pigmentosa, and pancreatitis.

16. The method according to claim 14, wherein the disease or condition is Type 1 diabetes or Type 2 diabetes.

17. A method of palliative therapy for a disease or condition associated with heparanase activity in a subject, the method comprising administering to the subject an effective amount of a compound of general formula (I)

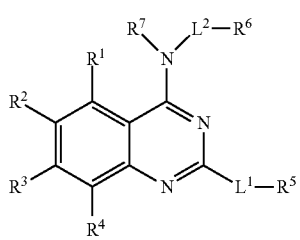

(I)

or a salt, hydrate, solvate, tautomer or stereoisomer thereof,
wherein:
$R^1$ is selected from the group consisting of H, hydroxyl, halo, $C_{1-6}$ alkyl, $C_{1-4}$ alkoxy, O-CH$_2$phenyl, and O-phenyl;
$R^2$ is selected from the group consisting of H, hydroxyl, halo, $C_{1-6}$ alkyl, $C_{1-4}$ alkoxy, O-CH$_2$phenyl, and O-phenyl;
$R^3$ is selected from the group consisting of H, hydroxyl, halo, $C_{1-6}$ alkyl, $C_{1-4}$ alkoxy, O-CH$_2$phenyl, and O-phenyl;
$R^4$ is selected from the group consisting of H, hydroxyl, halo, $C_{1-6}$ alkyl, $C_{1-4}$ alkoxy, O-CH$_2$phenyl, and O-phenyl;
or $R^1$ and $R^2$, or $R^2$ and $R^3$, or $R^3$ and $R^4$ together form $C_{1-3}$alkylenedioxy;
$L^1$ is selected from the group consisting of NHC$_{1-4}$alkyl-NHC(O)—, azetidinyl-NHC(O)—, and azetidinyl-NHSO$_2$—;
$R^5$ is selected from the group consisting of $C_{3-9}$ cycloalkyl, naphthyl, $C_{2-9}$ N-heteroaryl optionally substituted with 1 or 2 $R^X$ groups, morpholinyl, piperidinyl, piperazinyl, $C_{1-4}$ alkylC$_{2-5}$ heterocycloalkyl optionally substituted with 1 or 2 $R^X$ groups;

$L^2$ is selected from the group consisting of $C_{1-4}$ alkyl, azetidinyl-C(O)—, $C_{1-4}$alkyl-NHC(O)—, $C_{1-4}$alkyl-NHSO$_2$—, —C(O)—, and —SO$_2$—; or $L^2$ is absent;
$R^6$ is selected from the group consisting of H, $C_{2-6}$ alkyl, guanidinyl, NHC(NH)NH($C_{1-3}$alkyl), ureido, NHC(O)NH($C_{1-3}$alkyl), $C_{6-10}$ aryl optionally substituted with 1 or 2 $R^X$ groups, $C_{1-9}$ heteroaryl optionally substituted with 1 or 2 $R^X$ groups, $C_{2-5}$ heterocycloalkyl optionally substituted with 1 or 2 $R^X$ groups, and C3-9cycloalkyl optionally substituted with 1 or 2 $R^X$ groups;
$R^7$ is H or $C_{1-6}$ alkyl;
each $R^X$ is independently selected from the group consisting of hydroxyl, halo, nitro, NR'R" (wherein R' and R" are independently selected from H and $C_{1-3}$alkyl), $C_{1-4}$ alkyl, $C_{3-9}$cycloalkyl, haloC$_{1-4}$alkyl, $C_{1-4}$alkoxy, C(O)C$_{1-3}$alkyl, C(O)OC$_{1-4}$alkyl, C(O)NHR$^Y$, $C_{6-10}$aryl optionally substituted with 1 or 2 $R^Y$ groups, $C_{2-9}$heteroaryl optionally substituted with 1 or 2 $R^Y$ groups, $C_{1-4}$alkyl-($C_{2-9}$heteroaryl), $C_{2-5}$heterocycloalkyl optionally substituted with 1 or 2 $C_{1-4}$alkyl groups, $C_{1-4}$alkyl-($C_{2-5}$heterocycloalkyl) optionally substituted with 1 or 2 $C_{1-4}$alkyl groups, C(O)—$C_{2-9}$heteroaryl optionally substituted with 1 or 2 $C_{1-4}$ alkyl groups, SO$_2$—$C_{2-9}$heteroaryl optionally substituted with 1 or 2 $C_{1-4}$ alkyl groups, and haloC$_{1-4}$ alkyl groups;
or two adjacent $R^X$ groups together form $C_{1-3}$alkylenedioxy; and
$R^Y$ is selected from the group consisting of H, hydroxyl, halo, $C_{1-4}$alkyl, haloC$_{1-4}$alkyl, and $C_{1-4}$alkoxy, wherein the disease or condition is an ocular inflammatory disorder.

18. The compound according to claim 12, wherein the compound is

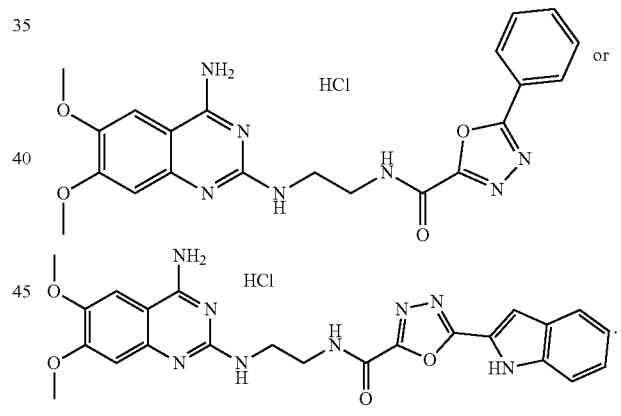

19. The compound according to claim 1, wherein $R^5$ is $C_{2-9}$ N-heteroaryl optionally substituted with 1 or 2 $R^X$ groups.

* * * * *